(12) United States Patent
Chen et al.

(10) Patent No.: US 11,958,899 B2
(45) Date of Patent: Apr. 16, 2024

(54) ANTI-C1s ANTIBODIES AND USES THEREOF

(71) Applicant: MABWELL THERAPEUTICS INC., San Diego, CA (US)

(72) Inventors: Buxin Chen, San Marcos, CA (US); Lei Huang, San Diego, CA (US); Xin Du, La Jolla, CA (US)

( * ) Notice: Subject to any disclaimer, the term of this patent is extended or adjusted under 35 U.S.C. 154(b) by 23 days.

(21) Appl. No.: 17/852,326

(22) Filed: Jun. 28, 2022

(65) Prior Publication Data

US 2023/0051715 A1 Feb. 16, 2023

Related U.S. Application Data

(60) Provisional application No. 63/342,544, filed on May 16, 2022, provisional application No. 63/221,131, filed on Jul. 13, 2021.

(51) Int. Cl.
C07K 16/18 (2006.01)

(52) U.S. Cl.
CPC .......... C07K 16/18 (2013.01); C07K 2317/24 (2013.01); C07K 2317/33 (2013.01); C07K 2317/34 (2013.01); C07K 2317/565 (2013.01); C07K 2317/76 (2013.01); C07K 2317/92 (2013.01)

(58) Field of Classification Search
None
See application file for complete search history.

(56) References Cited

U.S. PATENT DOCUMENTS

| 8,877,197 B2 | 11/2014 | Van Vlasselaer et al. |
| 8,945,562 B2 | 2/2015 | Van Vlasselaer et al. |
| 9,074,003 B2 | 7/2015 | Van Vlasselaer et al. |
| 9,074,004 B2 | 7/2015 | Van Vlasselaer et al. |
| 9,206,259 B2 | 12/2015 | Van Vlasselaer et al. |
| 9,512,233 B2 | 12/2016 | Van Vlasselaer et al. |
| 9,562,092 B2 | 2/2017 | Van Vlasselaer et al. |
| 9,562,106 B2 | 2/2017 | Van Vlasselaer et al. |
| 10,450,382 B2 | 10/2019 | Van Vlasselaer et al. |
| 10,457,745 B2 | 10/2019 | Van Vlasselaer et al. |
| 10,729,767 B2 | 8/2020 | Panicker et al. |
| 2019/0127454 A1 | 5/2019 | Yang et al. |
| 2021/0115116 A1 | 4/2021 | Van Vlasselaer et al. |

FOREIGN PATENT DOCUMENTS

| WO | 2004/011674 A1 | 2/2004 |
| WO | 2014/066744 A1 | 5/2014 |
| WO | 2014/071206 A1 | 5/2014 |
| WO | 2014/169076 A1 | 10/2014 |

(Continued)

OTHER PUBLICATIONS

PCT/US2022/035376 "Invitation To Pay Additional Fees And. Where Applicable, Protest Fee" dated Oct. 26, 2022.

(Continued)

*Primary Examiner* — Joanne Hama
*Assistant Examiner* — Gabrielle A Small
(74) *Attorney, Agent, or Firm* — Donna O. Perdue

(57) ABSTRACT

Antibodies and antigen-binding fragments thereof that bind C1s and inhibit C1s activity and modulate the activity of at least one component in the classical pathway (CP) of complement activation, and methods for treating complement-mediated disorders using anti-C1s antibodies and fragments, are provided.

22 Claims, 31 Drawing Sheets

Specification includes a Sequence Listing.

(56) References Cited

FOREIGN PATENT DOCUMENTS

| WO | 2014/186599 A2 | 11/2014 |
| WO | 2014/186622 A2 | 11/2014 |
| WO | 2016/164358 A1 | 10/2016 |
| WO | 2016/210172 A1 | 12/2016 |
| WO | 2017/180530 A1 | 10/2017 |
| WO | 2017/196874 A1 | 11/2017 |
| WO | 2018/017711 A1 | 1/2018 |
| WO | 2018/071676 A1 | 4/2018 |
| WO | 2018/170145 A1 | 5/2019 |
| WO | 2019/098212 A1 | 5/2019 |
| WO | 2019/198807 A1 | 10/2019 |

OTHER PUBLICATIONS

Bernd Jilma et al. "Chronic Inhibition of Complement CIs By TNT009 Produces Sustained, Complete Remission in Patients with Severe, Transfusion-Dependent Cold Agglutinin Disease (CAD)" Identified in ISR/WO as: "Internet Citation, Dec. 2, 2016 (Dec. 2, 2016), pp. 1-7, Retrieved from the Internet: URL:http://www.bloodjournal.org/content/12 8/22/2435 [retrieved on May 23, 2018] abstract"—includes image from Blood vol. 128 No. 22 pp. 2435-2435 (Dec. 2, 2016) DOI: https://doi.org/10.1182/blood.V128.22.2435.2435.

Bartko Johann et al: "A Randomized, First-in-Human, Healthy Volunteer Trial of sutimlimab, a Humanized Antibody for the Specific Inhibition of the Classical Complement Pathway" Clinical Pharmacology and Therapeutics, vol. 104, No. 4, Jul. 13, 2018 (Jul. 13, 2018), pp. 655-663, DOI: 10.1002/cpt. 1111.

International Search Report and Written Opinion, International Application No. PCT/US2022/035376 Completed Jan. 18. 2023: dated Jan. 26, 2023. Posted on WIPO Patentscope Jan. 23, 2023.

Phuan, P. W., Zhang, H., Asavapanumas, N., Leviten, M., Rosenthal, A., Tradtrantip, L., & Verkman, A. S. (2013). C1q-targeted monoclonal antibody prevents complement-dependent cytotoxicity and neuropathology in in vitro and mouse models of neuromyelitis optica. Acta neuropathologica, 125(6), 829-840. DOI: https://doi.org/10.1007/s00401-013-1128-3.

| anti-C1s mAb | HuC1s Form | $K_D$ (M) | $k_{on}$ (1/Ms) | $k_{off}$ (1/s) | $R^2$ |
|---|---|---|---|---|---|
| 2-7 | Active | 1.4E-10 | 3.5E+05 | 4.8E-05 | 0.9994 |
| 2-7 | Proenzyme | 1.4E-10 | 3.5E+05 | 4.8E-05 | 0.9994 |
| 2-8 | Active | 4.9E-10 | 2.5E+05 | 1.2E-04 | 0.9990 |
| 2-8 | Proenzyme | 4.9E-10 | 2.5E+05 | 1.2E-04 | 0.9990 |
| h2-7(H1L2) | Active | 2.4E-10 | 2.9E+05 | 7.0E-05 | 0.9998 |
| h2-8(H1L2 G80A/T82A) | Active | 1.2E-09 | 2.4E+05 | 2.9E-04 | 0.9998 |

FIG. 3E

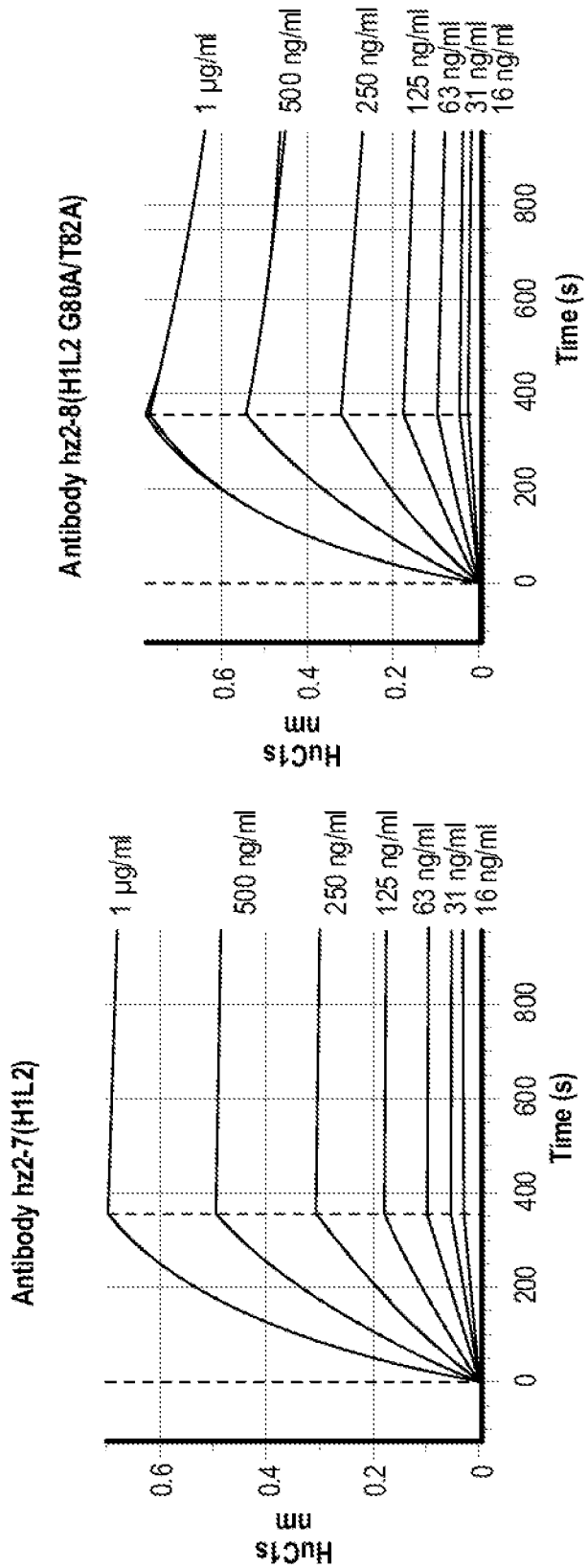

| anti-C1s mAb | C1s Species | $K_D$ (M) | $k_{on}$ (1/Ms) | $k_{off}$ (1/s) | $R^2$ |
|---|---|---|---|---|---|
| 2-7 | Human | 1.2E-11 | 3.2E+06 | 3.9E-05 | 0.9983 |
| 2-8 | | 3.2E-11 | 3.8E+06 | 1.2E-04 | 0.9992 |
| hz2-7(H1L2) | | 1.2E-10 | 3.9E+05 | 4.6E-05 | 0.9999 |
| hz2-8(H1L2 G80A/T82A) | | 7.0E-10 | 4.3E+05 | 3.0E-04 | 0.9997 |
| 2-7 | Mouse | | No Binding | | |
| 2-8 | | | | | |
| hz2-7(H1L2) | | | | | |
| hz2-8(H1L2 G80A/T82A) | | | | | |
| 2-7 | Rat | 1.7E-08 | 6.8E+04 | 1.2E-03 | 0.9776 |
| 2-8 | | | No Binding | | |
| hz2-7(H1L2) | | 1.6E-08 | 7.5E+04 | 1.2E-03 | 0.9718 |
| hz2-8(H1L2 G80A/T82A) | | 2.3E-10 | 2.8E+05 | 6.5E-05 | 0.9999 |
| 2-7 | Cyno Monkey | 1.1E-09 | 2.6E+05 | 2.8E-04 | 0.9996 |
| 2-8 | | 9.4E-10 | 2.5E+05 | 2.3E-04 | 0.9997 |
| hz2-7(H1L2) | | | | | |
| hz2-8(H1L2 G80A/T82A) | | 3.5E-09 | 2.3E+05 | 8.1E-04 | 0.9993 |

FIG. 3R

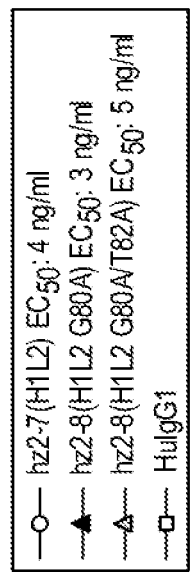
FIG. 6U
FIG. 6T
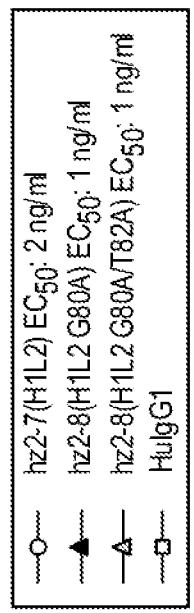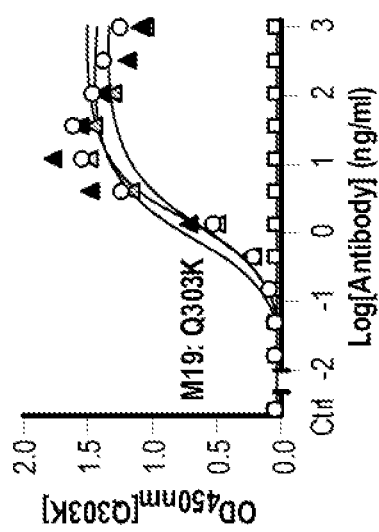

ANTI-C1s ANTIBODIES AND USES THEREOF

CROSS-REFERENCE TO RELATED APPLICATIONS

This application claims the benefit of U.S. Provisional Application No. 63/342,544 filed May 16, 2022, and U.S. Provisional Application No. 63/221,131 filed Jul. 13, 2021, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 28, 2022, is named SEQ_LIST_PIPL_1121-102US.txt and is 279,261 bytes in size.

FIELD OF THE INVENTION

The present disclosure relates to antibodies and antigen-binding fragments that bind to C1s protein, and treating complement-mediated disorders using antibodies and antigen-binding fragments that bind C1s protein.

BACKGROUND

The complement system is a tightly regulated network of proteins that form an important part of the innate and adaptive immune systems. With multiple activation pathways and a wide range of complement-mediated effector functions, the complement system plays a critical role in inflammation, defense against pathogens, and recovery after injury. Complement activation can have both beneficial and harmful effects. Defense responses mediated by complement activation can eliminate pathogens. Inappropriate, unwanted, excessive, or deficient complement activation has been associated with disease conditions such as certain autoimmune diseases and inflammatory syndromes, reflecting the intricate balancing act of complement between immune regulation and inflammatory tissue damage.

The complement system can be activated via three different pathways that converge at the effector stage wherein C3 convertase activates complement C3 protein and triggers a cascade of downstream effects. Each pathway has different triggers, initiator molecules, and enzyme cascades upstream of the generation of C3 convertase: (1) the classical pathway (CP) can be triggered when antibody-antigen complexes bind to the C1 complex and C1 is activated; (2) the alternative pathway (AP) can be triggered by cell surface constituents that are foreign to the host; and (3) the mannose-binding lectin pathway (LP) can be triggered when circulating lectin binds to mannose residues on microorganism surfaces. After the upstream cascade of each pathway generates C3 convertase, subsequent cleavage of complement proteins C3 and C5 result in: (1) generation of anaphylatoxins C3a and C5a, which attract and activate effector immune cells to the site of antibody binding/complement activation; (2) deposition of C3b opsonin that mediate phagocytosis and lymphocyte activation; and (3) triggering of the lytic pathway to form the membrane attack complex (MAC) that disrupts the cellular membrane and leads to cellular destruction.

The CP is not only critical to antibody-mediated defenses against foreign pathogens, but is also known or suspected to be involved in triggering immune responses to the engagement of autoantibody with self-antigen, i.e., autoimmune disorders. The CP is triggered by activation of the C1 complex, which normally circulates in the plasma as an inactive complex of its subcomponent proteins C1q, C1r and C1s. After recognizing and binding antibody-antigen complexes, the subcomponents of the C1 complex are sequentially activated in an enzyme cascade wherein binding of C1q to the Fc regions of two antigen-bound antibodies activates C1r subunits, which in turn activates C1s by cleaving C1s proenzyme into active C1s with two subcomponents (A and B chains) connected by an interchain disulfide bond. Activated C1s B chain is a serine protease that can, in turn, cleave serum C4 and C2 to form a C3 convertase, C4b2a. Formation of a C3 convertase in the CP then triggers downstream effector processes that are common to all three complement pathways.

C1s protein (complement component is) has a pivotal role in CP function, where C1s proenzyme in the inactive C1 complex must be cleaved into an active two-subunit (two-chain) C1s that can cleave and activate serum C4 in order for downstream effector cascades to proceed. For example, in human patients, deficiencies of C1s protein can lead to severe immune complex diseases because the immune complex deposits cannot be efficiently cleared without functional C1, C2 or C4, and subsequently normal levels of C3b. Some autoimmune and/or inflammatory disorders are known or suspected to involve spontaneous activation of the CP by complexes of autoantibodies bound to self-antigens, especially complement-fixing autoantibodies. Known complement-mediated disorders include paroxysmal nocturnal hemoglobinuria (PNH), atypical hemolytic uremic syndrome (atypical HUS), hereditary angioedema (HAE), age-related macular degeneration (AMD), and autoimmune hemolytic anemia such as cold agglutinin disease (CAD). A role for the complement system, in particular the CP, is suspected in certain autoimmune disorders such as immune thrombocytopenic purpura (ITP) which is an autoimmune bleeding disorder characterized by isolated thrombocytopenia with platelet count <150,000/μL, which is suspected to result from the development of autoantibody targeting of self-platelet antigens. A role for the CP is also suspected in neuromyelitis optica (NMO), an autoimmune disorder with inflammatory demyelinating lesions in the central nervous system, particularly in the spinal cord and optic nerve, that are thought to result from binding of anti-aquaporin-4 (AQP4) autoantibodies to astrocytes. Therapeutic approaches to treat complement-mediated disorders have included small molecule regulators such as protease inhibitors, although some known therapies such as C1 inhibitor C1 INH are known to exert effects beyond regulation of the CP, including modulation of the lectin pathway and kinin, coagulation and fibrinolytic systems. Therapeutic approaches using antibodies against components of the CP pathway are being explored.

SUMMARY

The invention relates to novel antibodies and antigen-binding fragments that bind human complement component is (C1s), and methods of making and using antibodies and antigen-binding fragments that bind C1s.

The present disclosure provides anti-C1s antibodies, anti-C1s antibody fragments that bind C1s, nucleic acids encoding anti-C1s antibodies and anti-C1s antibody fragments, and methods of making and using anti-C1s antibodies and anti-C1s antibody fragments. The term "anti-C1s antibodies" in the present disclosure encompasses anti-C1s antibodies and antigen-binding fragments thereof that are capable of binding C1s, in particular anti-C1s antibodies and antigen-binding fragments thereof that specifically bind C1s. Anti-C1s antibodies as disclosed herein are capable of binding proenzyme human C1s (native C1s). Anti-C1s antibodies as disclosed herein are capable of binding active human C1s. Anti-C1s antibodies as disclosed herein are capable of inhibiting C1s. Anti-C1s antibodies disclosed herein are capable of binding to proenzyme C1s and inhibiting C1s. Anti-C1s antibodies disclosed herein are capable of binding to active C1s and inhibiting C1s. Anti-C1s antibodies as disclosed herein are recombinant anti-C1s antibodies or antigen-binding fragments thereof that are capable of specifically binding to human C1s and inhibiting C1s.

The present disclosure provides anti-C1s antibodies for therapeutic and diagnostic uses in vivo, ex vivo, or in vitro. Anti-C1s antibodies as disclosed herein can be used to treat disorders mediated by the function of C1s. Anti-C1s antibodies as disclosed herein can be used to treat complement-mediated disorders, in particular disorders mediated by the classical pathway (CP) of complement activation. Anti-C1s antibodies as disclosed herein are capable of binding to C1s and inhibiting C1s, having effects on the activity of the CP pathway that can be measured by effects on the activity of at least one component of the CP downstream of C1s activation, where the component may be a molecule or a biological process associated with the CP. Anti-C1s antibodies as disclosed herein are capable of inhibiting the activity of the CP pathway. Anti-C1s antibodies as disclosed herein can be used to treat disorders mediated by the function of the CP. Anti-C1s antibodies as disclosed herein can be used to target C1s for selective inhibition of the CP in complement-mediated autoimmune and/or inflammatory disorders. Anti-C1s antibodies as disclosed herein can be used to treat complement-mediated autoimmune and/or inflammatory disorders including but not limited to immune thrombocytopenic purpura (ITP) or neuromyelitis optica (NMO).

In certain embodiments, anti-C1s antibodies disclosed herein are capable of binding to proenzyme (native) C1s and inhibiting effects of C1s activation. In certain embodiments, anti-C1s antibodies disclosed herein are capable of binding to active C1s and inhibiting effects of C1s activation. Anti-C1s antibodies disclosed herein are capable inhibiting or more effects of C1s activation on at least one downstream component. In certain embodiments, the downstream component is at least one of cleavage of C2 and/or cleavage of C4 and/or formation of C3 covertase, and/or serum complement-induced lysis of antibody sensitized cells, and the binding of anti-C1s antibodies to active C1s has the effect of inhibiting cleavage of C2 and/or cleavage of C4 and/or formation of C3 covertase, and/or serum-induced lysis of antibody sensitized cells.

In one aspect, anti-C1s antibodies are provided that are capable of binding to C1s and modulating at least one effect of antibody-antigen complex triggered CP activation. In certain embodiments, anti-C1s antibodies disclosed herein are capable of modulating at least one effect of antibody-antigen complex triggered CP activation in a dose-dependent manner. In certain embodiments, anti-C1s antibodies disclosed herein are capable of inhibiting at least one effect of antibody-antigen complex triggered CP activation in a dose-dependent manner. In certain embodiments, anti-C1s antibodies disclosed herein are capable or inhibiting serum-induced lysis of antibody sensitized cells in a dose-dependent manner.

In one aspect, anti-C1s antibodies are provided that are capable of having the effect of modulating the activity of at least one component involved in antibody-antigen complex triggered C4 cleavage and/or deposition. In certain embodiments, anti-C1s antibodies disclosed herein are capable of inhibiting the activity of at least one component involved in IgM-triggered deposition of C4 from serum. In certain embodiments, anti-C1s antibodies disclosed herein are capable of inhibiting IgM-triggered deposition of human C4 from human serum in a dose-dependent manner. In certain embodiments, anti-C1s antibodies disclosed herein are capable of modulating the activity of at least one component involved in IgM-triggered deposition of cynomolgus monkey C4 from cynomolgus monkey serum, in a dose-dependent manner. In certain embodiments, anti-C1s antibodies disclosed herein are capable of inhibiting IgM-triggered deposition of cynomolgus monkey C4 from cynomolgus monkey serum in a dose-dependent manner.

In another aspect, anti-C1s antibodies are provided that have selective effects within the CP, upstream of the generation and activity of common complement system effectors. In certain embodiments, selective inhibition of the CP by anti-C1s antibodies disclosed herein prevents C4 cleavage and downstream effects triggered by C4 cleavage. In certain embodiments, anti-C1s antibodies disclosed herein prevent C3 convertase formation through the CP pathway.

In another aspect anti-C1s antibodies are provided that bind to C1s proenzyme and to active C1s protein. In certain embodiments, anti-C1s antibodies disclosed herein bind to C1s proenzyme and to active C1s protein with similar affinity. In certain embodiments, anti-C1s antibodies disclosed herein specifically bind to C1s proenzyme and to active C1s protein with similar high affinity, with KD values in the low nanomolar to picomolar range.

In another aspect, anti-C1s antibodies are provided that show cross-reactivity with at least one non-human C1s. In certain embodiments, anti-C1s antibodies disclosed herein may be capable of binding human C1s and rat C1s. In certain embodiments, anti-C1s antibodies disclosed herein may be capable of binding human C1s and cynomolgus monkey C1s. In certain embodiments, anti-C1s antibodies disclosed herein may be capable of binding human C1s, rat C1s, and cynomolgus monkey C1s. In certain embodiments, anti-C1s antibodies disclosed herein do not show detectable binding to mouse C1s.

In another aspect, anti-C1s antibodies are provided that bind to an epitope that is accessible on proenzyme C1s and on active C1s, in the internal region of C1s within a 151-amino acid region spanning from residues Y272 to R422 (M151) in the N-terminus heavy chain (NHC), with key residues including R316, K336 and a subregion of G390 to R422 of human C1s (SEQ ID NO: 99).

An anti-C1s antibody as provided herein is recombinantly expressed and is a recombinant antibody. An anti-C1s antibody as provided herein may further be one or more of a humanized antibody, a chimeric antibody, a single chain antibody, a Fab fragment, a single-chain variable fragment (scFv), an aptamer, a single-domain antibody (VHH, nanobody, camelid antibody), or any other C1s-binding fragment or variant. In particular, an anti-C1s antibody disclosed here is a humanized antibody. In certain embodiments, an anti-C1s antibody disclosed herein may comprise a framework in which amino acids have been substituted into an existing antibody framework, in particular to influence properties such as antigen-binding ability. In certain embodiments, an anti-C1s antibody disclosed herein may comprise complementarity determining regions (CDRs) from a source (parental) antibody that have been grafted (fused) into a framework from a different type (class) of antibody and/or from a different organism than the parental antibody, in particular an acceptor human framework. In certain embodiments, an anti-C1s antibody disclosed herein may comprise a framework in which amino acids have been substituted, mutated, or replaced in regions outside of the CDRs to influence properties such as antigen-binding or antibody structure, e.g., in the variable region framework surrounding the CDRs and/or in a constant region, in particular the Fe region. In certain embodiments, one or more of the CDRs have been substituted, mutated, or replaced. In certain embodiments, an anti-C1s antibody disclosed herein may be a humanized anti-C1s antibody variant.

In certain embodiments, an anti-C1s antibody disclosed herein comprises at least one polypeptide having an amino acid sequence as set forth in Table 1 ("Variable Regions of Anti-C1s Antibodies") or the Sequence Listing, or a sequence substantially identical (e.g., a sequence at least about 85%, 90%, 92%, 95%, 97%, or 98%, 99% identical) to an amino acid sequence as set forth in Table 1 or the Sequence Listing. Anti-C1s antibodies disclosed herein may comprise at least one polypeptide having an amino acid sequence selected from the following, or a sequence substantially identical (e.g., a sequence at least about 85%, 90%, 92%, 95%, 97%, or 98%, 99% identical) to at least one polypeptide having an amino acid sequence selected from the following: SEQ ID NO: 1; SEQ ID NO: 2; SEQ ID NO: 3; SEQ ID NO: 4; SEQ ID NO: 6; SEQ ID NO: 7; SEQ ID NO: 8; SEQ ID NO: 9; SEQ ID NO: 11; SEQ ID NO: 12; SEQ ID NO: 13; SEQ ID NO: 14; SEQ ID NO: 16; SEQ ID NO: 17; SEQ ID NO: 18; SEQ ID NO: 19; SEQ ID NO: 21; SEQ ID NO: 22; SEQ ID NO: 23; SEQ ID NO: 24; SEQ ID NO: 26; SEQ ID NO: 27; SEQ ID NO: 28; SEQ ID NO: 29; SEQ ID NO: 31; SEQ ID NO: 32; SEQ ID NO: 33; SEQ ID NO: 34; SEQ ID NO: 36; SEQ ID NO: 37; SEQ ID NO: 38; SEQ ID NO: 39; SEQ ID NO: 41; SEQ ID NO: 42; SEQ ID NO: 43; SEQ ID NO: 44; SEQ ID NO: 46; SEQ ID NO: 47; SEQ ID NO: 48; SEQ ID NO: 49; SEQ ID NO: 51; SEQ ID NO: 52; SEQ ID NO: 53; SEQ ID NO: 54; SEQ ID NO: 56; SEQ ID NO: 57; SEQ ID NO: 58; SEQ ID NO: 59; SEQ NO: 61; SEQ NO: 62; SEQ NO: 63; SEQ NO: 64; SEQ NO: 66; SEQ NO: 67; SEQ ID NO: 68; SEQ ID NO: 69; SEQ NO: 71; SEQ NO: 73; SEQ NO: 75; SEQ ID NO: 77; SEQ ID NO: 79; SEQ ID NO: 81; SEQ ID NO: 83; SEQ ID NO: 85; SEQ ID NO: 87; SEQ ID NO: 89; SEQ ID NO: 91; SEQ ID NO: 93; SEQ ID NO: 95; SEQ ID NO: 97; SEQ ID NO: 129; SEQ ID NO: 130; SEQ ID NO: 131; SEQ ID NO: 132; SEQ ID NO: 133; SEQ ID NO: 134; SEQ ID NO: 135; SEQ ID NO: 136; SEQ ID NO: 137; SEQ ID NO: 138; SEQ ID NO: 139; or SEQ ID NO: 140.

In one embodiment, an anti-C1s antibody disclosed herein comprises a heavy chain variable region (VH) polypeptide having the amino acid sequence set forth in SEQ ID NO: 1 or a sequence substantially identical to SEQ ID NO: 1, and a light chain variable region (VL) polypeptide having the amino acid sequence set forth in SEQ JD NO: 6 or a sequence substantially identical to SEQ ID NO: 6. In one embodiment, an anti-C1s antibody disclosed herein comprises a heavy chain complementarity determining region 1 (HC CDR1) having the amino acid sequence set forth in SEQ ID NO: 2, a heavy chain complementarity determining region 2 (HC CDR2) having the amino acid sequence set forth in SEQ ID NO: 3, a heavy chain complementarity determining region 3 (HC CDR3) having the amino acid sequence set forth in SEQ JD NO: 4; a light chain complementarity determining region 1 (LC CDR1) having the amino acid sequence set forth in SEQ ID NO: 7, a light chain complementarity determining region 2 (LC CDR2) having the amino acid sequence set forth in SEQ ID NO: 8, and a light chain complementarity determining region 3 (LC CDR3) having the amino acid sequence set forth in SEQ ID NO: 9; or a variant of said antibody comprising 1, 2, 3, 4, 5, or 6 amino acid substitutions in the CDR regions. In one non-limiting embodiment, an anti-C1s antibody disclosed herein is the antibody identified herein as 2-7, comprising an HC polypeptide having the amino acid sequence set forth in SEQ ID NO: 71 and an LC polypeptide having the amino acid sequence set forth in SEQ ID NO: 73.

In one embodiment, an anti-C1s antibody disclosed herein comprises VH polypeptide having the amino acid sequence set forth in SEQ ID NO: 11 or a sequence substantially identical to SEQ ID NO: 11, and an VL polypeptide having the amino acid sequence set forth in SEQ ID NO: 16 or a sequence substantially identical to SEQ ID NO: 16. In one embodiment, an anti-C1s antibody disclosed herein comprises an HC CDR1 having the amino acid sequence set forth in SEQ ID NO: 12, an HC CDR2 having the amino acid sequence set forth in SEQ ID NO: 13, an HC CDR3 having the amino acid sequence set forth in SEQ ID NO: 14; an LC CDR1 having the amino acid sequence set forth in SEQ ID NO: 17, an LC CDR2 having the amino acid sequence set forth in SEQ ID NO: 18, and an LC CDR3 having the amino acid sequence set forth in SEQ JD NO: 19, or a variant of said antibody comprising 1, 2, 3, 4, 5, or 6 amino acid substitutions in the CDR regions. In one non-limiting embodiment, an anti-C1s antibody disclosed herein is of the antibody identified herein as 2-8, comprising an HC polypeptide having the amino acid sequence set forth in SEQ ID NO: 75 and an LC polypeptide having the amino acid sequence set forth in SEQ ID NO: 77.

In one embodiment, an anti-C1s antibody disclosed herein comprises a VH polypeptide having the amino acid sequence set forth in SEQ ID NO: 21 or a sequence substantially identical to SEQ ID NO: 21, and a VL polypeptide having the amino acid sequence set forth in SEQ ID NO: 26 or a sequence substantially identical to SEQ ID NO: 26. In one embodiment, an anti-C1s antibody disclosed herein comprises an HC CDR1 having the amino acid sequence set forth in SEQ ID NO: 22, an HC CDR2 having the amino acid sequence set forth in SEQ ID NO: 23, an HC CDR3 having the amino acid sequence set forth in SEQ ID NO: 24; an LC CDR1 having the amino acid sequence set forth in SEQ ID NO: 27, an LC CDR2 having the amino acid sequence set forth in SEQ ID NO: 28, and an LC CDR3 having the amino acid sequence set forth in SEQ ID NO: 29, or a variant of said antibody comprising 1, 2, 3, 4, 5, or 6 amino acid substitutions in the CDR regions. In one non-limiting embodiment, an anti-C1s antibody disclosed herein is the antibody identified herein as hz2-7(H1L2), comprising an HC polypeptide having the amino acid sequence set forth in SEQ ID NO: 79 and an LC polypeptide having the amino acid sequence set forth in SEQ ID NO: 81.

In one embodiment, an anti-C1s antibody disclosed herein comprises a VH polypeptide having the amino acid sequence set forth in SEQ ID NO: 31 or a sequence substantially identical to SEQ ID NO: 31, and a VL polypeptide having the amino acid sequence set forth in SEQ ID NO: 36 or a sequence substantially identical to SEQ ID NO: 36. In one embodiment, an anti-C1s antibody disclosed herein comprises an HC CDR1 having the amino acid sequence set forth in SEQ ID NO: 32, an HC CDR2 having the amino acid sequence set forth in SEQ ID NO: 33, an HC CDR3 having the amino acid sequence set forth in SEQ ID NO: 34; an LC CDR1 having the amino acid sequence set forth in SEQ ID NO: 37, an LC CDR2 having the amino acid sequence set forth in SEQ ID NO: 38, and an LC CDR3 having the amino acid sequence set forth in SEQ ID NO: 39, or a variant of said antibody comprising 1, 2, 3, 4, 5, or 6 amino acid substitutions in the CDR regions. In one non-limiting embodiment, an anti-C1s antibody disclosed herein is the antibody identified herein as hz2-7(H1 L2 G131A), comprising an HC polypeptide having the amino acid sequence set forth in SEQ ID NO: 83 and an LC polypeptide having the amino acid sequence set forth in SEQ ID NO: 85.

In one embodiment, an anti-C1s antibody disclosed herein comprises an HC variable region polypeptide having the amino acid sequence set forth in SEQ ID NO: 41 or a sequence substantially identical to SEQ ID NO: 41, and an LC variable region polypeptide having the amino acid sequence set forth in SEQ ID NO: 46 or a sequence substantially identical to SEQ ID NO: 46. In one embodiment, an anti-C1s antibody disclosed herein comprises an HC CDR1 having the amino acid sequence set forth in SEQ ID NO: 42, an HC CDR2 having the amino acid sequence set forth in SEQ ID NO: 43, an HC CDR3 having the amino acid sequence set forth in SEQ ID NO: 44; an LC CDR1 having the amino acid sequence set forth in SEQ ID NO: 47, an LC CDR2 having the amino acid sequence set forth in SEQ ID NO: 48, and an LC CDR3 having the amino acid sequence set forth in SEQ ID NO: 49, or a variant of said antibody comprising 1, 2, 3, 4, 5, or 6 amino acid substitutions in the CDR regions. In one non-limiting embodiment, an anti-C1s antibody disclosed herein is the antibody identified herein as hz2-8(H1L2), comprising an HC polypeptide having the amino acid sequence set forth in SEQ ID NO: 87 and an LC polypeptide having the amino acid sequence set forth in SEQ ID NO: 89.

In one embodiment, an anti-C1s antibody disclosed herein comprises a VH polypeptide having the amino acid sequence set forth in SEQ ID NO: 51 or a sequence substantially identical to SEQ ID NO: 51, and a VL polypeptide having the amino acid sequence set forth in SEQ ID NO: 56 or a sequence substantially identical to SEQ ID NO: 56. In one embodiment, an anti-C1s antibody disclosed herein comprises an HC CDR1 having the amino acid sequence set forth in SEQ ID NO: 52, an HC CDR2 having the amino acid sequence set forth in SEQ ID NO: 53, an HC CDR3 having the amino acid sequence set forth in SEQ ID NO: 54; an LC CDR1 having the amino acid sequence set forth in SEQ ID NO: 57, an LC CDR2 having the amino acid sequence set forth in SEQ ID NO: 58, and an LC CDR3 having the amino acid sequence set forth in SEQ ID NO: 59, or a variant of said antibody comprising 1, 2, 3, 4, 5, or 6 amino acid substitutions in the CDR regions. In one non-limiting embodiment, an anti-C1s antibody disclosed herein is the antibody identified herein as hz2-8 (H1L2 G80A/T82A), comprising an 14C polypeptide having the amino acid sequence set forth in SEQ ID NO: 91 and an LC polypeptide having the amino acid sequence set forth in SEQ ID NO: 93.

In one embodiment, an anti-C1s antibody disclosed herein comprises a VH polypeptide having the amino acid sequence set forth in SEQ ID NO: 61 or a sequence substantially identical to SEQ ID NO: 61, and a VL polypeptide having the amino acid sequence set forth in SEQ ID NO: 66 or a sequence substantially identical to SEQ ID NO: 66. In one embodiment, an anti-C1s antibody disclosed herein comprises an HC CDR1 having the amino acid sequence set forth in SEQ ID NO: 62, an HC CDR2 having the amino acid sequence set forth in SEQ ID NO: 63, an HC CDR3 having the amino acid sequence set forth in SEQ ID NO: 64; an LC CDR1 having the amino acid sequence set forth in SEQ ID NO: 67, an LC CDR2 having the amino acid sequence set forth in SEQ ID NO: 68, and an LC CDR3 having the amino acid sequence set forth in SEQ ID NO: 69, or a variant of said antibody comprising 1, 2, 3, 4, 5, or 6 amino acid substitutions in the CDR regions. In one non-limiting embodiment, an anti-C1s antibody disclosed herein is the antibody identified herein as hz2-8 (H1 L2 G80A) comprising an HC polypeptide having the amino acid sequence set forth in SEQ ID NO: 95 and an LC polypeptide having the amino acid sequence set forth in SEQ ID NO: 97.

In another aspect, CDR consensus sequences of an anti-C1s antibody disclosed herein are provided. Table 1.b. discloses non-limiting exemplary embodiments of anti-C1s antibody CDR consensus sequences. In one embodiment, an antibody is provided wherein the VH comprises an HC CDR1 having an amino acid sequence set forth in SEQ ID NO: 129, an HC CDR2 having an amino acid sequence set forth in SEQ ID NO: 130, and an HC CDR3 having an amino acid sequence set forth in SEQ ID NO: 131, and the VL comprises an LC CDR1 having an amino acid sequence set forth in SEQ ID NO: 132, an LC CDR2 having an amino acid sequence set forth in SEQ ID NO: 133, and an LC CDR3 having an amino acid sequence set forth in SEQ ID NO: 134. In another embodiment, an antibody is provided wherein the VH comprises an HC CDR1 having an amino acid sequence set forth in SEQ ID NO: 135, an HC CDR2 having an amino acid sequence set forth in SEQ ID NO: 136, and an HC CDR3 having an amino acid sequence set forth in SEQ ID NO: 137, and the VL comprises an LC CDR1 having an amino acid sequence set forth in SEQ ID NO: 138, an LC CDR2 having an amino acid sequence set forth in SEQ ID NO: 139, and an LC CDR3 having an amino acid sequence set forth in SEQ ID NO: 140.

In another aspect, anti-C1s antibodies (including variants and fragments as disclosed herein) are provided that can be used to treat disorders mediated by CP activation, including but not limited to disorders mediated by antibody-antigen complex triggered CP activation, and in particular disorders associated with or characterized by CP activation by autoantibodies bound to self-antigen. Methods and compositions are provided for using anti-C1s antibodies disclosed herein for therapeutic uses including but not limited to treating disorders mediated by CP activation, in particular disorders characterized by CP activation by autoantibodies bound to self-antigens. Methods and compositions are provided for using anti-C1s antibodies as disclosed herein for therapeutic uses including treating ITP and/or NMO. In certain embodiments, pharmaceutical compositions comprising an anti-C1s antibody disclosed herein and a suitable carrier and/or excipient are provided.

In another aspect, methods for treating a complement-mediated disorder are provided, such methods comprising administering an effective amount of an anti-C1s antibody disclosed herein to a subject in need thereof. In accordance with this aspect, methods for treating a complement-mediated disorder comprise administering an effective amount of an anti-C1s antibody disclosed herein to have the effect of modulating or inhibiting one or more biological effects associated with antibody-antigen complex triggered CP activation. In accordance with this aspect, an effective amount of anti-C1s antibody is the amount of antibody sufficient to cause a desired level of modulation or inhibition. In certain embodiments, methods comprise administration of an effective amount of anti-C1s antibody to a subject that results in modulating one or more biological effects associated with CP activation by autoantibodies bound to self-antigen, including but not limited to reduced lysis of platelets triggered by anti-platelet antibodies and/or antibody-mediated removal of platelets.

In another aspect, methods for treating a disease or disease state in which unwanted, abnormal, inappropriate, or excessive CP activation is involved are provided, such methods comprising administering an effective amount of an anti-C1s antibody disclosed herein to a subject in need thereof.

In another aspect, methods for diagnosing or screening for a complement-mediated disorder in a subject are provided. Methods for diagnosing or screening for a complement-mediated disorder can be practiced in vivo, ex vivo, or in vitro. In certain embodiments, methods comprise administering anti-C1s antibody to a subject known or suspected to have a complement-mediated autoimmune disorder and measuring one or more biological effect or symptom associated with a complement-mediated autoimmune disorder. In certain embodiments, ex vivo or in vino methods comprise administering anti-C1s antibody to a sample taken from a subject and measuring one or more biological effect or symptom associated with a complement-mediated autoimmune disorder.

In another aspect, one or more isolated nucleic acid molecules are provided that encode at least a portion of at least one of the anti-C1s antibodies disclosed herein. In certain embodiments, isolated nucleic acid molecules that encode at least a portion of at least one of the anti-C1s antibodies disclosed herein comprise a nucleotide sequence set forth in Table 2 herein, or a sequence substantially identical (e.g., a sequence at least about 85%, 90%, 92%, 95%, 97%, or 98%, 99% identical) to a nucleotide sequence set forth in Table 2. In certain embodiments, isolated nucleic acid molecules that encode at least one of the heavy chain (HC) sequences of the anti-C1s antibodies disclosed herein may comprise a nucleotide sequence selected from at least one of: SEQ ID NO: 5 or a sequence substantially identical to SEQ ID NO: 5; SEQ ID NO: 15 or a sequence substantially identical to SEQ ID NO: 15; SEQ ID NO: 25 or a sequence substantially identical to SEQ ID NO: 25; SEQ ID NO: 35 or a sequence substantially identical to SEQ ID NO: 35; SEQ ID NO: 45 or a sequence substantially identical to SEQ ID NO: 45; SEQ ID NO: 55 or a sequence substantially identical to SEQ ID NO: 55; SEQ ID NO: 65 or a sequence substantially identical to SEQ ID NO: 65; SEQ ID NO: 72 or a sequence substantially identical to SEQ ID NO: 72; SEQ ID NO: 76 or a sequence substantially identical to SEQ ID NO: 76; SEQ ID NO: 80 or a sequence substantially identical to SEQ ID NO: 80; SEQ ID NO: 84 or a sequence substantially identical to SEQ ID NO: 84; SEQ ID NO: 88 or a sequence substantially identical to SEQ ID NO: 88; SEQ ID NO: 92 or a sequence substantially identical to SEQ ID NO: 92; or SEQ ID NO: % or a sequence substantially identical to SEQ ID NO: %.

In certain embodiments, isolated nucleic acid molecules that encode at least one of the light chain (LC) sequences of the anti-C1s antibodies or antigen-binding fragments thereof disclosed herein may comprise a nucleotide sequence selected from at least one of: SEQ ID NO: 10 or a sequence substantially identical to SEQ ID NO: 10; SEQ ID NO: 20 or a sequence substantially identical to SEQ ID NO: 20; or SEQ ID NO: 30 or a sequence substantially identical to SEQ ID NO: 30; SEQ ID NO: 40 or a sequence substantially identical to SEQ ID NO: 40; SEQ ID NO: 50 or a sequence substantially identical to SEQ ID NO: 50; SEQ ID NO: 60 or a sequence substantially identical to SEQ ID NO: 60; SEQ ID NO: 70 or a sequence substantially identical to SEQ ID NO: 70; SEQ ID NO: 74 or a sequence substantially identical to SEQ ID NO: 74; SEQ ID NO: 78 or a sequence substantially identical to SEQ ID NO: 78; SEQ ID NO: 82 or a sequence substantially identical to SEQ ID NO: 82; SEQ ID NO: 86 or a sequence substantially identical to SEQ ID NO: 86; SEQ ID NO: 90 or a sequence substantially identical to SEQ ID NO: 90; SEQ ID NO: 94 or a sequence substantially identical to SEQ ID NO: 94; or SEQ ID NO: 98 or a sequence substantially identical to SEQ ID NO: 98.

In another aspect, a vector is provided comprising one or more nucleic acid molecules that encode at least one amino acid sequence of the anti-C1s antibodies disclosed herein. In certain embodiments, a vector is provided comprising one or more nucleic acid molecules that encode at least one of the sequences of the heavy chain (HC) or light chain (LC) of anti-C is antibodies disclosed herein.

In another aspect, at least one host cell is provided containing a vector comprising one or more nucleic acid molecules that encode amino acid sequences of the anti-C1s antibodies disclosed herein. In certain embodiments, host cells are transiently transfected with a vector comprising one or more nucleic acid molecules that encode amino acid sequences of anti-C1s antibodies or antigen-binding fragments thereof disclosed herein, wherein the host cells are capable of supporting vector expression and recombinant production of anti-C1s antibodies or antigen-binding fragments thereof encoded by the vector.

BRIEF DESCRIPTION OF THE FIGURES

FIG. 2A shows the effects of anti-C1s antibody 2-7, anti-C1s antibody 2-8, and an antibody from non-functional clone 3-30, on IgM-induced deposition of human C4 from human serum (NHS), over the indicated range of antibody concentrations. FIG. 2B shows the effects of anti-C1s antibody 2-7 and anti-C1s antibody 2-8 on IgM-induced deposition of cynomolgus monkey C4 from cynomolgus monkey serum (CMS) over the indicated range of antibody concentrations. In FIGS. 2A-2B, symbols are used as follows: open circles represent results using an anti-C1s antibody 2-7; open triangles represent results using an anti-C1s antibody 2-8; open squares represent results using an anti-C1s antibody 3-30. FIG. 2C shows the effects of humanized anti-C1s antibody hz2-7(H1L2), humanized anti-C1s antibody hz2-8(H1L2), humanized anti-C1s antibody variant hz2-7(H1L2 G131A), humanized anti-C1s antibody variant hz2-8(H1L2 G80A), and humanized anti-C1s antibody variant hz2-8(H1L2 G80A/T82A) on IgM-induced deposition of human C4 from human serum (NHS), over the indicated range of antibody concentrations. FIG. 2D shows the effects of humanized anti-C1s antibody hz2-7 (H1L2), humanized anti-C1s antibody hz2-8(H1L2), humanized anti-C1s antibody variant hz2-7(H1L2 G131A), humanized anti-C1s antibody variant hz2-8(H1L2 G80A), and humanized anti-C1s antibody variant hz2-8(H1L2 G80A/T82A) on IgM-induced deposition of cynomolgus monkey C4 from cynomolgus monkey serum (CMS) over the indicated range of antibody concentrations. In FIGS. 2C-2D, symbols are used as follows: open circles represent results using an anti-C1s antibody hz2-7(H1L2); black filled circles represent results using an anti-C1s antibody hz2-7 (H1L2 G131A); open triangles represent results using an anti-C1s antibody hz2-8(H1L2); black filled triangles represent results using an anti-C1s antibody hz2-8(H1L2 G80A); and triangles with diagonal lines represent results using an anti-C1s antibody hz2-8(H1L2 G80A/T82A).

FIGS. 3A-3V show results of determinations of binding affinity and cross-reactivity of anti-C1s antibodies. FIGS. 3A-3D show results using Bio-Layer Interferometry technology for measuring anti-C1s antibody affinity and determining binding kinetics for active human C1s protein with the OCTET® RED96e system using AHC biosensors, by combining antibody with indicated concentrations of active human C1s protein over the times indicated, where FIG. 3A shows results for anti-C1s antibody 2-7 binding to active human C1s, FIG. 3B shows results for anti-C1s antibody 2-8 binding to active human C1s, FIG. 3C shows humanized anti-C1s antibody hz2-7(H1L2) binding to active human C1s, and FIG. 3D shows humanized anti-C1s variant hz2-8(H1L2 G80A/T82A) binding to active human C1s. FIG. 3E is a summary table showing KD, $k_{on}$, $k_{off}$ and $R^2$ values calculated for each indicated combination of antibody and target. FIG. 3F shows results for binding to active human C1s by the indicated concentrations of 2-7, 2-8, hz2-7(H1L2) and hz2-8(H1L2 G80A/T82A) with human IgG1 as a control, and FIG. 3G shows results for binding to human C1s proenzyme by the indicated concentrations of 2-7, 2-8, hz2-7(H1 L2) and hz2-8(H1 L2 G80A/T82A) with human IgG1 as a control. FIGS. 3H-3Q show results using Bio-Layer Interferometry technology for measuring anti-C1s antibody affinity and determining binding kinetics for recombinant C1s from human (HuC1s, FIGS. 3H-3K), rat (RaC1s, FIGS. 3L-3M), and cynomolgus monkey (CyC1s, FIGS. 3N-3Q) sources, where FIG. 3H shows binding by 2-7 to human C1s (HuC1s), FIG. 3I shows binding by 2-8 to HuC1s. FIG. 3J shows binding by hz2-7(H1l2) to HuC1s, FIG. 3K shows binding by hz2-8(H1L2 G80A/T82A) to HuC1s, FIG. 3L shows binding by 2-8 to RaC1s, FIG. 3M shows binding by hz2-8(H1L2 G80A/T82A) to RaC1s, FIG. 3N shows binding by 2-7 to CyC1s, FIG. 3O shows binding by 2-8 to CyC1s, FIG. 3P shows binding by hz2-7(H1L2) to CyC1s, and FIG. 3Q shows binding by hz2-8(H1L2 G80A/T82A) to CyC1s. FIG. 3R is a summary table showing KD, $k_{on}$, $k_{off}$ and $R^2$ values calculated for each indicated combination of antibody and target. FIGS. 3S-3V show results for anti-C1s antibody cross-reactivity measurements using ELISA, where the figures show binding by the indicated concentrations of 2-7, 2-8, hz2-7(H1 L2), hz2-8(H1 L2 G80A/T82A), and IgGs (controls) to human C1s (HuC1s, FIG. 3S), mouse C1s (MoC1s, FIG. 3T), rat C1s (RatC1s, FIG. 3U), and cynomolgus monkey C1s (CyC1s, FIG. 3V). In FIGS. 3F-3G and 3S-3V, symbols are used as follow: open circles represent results using an anti-C1s antibody 2-7; open triangles represent results using an anti-C1s antibody 2-8; open squares represent results using mouse IgG; black filled circles represent results using an anti-C1s antibody hz2-7(H1L2); black filled triangles represent results using an anti-C1s antibody hz2-8(H1 L2 G80A-782A) and black filled squares represent results using human IgG1.

FIG. 4A shows binding of 2-7, 2-8, hz2-7(H1L2), hz2-8(H1L2), and IgG controls (mouse IgG, human Ig1) to full-length human C1s (HuC1s). FIG. 4B shows binding of 2-7, 2-8, hz2-7(H1L2), hz2-8(H1L2), and IgG controls (mouse IgG, human IgG1) to full-length mouse C1s (MoC1s). FIG. 4C shows binding of 2-7, 2-8, hz2-7(H1L2), hz2-8(H1L2), and IgG controls (mouse IgG, human IgG1) to truncated human C1s NHC (HuC1s(NHC)). FIG. 4D shows binding of 2-7, 2-8, hz2-7 (H1L2), hz2-8(H1L2), and IgG controls (mouse IgG, human IgG1) to truncated human C1s M151 (HuC1s(M151)). In FIGS. 4A-4D, symbols are used as follows: open circles represent results using an anti-C1s antibody 2-7; open triangles represent results using an anti-C1s antibody 2-8; open squares represent results using mouse IgG; black filled circles represent results using an anti-C1s antibody hz2-7 (H1L2); black filled triangles represent results using an anti-C1s antibody hz2-8(H1L2); and black filled squares represent results using human IgG1.

FIG. 5A shows an image of binding of a representative anti-C1s antibody 2-8 to the full-length and different truncated forms of C1s measured using western blotting. 200 ng full-length human C1s (HuC1s) in lane 1, 200 ng full length mouse C1s (MoC1s) in lane 2,200 ng truncated human C1s M151 (HuC1s(M151)) in lane3, and 200 ng truncated human C1s NHC (HuC1s(NHC)) in lane 4 were resolved on SDS-PAGE under non-reducing (left blot) and reducing (right blot) conditions, followed by a transfer to nitrocellulose membrane (blots). Blocked blots were incubated with antibody 2-8 and developed with HRP-labelled secondary antibodies. In the blot of the gel running without reducing agent (left), lane 1 shows antibody 2-8 binding to full-length human C1s (HuC1s, upper band) and auto-cleaved C1s heavy chain (lower band), lane 2 shows no binding of antibody 2-8 to full length mouse C1s (MoC1s) (no detectable antibody binding), lane 3 shows antibody 2-8 binding to multiple isoforms of truncated human C1s M151 (HuC1s(M151)), and lane 4 shows antibody 2-8 binding to truncated human C1s NHC (HuC1s(NHC)). On the blot of the gel running with reducing agent (right), lane 1 shows a low level of antibody 2-8 binding to an auto-cleaved C1s heavy chain from the full-length human C1s (HuC1s), lane 2 shows no binding of antibody 2-8 to full length mouse C1s (MoC1s)(no detectable binding), lane 3 shows antibody 2-8 binding to truncated human C1s M151 (HuC1s(M151)), and lane 4 shows antibody 2-8 binding to truncated human C1s NHC (HuC1s(NHC)). FIG. 5B shows a schematic comparison and alignment of full-length human C1s, HuC1s (e.g., as exemplified in SEQ ID NO: 99), human C1s deletion mutant 1 (M151) designated HuC1s(M151) or M151 (e.g., as exemplified in SEQ ID NO: 107), human deletion mutant 2 (NHC) designated HuC1s(NHC) or NHC (e.g., as exemplified in SEQ ID NO: 109) and human C1s deletion mutant 3 (NHCΔ33) designated human C1s (NHCΔ33) or NHCΔ33 (e.g., as exemplified in SEQ ID NO:111). FIG. 5B also shows the location of point mutations introduced into HuC1s, M151, NHC, and NHCΔ33 in Example 6.

FIGS. 6A-6U shows results for binding measurements of hz2-7(H1L2), hz2-8(H1L2 G80A), hz2-8(H1L2 G80A/T82A) and human IgG1 (control) to NHCΔ33 and point mutants M1-M20 of human C1s using ELISA as follows: FIG. 6A shows binding to NHCΔ33; FIG. 6T shows binding to M19 (Q303K); and FIG. 6U shows binding to M20 (A320S). In FIGS. 6A to 6U, symbols are used as follows: open circles represent results using an anti-C1s antibody hz2-7(H1L2); black filled triangles represent results using an anti-C1s antibody hz2-8(H1L2 G80A); triangles with diagonal lines represent results using an anti-C1s antibody hz2-8(H1L2 G80A/T82A), and open squares represent results using human IgG1 (HuIgG1).

DETAILED DESCRIPTION

Figure 1:
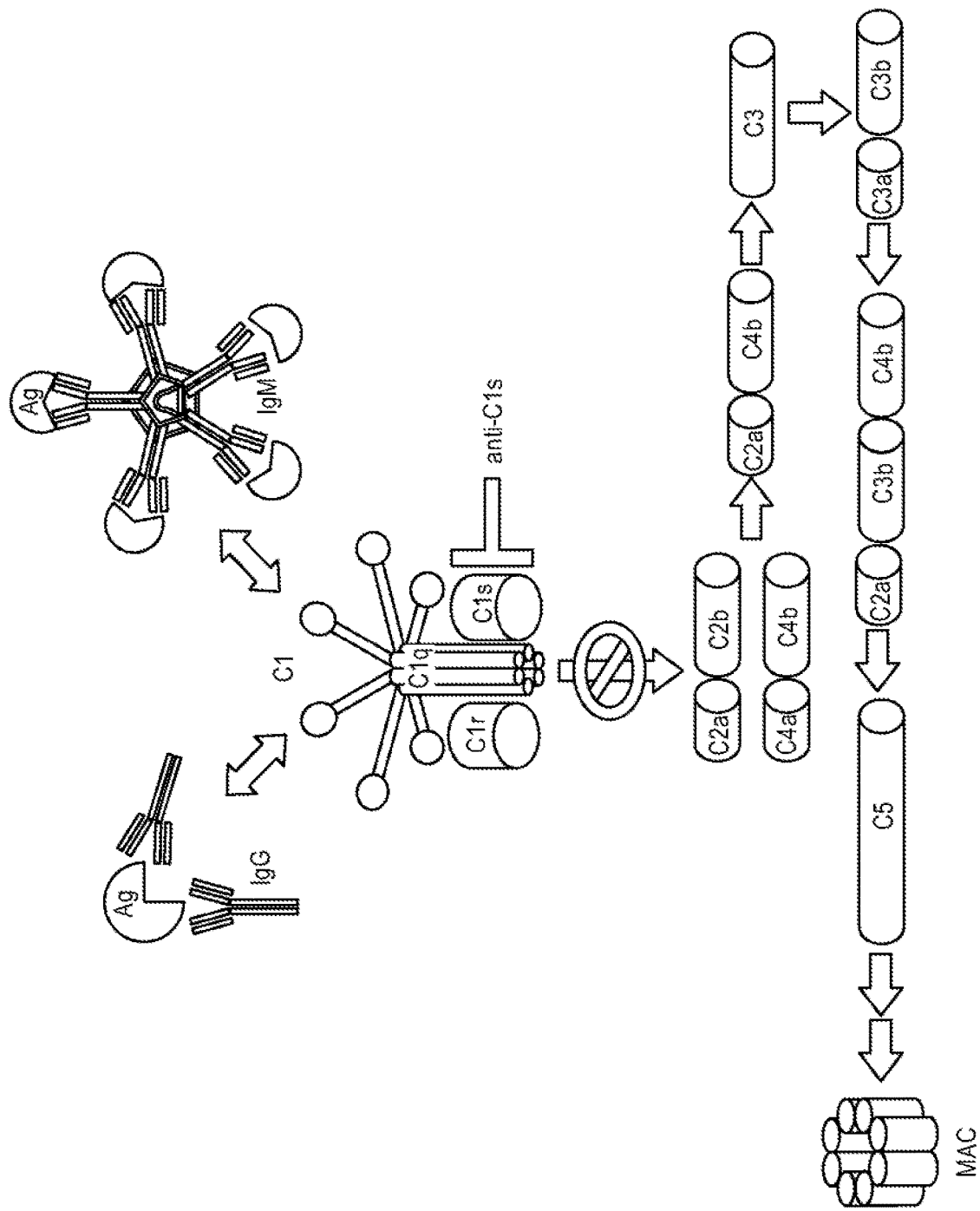
FIG. 1 shows a schematic of the CP and proposed action of anti-C1s antibody, where Ag indicates antigen, IgG and IgM indicate antibody types that might bind Ag, C1 indicates the C1 complex wherein C1q, C1r, and C1s indicate subcomponent proteins of the C1 complex, anti-C1s indicates anti-C1s antibody binding to C1s, labels C2a, C2b, C3 C3a, C3b, C4a, C4b, and C5 indicate components of the CP cascade arranged in a schematic of steps in the cascade, and MAC indicates the membrane attack complex.

The invention relates to novel antibodies and antigen-binding fragments thereof that bind C1s, and methods of making and using the same.

Terminology/Definitions

Scientific and technical terms used in connection with the present invention shall have the meanings that are commonly understood by those of ordinary skill in the art, unless otherwise defined. Use of singular terms ("a" or "an" or "the" or other use of a term in the singular) include plural reference, and plural terms shall include the singular, unless the context clearly dictates otherwise. Thus, for example, reference to "an antibody" includes "one or more" antibodies or a "plurality" of such antibodies. All publications mentioned herein are hereby incorporated by reference in their entirety.

Generally, nomenclature and techniques of molecular biology, microbiology, cell and tissue culture, protein and nucleotide chemistry, and recombinant DNA techniques available to one of skill of the art can be employed for the antibodies, antigen-binding fragments, compositions, and methods disclosed herein. Techniques and procedures described herein are generally performed according to conventional methods well known in the art and as described in various general and more specific references, inter alia. Sambrook et al. (1989) MOLECULAR CLONING: A LABORATORY MANUAL (2nd ed., Cold Spring Harbor Laboratory Press, Cold Spring Harbor, N.Y.) and Ausubel et al. (1994) CURRENT PROTOCOLS IN MOLECULAR BIOLOGY, Volumes I-III (John Wiley & Sons, N.Y.). Enzymatic reactions and purification techniques are performed according to manufacturer's specifications or as commonly accomplished in the art or as described herein, unless otherwise specified herein. Techniques and methods for pharmaceutical preparation and formulation, and treatment of subjects, are described herein using conventional nomenclature.

"Antibody" refers in the broadest sense to a polypeptide or combination of polypeptides that recognizes and binds to an antigen through one or more immunoglobulin variable regions, where the immunoglobulin variable regions may be naturally occurring or non-naturally occurring, e.g., as a result of engineering, chimerization, humanization, optimization, CDR-grafting, or affinity maturation.

An "antibody" as disclosed herein can be a whole (intact, full length) antibody, a single chain antibody, or an antigen binding fragment with one or two chains, and can be naturally occurring and non-naturally occurring. An antibody comprises at least sufficient complementarity determining regions (CDR), interspersed with framework regions (FR), for the antibody to recognize and bind to an antigen. An anti-C1s antibody disclosed herein may be, but is not limited to, at least one of a monoclonal antibody, a polyclonal antibody, a humanized antibody, a chimeric antibody, a single chain antibody, a Fab fragment, a single-chain variable fragment (scFv), an aptamer, a single-domain antibody (VHH, nanobody, camelid antibody), a recombinant antibody, a modified antibody having peptide/other moieties attached to antibody and/or additional amino acids added the N- or C-terminus, or other C1s-binding fragment or variant. Whole antibody, full length antibody, intact antibody, naturally occurring antibody, or equivalent terms are understood to refer to a polypeptide, in particular a glycoprotein, comprising in its canonical form with at least two heavy chains (HCs) and two light chains (LCs) interconnected by disulfide bonds. Each HC is comprised of a heavy chain variable region (VII) and an HC constant region (CH), and each light chain is comprised of a light chain variable region (VL) and an LC constant region (CL). The HC and LC variable regions, VH and VL, include a binding domain that interacts with an antigen. The VH and VL regions can be further subdivided into CDR regions characterized by hypervariability, interspersed with FR regions that are typically more conserved. Each VH and VL is typically composed of three CDRs and four FRs arranged from amino-terminus to carboxy-terminus in the following order FR1, CDR1, FR2, CDR2, FR3, CDR3, FR4. It is understood that the assignment of amino acids to each domain is in accordance with methods known in the art, in particular in accordance with the definitions found in, inter alia, SEQUENCES OF PROTEINS OF IMMUNOLOGICAL INTEREST, Kabat, et al.; National Institutes of Health, Bethesda, Md.; 5$^{th}$ ed., NIH Publ. No. 91-3242 (1991); Chothia, et al., (1987) *J Mol. Biol.* 196:901-917 or Chothia, et al., (1989) *Nature* 342:878-883. The constant regions of the antibodies may mediate the binding of the immunoglobulin to host tissues or factors, including various cells of the immune system and the classical complement system. Typically, an antibody comprises at least heavy chain (HC) CDR1, CDR2, and CDR3 and light chain (LC) CDR1, CDR2, and CDR3 sequences, where any one of these sequences may be naturally or non-naturally occurring. An antibody may comprise fewer CDR sequences, as long as the antibody can recognize and bind an antigen. Alternately, a whole antibody may be a single chain antibody such as a heavy-chain only isotype where antigen binding is mediated by one variable domain.

An anti-C1s antibody disclosed herein may be a variant comprising at least one altered CDR or framework sequence, wherein CDR and/or framework sequences may by optimized by mutating a nucleic acid molecule encoding such framework sequence. Variants may be constructed with HC and LC portions derived independently from different sources. Techniques for generating variants include but are not limited to conservative amino acid substitution, computer modeling, screening candidate polypeptides alone or in combinations, and codon optimization, and it is understood that a skilled person is capable of generating antibody variants as may be needed. An anti-C1s antibody disclosed herein may be a fragment. Antigen binding functions of an antibody can be performed by fragments such as: a Fab fragment; a monovalent fragment consisting of the VL, VH, CL and CHI domains; a F(ab)$_2$ fragment; a bivalent fragment comprising two Fab fragments linked by a disulfide bridge at the hinge region; an Fd fragment consisting of the VH and CHI domains; a single-chain variable fragment (scFv) consisting of the VL and VH domains of a single arm of an antibody; a single domain antibody (dAb) fragment which consists of a VH domain; and an isolated CDR (VHH, nanobody), or an aptamer. Antigen binding portions can be incorporated into single domain antibodies, maxibodies, minibodies, nanobodies, intrabodies, diabodies, triabodies, tetrabodies, v-NAR and bis-scFv (see, e.g., Hollinger and Hudson, 2005, *Nature Biotechnology*, 23(9): 1126-1136). Antigen binding portions of antibodies can be grafted into scaffolds based on polypeptides to form monobodies (see, e.g., U.S. Pat. No. 6,703,199, which describes fibronectin polypeptide monobodies).

The term antibody encompasses various broad classes of polypeptides that can be distinguished biochemically. The "class" of an antibody may refer to the type of constant domain or constant region possessed by its heavy chain. Those skilled in the art understand that there are five major classes of antibodies, viz., IgA, IgD, IgE, IgG, and IgM, and several of these may be further divided into subclasses (isotypes), e.g., IgG1, IgG2, IgG3, IgG4, IgA1, and IgA2, each of which is well characterized and known to confer functional specialization. Modified versions of each of these classes and isotypes are readily discernible and within the scope of the instant disclosure. All immunoglobulin classes are within the scope of the present disclosure.

The term "chimeric" antibody refers to an antibody in which a portion of the heavy chain (HC) and/or light chain (LC) involved in forming the immunoreactive site is derived from a particular source or species, while the remainder of the HC and/or LC is derived from a different source or species. In certain embodiments the target binding region or site will be from a non-human source (e.g., mouse or non-human primate) and the constant region is from human source.

As used herein, the phrase "humanized antibody" refers to an antibody (immunoglobulin) or antibody variant comprising portions of antibodies (immunoglobulins) comprising amino acid sequences of different origins, wherein at least one portion comprises amino acid sequences of human origin. A humanized antibody comprises a portion derived from a non-human antibody, typically from a mouse antibody that binds a target of interest, where the portion from non-human antibody may be an entire variable region from the "parental" non-human antibody or part of a variable region such as one or more CDRs from the "parental" non-human antibody. A humanized antibody may comprise one or more variable regions from a non-human antibody connected to an immunoglobulin framework of human origin, in particular to a human variable region framework. A humanized antibody may comprise CDRs from the parental, non-human antibody grafted (fused) in a framework comprising portions of variable regions derived from a human immunoglobulin framework, in particular an acceptor human framework or a human consensus framework. Techniques and principles for designing, making, and testing humanized antibodies are known (Jones P T, Dear P H. Foote J, Neuberger M S. Winter G. Replacing the complementarity-determining regions in a human antibody with those from a mouse. *Nature*. 1986, 321(6069):522-5; Almagro J C, Fransson J. Humanization of antibodies. *Front Biosci*. 2008, 13:1619-33). It is understood that changes can be made to one or more CDR sequences and/or to an acceptor framework at multiple locations in order to develop a humanized antibody having improved features according to the desired use, e.g., high affinity for target, specificity for selected epitopes, avoidance of unwanted events such as isomerization or deamination, low clearance, low toxicity, etc. An anti-C1s antibody disclosed herein may be a humanized variant.

"Binding" refers to a direct association between two molecules, due to, for example, covalent, electrostatic, hydrophobic, and ionic and/or hydrogen-bond interactions, including interactions such as salt bridges and water bridges. "Affinity" refers to the strength of the sum total of noncovalent interactions between a single binding site of a molecule (e.g., an antibody) and its binding partner (e.g., an antigen). Unless indicated otherwise, binding affinity as used herein refers to intrinsic binding affinity which reflects a 1:1 interaction between members of a binding pair (e.g., antibody and antigen). Affinity can be measured by common methods known in the art, including those described herein. The calculated concentration at which approximately 50% of maximal binding (the calculated $EC_{50}$) can be used as an estimate of affinity. The affinity of a molecule X for its partner Y can generally be represented by the dissociation constant (Kd or KD, representing $k_{off}/k_{on}$ measured for the interaction). "Specific binding" or "specifically binds" or "binds specifically" or similar terms refer to high-affinity binding, in particular binding with a measured affinity (Kd, KD) in at least the nanomolar range. An anti-C1s antibody of the present disclosure binds specifically to C1s protein.

"Substantially identical" as used to refer to a sequence substantially identical to an identified amino acid sequence or nucleotide sequence, is understood to be a sequence that is at least about 85%, 90%, 92%, 95%, 97%, or 98%, 99% identical to the amino acid or nucleotide sequence, determined as the percentage of residues in a candidate amino acid or nucleic acid sequence that is identical with the residues in the identified reference sequence after aligning the two sequences and introducing gaps, if necessary, to achieve the maximum percent identity. Methods and computer programs for the alignment are well known in the art, for example and publicly available computer software/programs such as Clustal Omega (from the European Molecular Biology Laboratory European Bioinformatics Institute (EMBL-EBI), available at https://www.ebi.ac.uk/Tools-/msa-clustalo-); when using such software/programs, the default parameters, e.g. for gap penalty and extension penalty, are preferably used A "subject" is a mammal, where mammals include but are not limited to primates (e.g., humans and non-human primates such as monkeys), domesticated animals (e.g., cows, sheep, cats, dogs, pigs, llamas, and horses), rabbits, and rodents (e.g., mice and rats). In certain embodiments, the subject is a human. The phrases "to a subject in need thereof" or "to a patient in need thereof" or "to a patient in need of treatment" or "a subject in need of treatment" may include subjects that would benefit from administration of the anti-C1s antibodies disclosed herein, for treatment of a complement-mediated disorder. It is understood that administration of anti-C1s antibodies encompasses administration to "a subject in need thereof" can be interpreted as referring to a subject known or suspected to have a complement-mediated disorder, such as ITP or NMO, based on indicators such as symptoms, family history, or genotype. It is further understood that anti-C1s antibodies can be administered to a subject that is not known or suspected to have a complement-mediated disorder, for purposes that may include but are not limited to, for preventative or prophylactic purposes, for screening, for diagnostics, for research purposes, or to achieve results distinct from treating a disorder.

An "effective amount" of an anti-C1s antibody, e.g., in a pharmaceutical formulation, refers to an amount effective, at dosages and for periods of time necessary, to achieve the desired therapeutic or prophylactic result. It is understood that "effective amount" is intended to refer to the amount of an anti-C1s antibody or a pharmaceutical composition comprising an anti-C1s antibody that will elicit the biological response of, or desired therapeutic effect on, a cell, a tissue, a system, a non-human animal subject, a non-human mammal subject, or a human subject that is being measured. The terms "therapeutically effective amount", "pharmacologically effective amount", and "physiologically effective amount" are used interchangeably to refer to the amount of an anti-C1s antibody that is needed to provide a threshold level of active antibody in the bloodstream or in the target tissue. The precise amount will depend upon numerous factors, e.g., the particular anti-C1s antibody (active agent), the components and physical characteristics of the composition, intended population of subjects/patients to be treated, considerations such as the disease state, age, sex, and weight of a subject, and the like, and can readily be determined by one skilled in the art, based upon the information provided herein or otherwise available in the relevant literature. The terms, "improve", "increase" or "reduce", as used in this context, indicate values or parameters relative to a baseline measurement, such as a measurement in the same subject prior to initiation of the treatment described herein, or a measurement in a control individual (or multiple control individuals) in the absence of the treatment described herein, or a value available in an information source such as a textbook, manual, or database.

The term "pharmaceutical composition" or "pharmaceutical formulation" refers to a preparation which is in such form as to permit the biological activity of an active ingredient contained therein to be effective, in particular an anti-C1s antibody as disclosed herein. It is understood that a pharmaceutical composition may contain more than one active ingredient, e.g., more than one anti-C1s antibody, or a combination of an anti-C1s antibody with another active ingredient that acts on a different target, where such combinations can be but are not limited to, a combination of an anti-C1s antibody with another active ingredient having a desired effect on other complement pathways or other processes involved in inflammation, a combination of an anti-C1s antibody with gene therapy agents, or a combination of an anti-C1s antibody with proteins (e.g., Fc-fusion proteins) against other targets. A "pharmaceutically acceptable carrier" refers to an ingredient in a pharmaceutical formulation, other than an active ingredient, which is nontoxic to a subject. It is understood that a pharmaceutically acceptable carrier can be, but is not limited to, a buffer, excipient, stabilizer, an adjuvant, or preservative.

The term "treat" or "treating" or similar terms as used herein, can refer to an outcome that is deemed beneficial for a particular subject in a defined set of circumstances. Treating a complement-mediated disorder may refer non-exclusively to any of reducing, ameliorating, slowing, interrupting, arresting, alleviating, stopping, or reversing the progression or severity of an existing symptom, disorder, condition, or disease, and may further encompass prevention or delay of the onset of one or more symptoms of a complement-mediated disorder, and/or lessening of the severity or frequency of one or more symptoms of a complement-mediated disorder. The terms "treating" or "method of treating" or equivalents can encompass one or more uses of anti-C1s antibodies disclosed herein, including but not limited to therapeutic, prophylactic, preventive, diagnostic, imaging, and screening uses.

The term "vector," as used herein, refers to a nucleic acid molecule capable of propagating a nucleic acid to which the vector sequence is linked, in a host cell in which the vector is introduced. Vectors capable of directing the expression of nucleic acids to which they are operatively linked are referred to herein as "expression vectors."

Anti-C1s Antibodies

Antibodies and antigen-binding fragments are provided that are capable of binding C1s and modulating the activity of C1s, thereby having the effect of modulating the activity of at least one component involved in at least one complement-mediated disorder, in particular at least one disorder associated with CP activation by autoantibodies bound to self-antigens. Antibodies and antigen-binding fragments are provided that are capable of binding C1s and modulating the activity of C1s, thereby having the effect of modulating the activity of at least one component of the CP involved in ITP and/or NMO. Anti-C1s antibodies that are capable of binding C1s and modulating the activity of C1s can be used in methods and compositions for treating complement-mediated disorders associated with CP activation by autoantibodies bound to self-antigens, in particular ITP.

Once antibodies or fragments specific for C1s are provided, the desired biological activity of modulating the activity of C1s or having the effect of modulating at least one component involved in complement-mediated disorders can be tested by several methods known to the skilled person.

It is understood that "modulate" or "modulating" or similar terms as used herein can refer to one or more effects that can result when an anti-C1s antibody disclosed herein binds its target molecule C1s. "Modulating" and its equivalents can refer to different modes of action and effects depending on the component under consideration, i.e., modulating can refer to neutralizing, reversing, inhibiting, blocking, reducing, antagonizing, agonizing, amplifying, enhancing, or otherwise changing with the activity of at least one component involved in the complement system, in particular the CP. It is understood that "inhibit C1s" or "inhibiting C1s" or "inhibition of C1s" or "C1s inhibition" or similar terms as used herein, refer to inhibiting at least one activity or function of C1s involved the complement cascade, such that inhibiting C1s has downstream effects such as inhibiting the activation of enzymes involved in the complement cascade, the association or disassociation of molecules involved in the complement cascade, the production of downstream effectors that require C1s activation, or the degree of serum complement-induced lysis of antibody sensitized cells. It is understood "C1s inhibition" or similar terms as used herein do not require demonstration of the specific activity or function(s) of C1s that are inhibited when the present C1s antibodies bind to the C1s target molecule, as measurements showing inhibition of processes or effectors that are known to be downstream of C1s activation can be used as surrogate measurements or indicators of C1s activity or function, and thus, as indicators of inhibition of C1s activity or function. Accordingly, C1s antibodies capable of binding to and inhibiting C1s are antibodies capable of, inter alia, inhibiting the activity of the classical pathway (CP) of complement activation, inhibiting downstream effects of C1s activation, inhibiting IgM-induced deposition of C4 from serum, inhibiting antibody-antigen complex mediated C4 cleavage, inhibiting antibody-antigen complex mediated deposition of C4b, inhibiting formation of C3 convertase, inhibiting downstream effects of CP activation, usw.

It is understood that the term "component" can refer not only to target molecule C1s, but also to a downstream molecule, process, or pathway involved in complement-mediated effects downstream of C1s activation, in particular CP-mediated effects downstream of C1s activation. It is understood that by targeting C1s with anti-C1s antibodies, the CP can be selectively targeted, such that CP-mediated effects can be specifically or selectively inhibited. This effect of selective targeting of the CP is also understood to leave the alternative and lectin pathways intact to combat infection. It is understood that anti-C1s antibodies as disclosed herein can be used to therapeutically target antibody-antigen complex triggered CP activation and modulate the activity of the CP pursuant to antibody-antigen complex triggered CP activation. Anti-C is antibodies as disclosed herein can be used to therapeutically target at least one component involved in complement-mediated disorders, in particular to specifically target at least one component involved in CP-mediated disorders, in particular at least one component involved in CP-mediated autoimmune disorders, in particular at least one component involved in ITP and/or NMO. Without wishing to be bound by a particular mechanism of action, targeting C1s using anti-C1s antibodies as disclosed herein is understood to specifically inhibit CP mediated cell lysis, which underlies the autoimmune pathology that results in effects such as destruction of self platelets, red cells, or astrocytes. In certain embodiments, anti-C1s antibodies as disclosed herein can be used to inhibit the CP pathway in a dose-dependent manner. In certain embodiments, anti-C1s antibodies as disclosed herein can be used to inhibit the effects of antibody-antigen complex triggered CP activation in a dose-dependent manner.

In certain embodiments, anti-C1s antibodies as disclosed herein can be used to therapeutically target antibody-antigen complex triggered CP activation and modulate the activity of the CP downstream of antibody-antigen complex triggered CP activation. In particular, anti-C1s antibodies as disclosed herein can be used to therapeutically target antibody-antigen complex triggered CP activation and inhibit the activity of the CP downstream of antibody-antigen complex triggered CP activation.

Using anti-C1s antibodies as disclosed herein to therapeutically target at least one component involved in CP-mediated disorders is understood to allow precise modulation of the activity of the CP and downstream effects of CP activity. In particular, anti-C1s antibodies as disclosed herein to therapeutically target at least one component involved in CP-mediated disorders is understood to allow precise inhibition of the activity of the CP and downstream effects of CP activity.

Anti-C1s antibodies disclosed herein allow the development of treatments that can be tailored to each subject (e.g., dosage, frequency of administration), where they can be continued and discontinued with ease, and combined with other therapies. In certain strategic embodiments, anti-C1s antibodies disclosed herein can be combined with other therapies that may address multiple therapeutic targets and/or address deficits or undesirable effects of one of the therapies in the combination therapy.

Exemplary Embodiments of Anti-C1s Antibodies and Uses Thereof

Non-limiting exemplary embodiments of anti-C1s antibodies of the invention are presently disclosed, in particular in the Examples. Tables, and Figures.

Antibodies Capable of Specifically Binding C1s and Inhibiting C1s Function.

A functional cascade can be used to identify and characterize anti-C1s antibodies of the present invention, where a first step in the cascade involves screening C1s-challenged clones for antibodies capable of binding to C1s, followed by sequencing cognate variable regions, recombinantly expressing chimeric antibodies with VH and VL from mouse clones linked with human constant regions, purifying recombinant antibodies, and screening the antibodies using a functional assay.

As demonstrated by exemplary embodiments disclosed in Example 2, recombinant chimeric antibodies were obtained that were capable of modulating C1s functions, as measured by an assay for IgM-induced C4 deposition from serum. Exemplary recombinant chimeric anti-C1s antibodies were obtained that were capable of inhibiting C1s functions as measured by the ability to inhibit IgM-induced human C4 deposition from human serum, and the ability to inhibit IgM-induced cynomolgus monkey C4 deposition from cynomolgus monkey serum. Exemplary recombinant chimeric anti-C1s antibodies were obtained that were capable of inhibiting C1s functions in a dose-dependent manner.

Humanized Variants

Humanized antibodies comprising CDRs derived from a non-human source grafted into a human-derived antibody framework are expected to be non-immunogenic when administered to a human subject. As demonstrated by exemplary embodiments disclosed in Example 2, humanized anti-C1s antibody variants were successfully generated, tested, optimized, and selected. Humanization of the 2-7 and 2-8 antibodies yielded humanized anti-C1s antibody variants, with the antibodies identified as hz2-7(H1L2) and hz2-8(H1L2) having the highest in vitro activities. After initial design and testing, variants that showed desired antigen binding affinity and cross-reactivity were selected for further evaluation and development, including but not limited to modification of some parental CDR sequences to avoid potential unwanted events such as aspartate isomerization and asparagine deamidation, and selected modifications of framework sequences.

Anti-C1s Antibodies Having High Affinity for a Biologically Relevant Target

Exemplary anti-C1s antibodies showed high affinity for biologically appropriate targets. Anti-C1s antibodies showed high affinity binding to proenzyme (native) C1s protein and to active C1s protein. As demonstrated by exemplary embodiments of affinity measurements using multiple methods as disclosed in Examples 2 and 3 and illustrated in FIGS. 2 and 3, antibodies 2-7, 2-8, hz2-7(H1L2), hz2-8(H1 L2), hz2-8(H1 L2 G80A), and hz2-8(H1L2 G80A/T82A) exhibited favorable affinity characteristics.

Anti-C1s Antibodies Having Cross-Reactivity with Non-Human Targets

It is desirable for therapeutically useful antibodies or antibody fragments to have sufficient cross-reactivity with non-human targets (non-human homologues) from sources that would be relevant for further studies such as preclinical efficacy studies, animal models of disease, toxicology studies, etc., such that the antibodies or antibody fragments should recognize, e.g., a rat homologue and/or a primate homologue such as from cynomolgus monkey. As demonstrated by exemplary embodiments in functional screening assays disclosed in Example 2 and illustrated in FIG. 2, antibodies 2-7, 2-8, hz2-7(H1L2), hz2-8(H1L2), hz2-8 (H1L2 G80A), and hz2-8(H1L2 G80A/T82A) inhibited IgM-induced deposition of human C4 from human serum and IgM-induced deposition of cynomolgus monkey C4 from cynomolgus monkey serum, providing antibodies raised against human C1s that have functional cross-reactivity with cynomolgus monkey C1s in a cynomolgus monkey system. As demonstrated by exemplary embodiments of binding affinity measurements disclosed in Example 3 and illustrated in FIG. 3, antibodies 2-7, 2-8, hz2-7(H1L2), hz2-8(H1L2), and hz2-8(H1L2 G80A/T82A) show detectable binding and high affinity for human C1s and cynomolgus monkey C1s, while antibodies 2-8 and hz2-8(H1L2 G80A/T82A) also showed detectable binding and reasonably high affinity for rat C1s.

Anti-C1s Antibodies Capable of Selectively Inhibiting the Classical Pathway (CP)

For CP-mediated disorders, for example CP-mediated disorders triggered by complement-fixing autoantibodies bound to antigens, it is desirable to selectively inhibit the CP upstream of a step where the CP generates common complement system effectors, in particular C3 convertase. Selectively inhibiting the CP is understood to inhibit effects of antibody-antigen complex triggered CP activation while leaving the alternative and lectin complement pathways intact to combat infection. For CP-mediated disorders, selectively inhibiting the CP upstream of the step of C3 convertase generation is understood to selectively inhibit unwanted effects of CP activation associated with the disorder, while leaving the alternative and lectin complement pathways largely intact to combat infection. Anti-C1s antibodies of the invention have selective effects within the CP by inhibiting C1s (i.e., inhibiting at least one C1s activity or function), thereby acting upstream of the formation of common complement system effectors.

As demonstrated by exemplary embodiments disclosed in Example 2, anti-C1s antibodies disclosed herein are capable of binding to C1s and inhibiting C is functions involved in IgM-induced C4 deposition from human serum and cynomolgus monkey serum, where it is understood inhibition of C4 deposition in the test assay indicates at least one of the following: C4 cleavage does not occur; C3 convertase formation is inhibited (prevented); and/or CP activation does not lead to downstream effects mediated by the common complement pathway effector C3. In particular, anti-C1s antibodies disclosed herein are capable of specifically binding to C1s and inhibiting at least one activity or function of C1s, such that IgM-induced C4 deposition from human serum and cynomolgus monkey serum is inhibited, C4 cleavage is inhibited, C3 convertase formation is inhibited (prevented), and CP activation is inhibited.

Figure 7A:
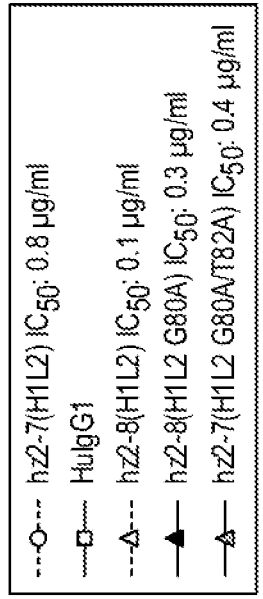
FIGS. 7A-7B show results for anti-C1s antibodies for the ability to inhibit complement-mediated lysis of antibody-sensitized sheep erythrocytes (EA cells). The effects of anti-C1s antibodies hz2-7(H L2), hz2-8(H1L2), hz2-8(H1L2 G80A) and hz2-8(H1L2 G80A/T82A), as well as an isotype control human IgG1, on normal human serum (NHS, FIG. 7A) or cynomolgus monkey serum (CMS, FIG. 7B) induced lysis of EA cells are shown. Symbols are used as follows: open circles represent results using an anti-C1s antibody hz2-7(1l1L2); open triangles represent results using an anti-C1s antibody hz2-8(H1L2); black filled triangles represent results using an anti-C1s antibody hz2-8(H1L2 G80A); triangles with diagonal lines represent results using an anti-C1s antibody hz2-8(H1L2 G80A/T82A), and open squares represent results using human IgG1.
Figure 7A:
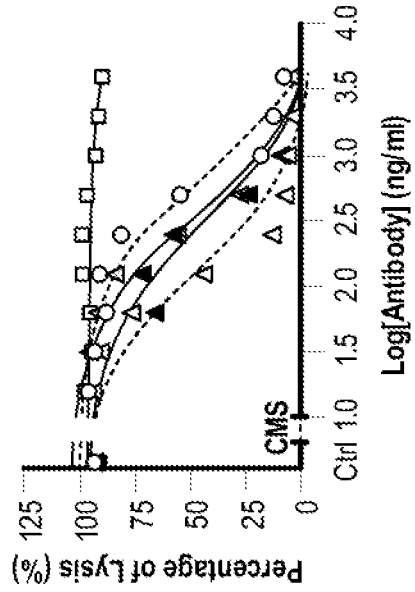
Figure 7B:
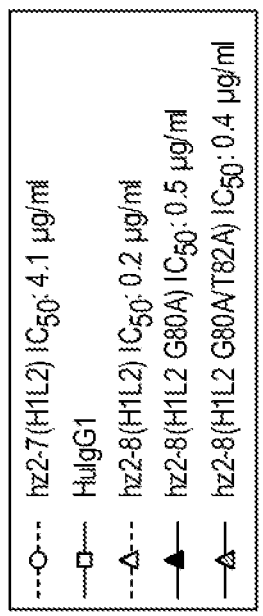
Figure 7B:
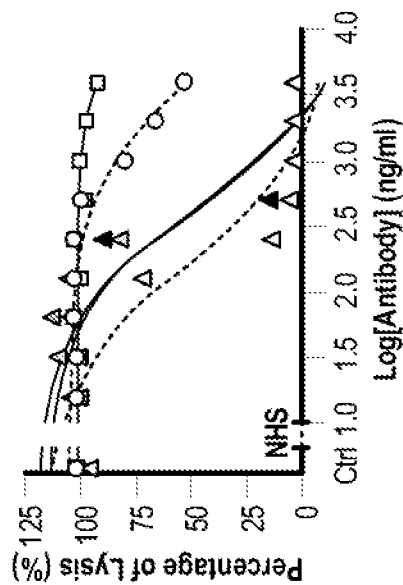

Exemplary embodiments disclosed in Example 7 demonstrate that anti-C1s antibodies disclosed herein are capable of modulating C1s functions involved in the complement classical pathway (CP). Sheep red blood cells coated with rabbit anti-sheep erythrocyte antiserum (hemolysin), also known as antibody-sensitized sheep erythrocytes ("EA" or "EA cells"), have traditionally been used to assay the activity of the complement classical pathway (CP) in serum samples. Commercially available EA cells (Complement Technology, #B202) and known assay systems were used to study complement-mediated lysis of EA in response to exposure to serum. Humanized anti-C1s antibodies hz2-7 (H1L2), hz2-8(H1L2), hz2-8(H1L2 G80A), and hz2-8 (H1L2 G80A/T82A) inhibited complement-mediated lysis of EA in a dose-dependent manner (Example 7, FIGS. 7A and 7B), where antibody hz2-8(H1L2) was the most potent inhibitor, hz2-8(H1L2), antibodies hz2-8(H1L1.2 G80A) and hz2-8(H1L1.2 G80A/T82A) were also highly effective inhibitors, and antibody hz2-7(H1L2) was less effective and showed species dependence.

Anti-C1s antibodies disclosed herein show different levels of inhibition under different conditions, e.g., using different antibodies under the same assay conditions, or using the same antibody under different assay conditions such as using serum from different species. Thus, anti-C1s antibodies disclosed herein provide tools and paths for investigating the roles of specific epitopes and binding interactions in the CP pathway.

Compositions

Compositions are provided that comprise the present anti-C1s antibody and pharmaceutically acceptable carrier (s) or excipient (s) suitable for the intended use(s) of each composition. Such carriers include but are not limited to: saline, buffer, glucose, water, glycerol, ethanol, excipient, stabilizer, preservative, or combinations thereof. It is understood that the pharmaceutical preparation should match the administration mode.

Anti-C1s antibodies disclosed herein can be administered by any suitable means, including but not limited to injection or parenteral administration. Parenteral administration can include intramuscular, intravenous, intraarterial, intraperitoneal, subcutaneous, intraspinal (including epidural or intrathecal), intraocular, intracerebral, intracerebroventricular, intracardiac, intradermic/intradermal, intraarticular, intralymphatic, or intraosseus administration. Anti-C1s antibodies disclosed herein can be formulated in compositions for introduction into the circulatory system by parenteral administration, in particular intravenous or intraarterial administration. Anti-C1s antibodies disclosed herein can be administered using a device, or as a depot, or in a sustained-release preparations (e.g., semipermeable matrices of solid hydrophobic polymers containing the antibody, or microcapsules) to allow slow and/or measured and/or localized delivery. Anti-C1s antibodies disclosed herein can be formulated and administered using colloidal drug delivery systems (for example, liposomes, albumin microspheres, microemulsions, nano-particles and nano-capsules) or in macroemulsions.

Methods

Methods are provided for treating a complement-mediated disorder using an effective amount of an anti-C1s antibody disclosed herein. Without wishing to be bound by a particular mechanism of action, methods are provided for precise targeting and inhibition of C1s using anti-C1s antibodies disclosed herein, thereby allowing precise targeting of C1s to selectively modulate activity of the CP. Methods for precise targeting and inhibition of C1s can be methods for using routes of administration to target locations or systems involved in a disorder, methods for using timing of administration to target critical periods, and combinations of these methods. Methods are provided for treating a complement-mediated disorder wherein the CP is activated by complement-fixing autoantibodies bound to self-antigens, and wherein this activation of the CP results in deleterious effects on tissues bearing the self-antigen. Methods are provided for treating a disorder related to unwanted activation of the CP, wherein such methods use an effective amount of an anti-C1s antibody disclosed herein to selectively modulate the activity of CP processes such as C4 cleavage and deposition leading to unwanted attack and destruction of self-tissues. In particular, methods are provided for treating autoimmune conditions by inhibiting downstream effects of CP activation by complexes of complement-fixing autoantibodies bound to self-antigens on platelets.

Methods and compositions are provided for precise targeting and inhibition of C1s using routes of administration to target locations or systems involved in a disorder. Without wishing to be bound by a particular mechanism of action, methods and compositions are provided for treating a disorder characterized by unwanted, abnormal, inappropriate, or excessive CP activation in the circulatory system can be targeted by introducing anti-C1s antibodies into the circulatory system, e.g., by intravenous or intraarterial administration. Without wishing to be bound by a particular mechanism of action, methods and compositions are provided for treating a disorder characterized by unwanted, abnormal, inappropriate, or excessive CP activation in the central nervous system (CNS) can be targeted by introducing anti-C1s antibodies into one or more CNS tissues or structures by intraspinal (including epidural or intrathecal), intraocular, intracerebral, or intracerebroventricular administration. Without wishing to be bound by a particular mechanism of action, methods and compositions are provided for treating a disorder characterized by unwanted, abnormal, inappropriate, or excessive CP activation in one or more joints can be targeted by introducing anti-C1s antibodies into one or more joints by intraarticular administration.

Methods are provided to treat immune thrombocytopenic purpura (ITP) by precise targeting of C1s using an effective amount of an anti-C1s antibody disclosed herein. Compositions of anti-C1s antibodies disclosed here can be formulated for introduction into the circulatory system, e.g., for intravenous and/or intraarterial administration, and introduced by methods that allow targeting of and inhibition of C1s in the circulatory system. Without wishing to be bound by a particular mechanism of action, methods using anti-C1s antibodies disclosed herein can inhibit antibody-mediated removal of platelets by inhibiting the CP. Without wishing to be bound by a particular mechanism of action, methods using anti-C1s antibodies disclosed herein can inhibit C4 deposition on platelets that leads to unwanted platelet destruction. Methods provided herein allow precise targeting of C1s when the CP pathway has been activated by complement-fixing autoantibodies bound to self-antigens on platelets, wherein inhibition of C1s activity interrupts the CP pathway and prevents downstream effects including, but not limited to, inhibiting IgM-induced deposition of C4 from serum, inhibiting antibody-antigen complex mediated C4 cleavage; inhibiting antibody-antigen complex mediated deposition of C4b on platelets, platelet destruction, platelet elimination, thrombocytopenia, and bleeding disorders.

Methods are provided to treat immune neuromyelitis optica (NMO), by precise targeting of C1s using an effective amount of an anti-C1s antibody disclosed herein. Compositions of anti-C1s antibodies disclosed here can be formulated for targeted introduction into the CNS, in particular for intraspinal (e.g., epidural or intrathecal), or intracerebral/intracerebroventricular introduction, and introduced by methods that allow targeting of and inhibition of C1s in the CNS where complement-dependent cytotoxicity (CDC) may occur. Without wishing to be bound by a particular mechanism of action, methods using anti-C1s antibodies disclosed herein can inhibit complement-dependent cytotoxicity (CDC) triggered by autoantibody binding to self antigen, including but not limited to inhibiting antibody-antigen complex mediated C4 cleavage; inhibiting antibody-antigen complex mediated deposition of C4b on astrocytes, inhibiting downstream effects of antibody-antigen complex mediated CP activation, and inhibiting downstream inflammation leading to, e.g., oligo-dendrocyte and neuronal injury, and inflammatory demyelinating lesions in the CNS, particularly in the spinal cord and optic nerve.

Methods and compositions provided herein allow precise timing of treatments. Without wishing to be bound by a particular mechanism of action, anti-C1s antibodies disclosed herein can be administered during an acute phase of a disorder, to inhibit CP-mediated processes during an acute phase of the disorder. Without wishing to be bound by a particular mechanism of action, using anti-C1s antibodies to selectively inhibit CP-mediated processes during an acute phase of a disorder may interrupt an acute incident and/or prevent progression of the disorder, and later allow the CP to return to normal activity after anti-C1s antibodies have dissociated from C1s targets.

Methods and compositions provided herein allow precise targeting by timing and location of treatments. Without wishing to be bound by a particular mechanism of action, the timing of administration of anti-C1s antibodies disclosed herein can occur prior to (e.g., in response to an indicator of possible onset of an acute phase) or during an acute phase of a disorder to selectively inhibit CP-mediated processes during the acute phase without inhibiting the functioning of other complement pathways, and the route of administration can be selected to target specific tissues, systems, or structures involved in the disorder. Without wishing to be bound by a particular mechanism of action, using anti-C1s antibodies to inhibit CP-mediated processes prior to or during an acute phase of a disorder may prevent or interrupt an acute incident without inhibiting normal functioning of other complement pathways, and later allow the CP to return to normal activity after anti-C1s antibodies have dissociated from C1s targets.

Methods and compositions provided herein allow control of the amount of therapeutic agent present at one or more time points during treatment. Anti-C is antibodies disclosed herein can inhibit C1s activity, and selectively inhibit CP pathway activity, in a dose-dependent manner. Without wishing to be bound by a particular mechanism of action, the dose sufficient to ameliorate at least one biological effect or symptom of the disorder (the "effective amount") may depend on factors specific to a subject in need thereof, such that treatment may comprise determining the dose of anti-C1s antibody needed to constitute an effective amount for the subject to be treated and administering that effective amount of an anti-C1s antibody to the subject, where levels of the therapeutic agent (anti-C1 antibody) are expected to decline after treatment due to dissociation from C1s targets and clearance from blood.

Methods for treating a complement-mediated disorder as provided herein comprise administering an effective amount of an anti-C1s antibody disclosed herein to a subject in need thereof, wherein administration of the effective amount of anti-C1s antibody ameliorates at least one biological effect or symptom associated with the disorder. Methods for treating a complement-mediated disorder associated with autoantibody-triggered activation of the CP are provided wherein administration of an effective amount of an anti-C1s antibody disclosed herein to a subject in need thereof, inhibits the CP pathway and prevents downstream effects of unwanted CP activation.

The following examples are offered to illustrate, but not to limit, the claimed invention.

EXAMPLES

Example 1: Antibody Production and Identification of Antibodies that Bind C1s The production of novel monoclonal antibodies against C1s was carried out under contract by GenScript USA, Inc. (Piscataway, N.J.), utilizing in vivo rodent immunization and single B cell cloning technology. Active form of C1s protein (Complement Technology Inc., CompTech A 104 C1s Enzyme) was used as antigen to immunize BALB/cJ and SJL mice (The Jackson Laboratories). Sufficient plasma titers as determined by an enzyme-linked immunosorbent assay (ELISA) were obtained, which trigged immunization antibody recovery and screening activities. Secondary lymphoid organs were harvested for CD138 plasma cells enrichment, which were then loaded on BEACON& 14K chip (Berkeley Lights, Inc., Emeryville, CA) to screen for single B cells that secrete antibodies specifically bind to C1s antigen. Positive single B cell clones were selected and exported for subsequent variable domain sequencing and recombinant antibody expression. Full-length recombinant chimeric antibodies were obtained by expression in ExpiCHO cells using pcDNA3.4-VH-CH where VH is from a positive B cell clone (mouse) and CH is IgG1 (human), and pcDNA3.4-VL-CL where VL is from a positive B cell clone (mouse) and CL is kappa (human). Recombinantly expressed and purified antibodies were further screened for functional activities in an in vitro cell-free system. From the positive C1s-binding B cell clones that were obtained, 159 clones were successfully exported for antibody sequencing, and 39 clones were sequenced with one cognate pair of heavy chain and light chain. All 39 anti-C1s clones were recombinantly expressed and purified, and subjected to functional screening.

Example 2. Functional Screening of Anti-C1s Antibodies

Anti-C1s antibodies from all 39 anti-C1s clones were recombinantly expressed and purified, and then subjected to a functional screening assay to identify anti-C1s antibodies capable of inhibiting IgM-induced C4 deposition. Briefly, anti-C1s antibodies were incubated with serum in IgM-coated plates under conditions suitable for IgM-induced deposition of C4 from the serum, followed by detection of the amount of deposited C4. This functional assay is used as a surrogate assay for C1s activity in accordance with the functional model wherein C4 has to be cleaved by active C1s prior to C4b deposition (in particular, C4b deposition on target cells such as platelets), such that measuring the effects of anti-C1s antibodies on IgM-induced deposition of C4 from serum serves to report the effects on anti-C1s antibodies on C1s activity. This functional assay serves as a surrogate assay for C1s activity (C1s function. C1s biological activity) in antibody-antigen complex mediated CP activation and downstream effects of such CP activation (see FIG. 1). Anti-C1s antibodies capable of inhibiting IgM-induced C4 deposition were chosen for further investigation.

Figure 2B:
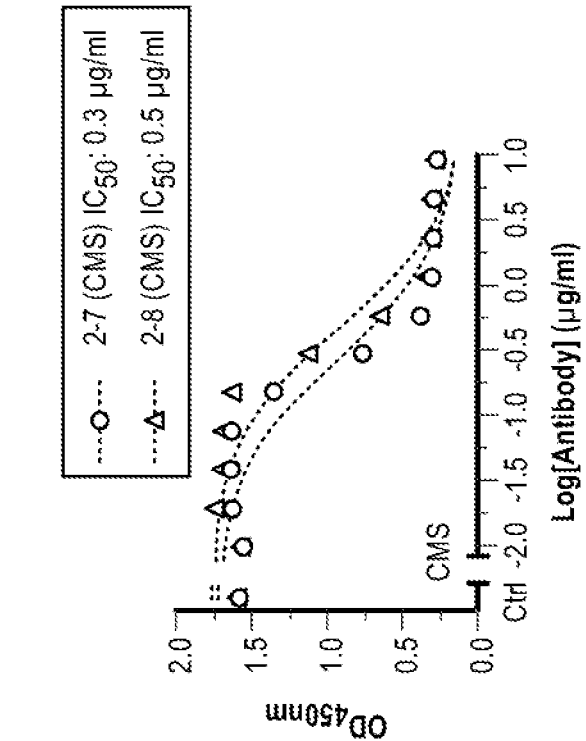
FIGS. 2A-2D show results for anti-C1s antibodies in a functional assay for the ability to inhibit IgM-induced deposition of C4 from serum.
Figure 2A:
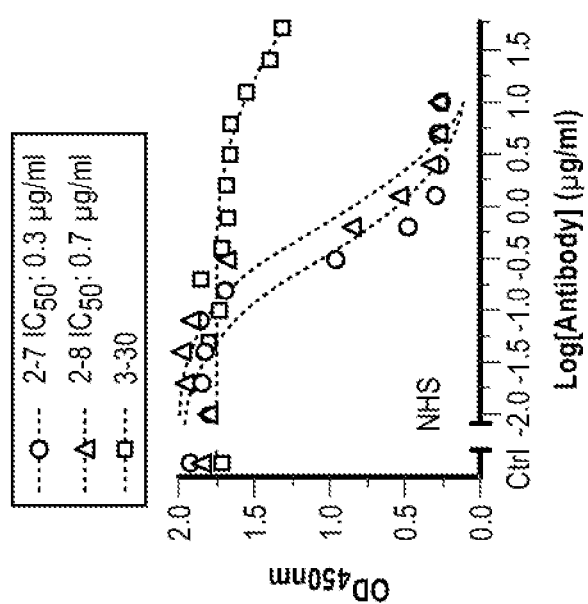

The functional screening was carried out by first coating 300 ng/well of IgM from human serum (Sigma-Aldrich 18260) in 96-well plates overnight. The next morning, plates were blocked with gelatin blocking buffer (1% in PBS, Alfa Aesar J62755) for 1 h before adding various concentrations of anti-C1s antibodies diluted in gelatin blocking buffer to each well. After a brief equilibration of anti-C1s antibodies by gentle shaking of the plates, NHS (normal human serum, CompTech NHS) were added to each well to make a final concentration of 1.25% (v/v). The plates were mixed well and incubated at 37° C. for 1 h to allow for C4 deposition induced by IgM. The plates were then washed extensively before incubating with goat anti-human C4 (CompTech A205) diluted in gelatin blocking buffer for 1 h. After incubation, the plates were washed again and incubated with rabbit anti-goat IgG (H+L) secondary antibody HRP conjugated (Invitrogen 81-1620) diluted in gelatin blocking buffer for 1h. At last, the plates were washed with PBS and color developed with ELISA liquid substrate (Sigma-Aldrich T4444), followed by stopping the reaction with addition of the same volume of ELISA liquid substrate of 1M $H_2SO_4$. Bound antibody was measured by absorbance at $OD_{450\,nm}$ to determine the amount of deposited C4. FIG. 2A shows the results for the top candidates, recombinant antibodies from clone 2-7 (designated anti-C1s antibody 2-7) and recombinant antibodies from clone 2-8 (designated anti-C1s antibody 2-8), as well as the results for antibodies from one of the non-functional clones (3-30) that bind C1s but do not demonstrably inhibit C1s function as measured in the functional assay. The half-maximal inhibitor concentration ($IC_{50}$) was determined for each antibody that showed an ability to inhibit IgM-induced C4 deposition, with $IC_{50}$ values for anti-C1s antibody 2-7 and anti-C1s antibody 2-8 between 0.3 and 0.7 µg/ml.

The functional screening assay as described above was repeated using normal cynomolgus monkey scrum (CMS, CompTech NCYS). FIG. 2B shows that anti-C1s antibodies 2-7 and 2-8 effectively inhibited IgM-induced deposition of cynomolgus monkey C4 as well, where anti-C1s antibody 2-7 has an $IC_{50}$ of approximately 0.3 µg/ml, and anti-C1s antibody 2-8 has an $IC_{50}$ of approximately 0.5 µg/ml.

Generation and Screening of Humanized Anti-C1s Antibody Variants

Humanization of the parental antibody was performed utilizing CDR grafting onto human antibody frameworks. Homology modeling of the parental antibody's 3-dimensional structure was first performed to establish a structural model of the parental antibody. Amino acid sequences for the variable fragment framework were identified based on the overall sequence identity, matching VH-VL interface positions, similarly classed CDR canonical positions (Kabat numbering), and removal of potential N-glycosylation sites. Humanized antibodies were designed by creating multiple hybrid sequences that fuse selected parts of the parental antibody sequence with the human framework sequences. The isotypes chosen to format humanized antibody were IgG1 for the heavy chain and IgG1 kappa for the light chain. Using the 3D model, these humanized sequences were methodically analyzed by eye and computer modeling to isolate the sequences that would most likely retain antigen binding. The goal was to maximize the amount of human sequence in the final humanized antibodies while retaining the original antibody specificity. Humanized variants, pairing the humanized VH and VL were then expressed using a pcDNA3.4-VL-CL-IRES-VH-CH vector in ExpiCHO cells, where IRES is "internal ribosome entry site" which allows expression of light chain and heavy chain simultaneously, were designed and constructed. Expressed recombinant humanized variants were then purified for affinity analysis.

In one round of designing, generating, and testing variants as part of an affinity analysis, three VH variants were generated with the VH-CDRs of the parental antibody in corresponding positions in three different human IgG1-derived frameworks, and three VL (VK) variants were generated with the VL-CDRs of the parental antibody in corresponding positions in three different human IgG1 kappa-derived frameworks. A total of nine (9) humanized variants representing every combination of the VH and VL (VK) variants were prepared according to a 3VH×3VK matrix, evaluated for antigen binding characteristics ($k_{on}$, $k_{off}$, KD).

Variants that showed desired antigen binding affinity based on cutoff values were selected for further evaluation and development. In some cases, parental CDR sequences were modified to avoid potential unwanted events such as aspartate isomerization or asparagine deamidation.

Figure 2D:
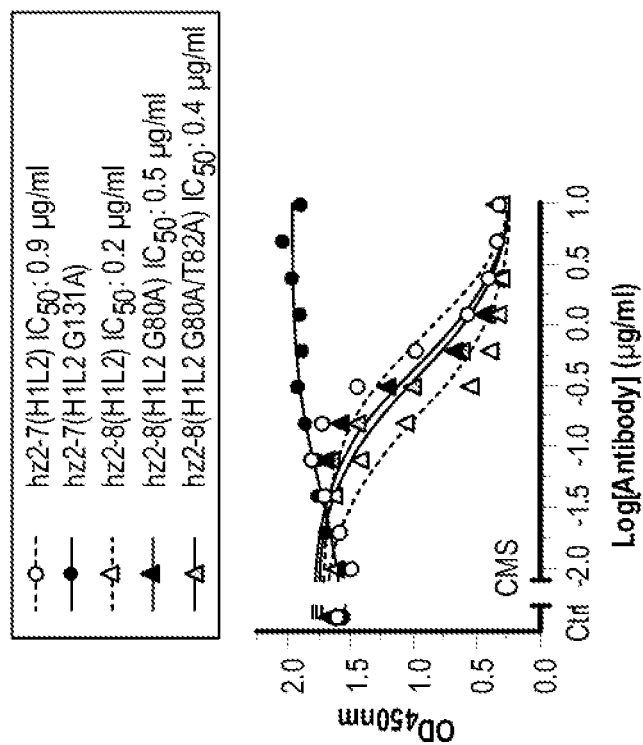
Figure 2C:
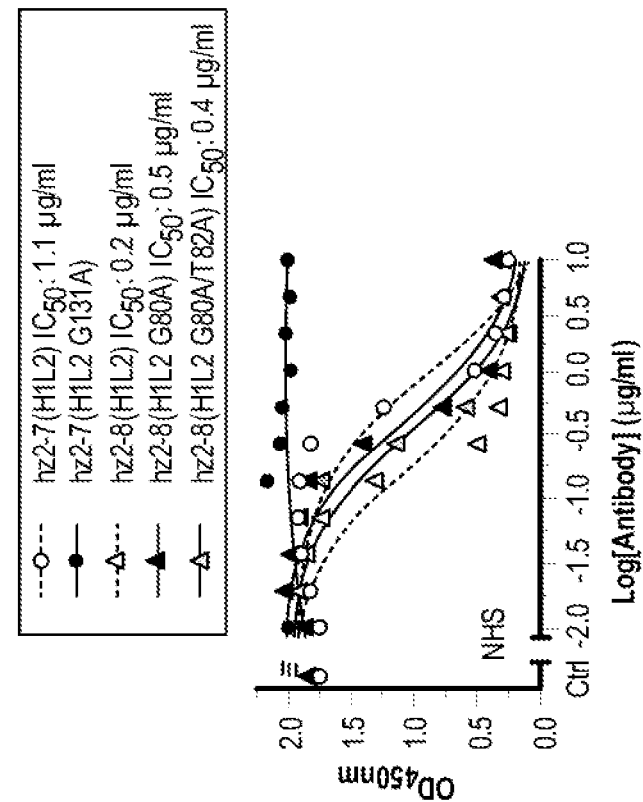

Humanized anti-C1s antibodies hz2-7(H1L2) and hz2-8 (H1L2) were chosen from among all the humanized variants tested, because of their superior capabilities of inhibiting IgM-induced C4 deposition from NHS and CMS (see FIGS. 2C and 2D). Comparison of $IC_{50}$ values shows that antibody hz2-7(H1L2) inhibited IgM-induced C4 deposition from NHS (FIG. 2D) and CMS (FIG. 2C) less effectively than its parental antibody 2-7 (FIG. 2A (NHS), FIG. 2B (CMS)), but antibody hz2-8(H1 L2) inhibited IgM-induced C4 deposition from NHS (FIG. 2C) and CMS (FIG. 2D) more effectively than its parental antibody 2-8 (FIG. 2A (NHS), FIG. 2B (CMS)).

FIG. 2C shows results for inhibition of IgM-induced C4 deposition from NHS by humanized antibodies hz2-7 (H1L2) and hz2-8(H1L2), and variants hz2-7(H1L2 G131A), hz2-8(H1L2 G80A), and hz2-8(H1L2 G80A/ T82A). The following $IC_{50}$ values were calculated for C1s-binding antibodies capable of inhibiting IgM-induced C4 deposition from NHS (FIG. 2C): $IC_{50}$ for hz2-7(H1L2) is 1.1 µg/ml; $IC_{50}$ for hz2-8(H1L2) is 0.2 µg/ml; $IC_{50}$ for hz2-8 (H1L2 G80A) is 0.5 µg/ml; and $IC_{50}$ for hz2-8(H1L2 G80A/ T82A) is 0.4 µg/ml. As shown in FIG. 2C, variant hz2-7 (H1L2 G131A) became functionally inactive after the mutation G131A was introduced, which is located within CDR3, so no $IC_{50}$ value was calculated for functionally inactive variant hz2-7(H1L2 G131A). Variants hz2-8(H1L2 G80A) and hz2-8(H1L2 G80A/T82A) were both functionally active although both were less effective than hz2-8 (H1L2) (FIG. 2C).

FIG. 2D shows results for inhibition of IgM-induced C4 deposition from CMS by humanized antibodies hz2-7 (H1L2) and hz2-8(111L2), and variants hz2-7(H1L2 G131A), hz2-8(H1L2 G80A) and hz2-8(H1L2 G80A/ T82A). Comparison of FIG. 2C and FIG. 2D shows that the same pattern of results was obtained when CMS (FIG. 2D) was utilized instead of NHS (FIG. 2C). The following $IC_{50}$ values were calculated for C1s-binding antibodies capable of inhibiting IgM-induced C4 deposition from CMS (FIG. 2D): $IC_{50}$ for hz2-7(H1L2) is 0.9 µg/ml; $IC_{50}$ for hz2-8 (H1L2) is 0.2 µg/ml; $IC_{50}$ for hz2-8(H1L2 G80A) is 0.5 µg/ml; and $IC_{50}$ for hz2-8(H1L2 G80A/T82A) is 0.4 µg/ml. No $IC_{50}$ value was calculated for functionally inactive variant hz2-7(H1L2 G131A).

Antibody hz2-8(H1L2 G80A/T82A), which has both aspartate isomerization and asparagine deamidation sites removed, was chosen for further development.

Table 1.a, below shows the SEQ ID NOs assigned to the heavy chain (HC) and light chain (LC) of each full-length antibody used in the Examples, and presents the VH amino acid sequence and SEQ ID NO: and VL amino acid sequence and SEQ ID NO: for each antibody, with CDRs indicated by underlining.

TABLE 1

Anti-C1s Antibodies
Table 1.a. Variable Regions of Anti-C1s Antibodies

```
Anti-C1s antibody 2-7 (HC SEQ ID NO: 71 and LC SEQ ID NO: 73)
HC variable region (VH) of 2-7 (CDRs indicated by underlining):
MYLGLNCVFIVFLLKGVQSEVKLEESGGGLVPPGGSMKLSCVASGFTFSNYFMNWVR
QSPEKGLEWVAEIRLKFTNYATHYAESVEGRFTISRDDSKSSVYLQMNNLRAEDTGIYY
CTRDYGSRNGYFDYWGQGTTLTVSS (SEQ ID NO: 1)
LC variable region (VL) of 2-7 (CDRs indicated by underlining):
MRCLAEFLGLLVLWIPGAIGDIVMTQAAPSVPVTPGESVSISCRSSKSLLHSNGNTFLYW
FLQRPGQSPQLLIYRMSNLASGVPDRFSGSGSGTAFTLRVSRVEAEDVGIYYCMQHLEY
PYTFGGGTKLEIK (SEQ ID NO: 6)

Anti-C1s antibody 2-8 (HC SEQ ID NO: 75 and LC SEQ ID NO: 77)
HC variable region (VH) of 2-8 (CDRs indicated by underlining):
MKCSWVIFFLMAVVTGVNSEVQLQQSGAELVRPGALVKLSCKASGFNIKEYYMHWV
KQRPEQGLEWIGWIDPENGDTIYDPKFQGKASITADTSSNTAYLQLSSLTSEDTAVYYC
ARSRLFFAYWGQGTLVTVSA (SEQ ID NO: 11)
LC variable region (VL) of 2-8 (CDRs indicated by underlining):
MESQIQVLVFVFLWLSGVDGDIVMTQSHKFMSTSVGDRVSFTCKASQDVRTAVDWYQ
QKPGQSPKLLIYSASYRYTGVPDRFTGTGSGTDFTFTISSVQAEDLAVYFCQQQYTTPYT
FGGGTKLEIK (SEQ ID NO: 16)

Anti-C1s antibody hz2-7(H1L2) (HC SEQ ID NO: 79 and LC SEQ ID NO: 81)
HC variable region (VH) of hz2-7(H1L2) (CDRs indicated by underlining):
MDPKGSLSWRILLFLSLAFELSYGEVQLLESGGGLVQPGGSLRLSCAASGFTFSNYFMN
WVRQAPGKGLEWVSEIRLKFTNYATHYADSVKGRFTISRDDSKSTLYLQMNSLRAEDT
AVYYCTRDYGSRNGYFDYWGQGTLVTVSS (SEQ ID NO: 21)
LC variable region (VL) of hz2-7(H1L2) (CDRs indicated by underlining)
METDTLLLWVLLLWVPGSTGDIVMTQTPLSLPVTPGEPASISCRSSKSLLHSNGNTFLY
WFLQKPGQSPQLLIYRMSNLASGVPDRFSGSGSGTDFTLKISRVEAEDVGVYYCMQHL
EYPYTFGGGTKLEIK SEQ ID NO: 26)

Anti-C1s antibody hz2-7(H1L2 G131A) (HC SEQ ID NO: 83 and LC SEQ ID NO: 85)
HC variable region (VH) of hz2-7(H1L2 G131A) (CDRs indicated by underlining;
```

TABLE 1-continued

Anti-C1s Antibodies
Table 1.a. Variable Regions of Anti-C1s Antibodies

CDR residues that differ from parental CDR sequence indicated in bold):
MDPKGSLSWRILLFLSLAFELSYGEVQLLESGGGLVQPGGSLRLSCAASG<u>FTFSNYFMN</u>
WVRQAPGKGLEWVS<u>EIRLKFTNYATHYADSV</u>KGRFTISRDDSKSTLYLQMNSLRAEDT
AVYYCTR<u>DYGSRNAYFDY</u>WGQGTLVTVSS (SEQ ID NO: 31)
LC variable region (VL) of hz2-7(H1L2 G131A):
Protein sequence of the VL (CDRs indicated by underlining):
METDTLLLWVLLLWVPGSTGDIVMTQTPLSLPVTPGEPASISC<u>RSSKSLLHSNGNTFLY</u>
WFLQKPGQSPQLLIY<u>RMSNLAS</u>GVPDRFSGSGSGTDFTLKISRVEAEDVGVYYC<u>MQHL</u>
<u>EYPYT</u>FGGGTKLEIK (SEQ ID NO: 36)

Anti-C1s antibody hz2-8(H1L2) (HC SEQ ID NO: 87 and LC SEQ ID NO: 89)
HC variable region (VH) of hz2-8(H1L2) (CDRs indicated by underlining):
MDPKGSLSWRILLFLSLAFELSYGQVQLVQSGAEVKKPGASVKVSCKASG<u>FNIKEYYM</u>
<u>H</u>WVRQAPEQGLEWMG<u>WIDPENGDTIYAQKFQG</u>RVTITADTSTNTAYMELSSLRSEDT
AVYYCAR<u>SRLFFAY</u>WGQGTLVTVSS (SEQ ID NO: 41)
LC variable region (VL) of hz2-8(H1L2) (CDRs indicated by underlining):
METDTLLLWVLLLWVPGSTGDIQMTQSPKSLSASVGDRVTITC<u>RASQDVRTALDWYQ</u>
QKPGQSPKLLIY<u>SASYRYS</u>GVPSRFSGSGSGTDFTLTISSLQPEDFATYYC<u>QQQYTTPYT</u>F
GQGTKLEIK (SEQ ID NO: 46)

Anti-C1s antibody hz2-8 (H1L2 G80A/T82A) (HC SEQ ID NO: 91 and LC SEQ ID
NO: 93)
HC variable region (VH) of hz2-8 (H1L2 G80A/T82A) (CDRs indicated by underlining:
CDR residues that differ from parental CDR sequence indicated in bold):
MDPKGSLSWRILLFLSLAFELSYGQVQLVQSGAEVKKPGASVKVSCKASG<u>FNIKEYYM</u>
<u>H</u>WVRQAPEQGLEWMG<u>WIDPENADAIYAQKFQG</u>RVTITADTSTNTAYMELSSLRSEDT
AVYYCAR<u>SRLFFAY</u>WGQGTLVTVSS (SEQ ID NO: 51)
LC variable region (VL) of hz2-8 (H1L2 G80A/T82A) (CDRs indicated by underlining):
METDTLLLWVLLLWVPGSTGDIQMTQSPKSLSASVGDRVTITC<u>RASQDVRTALDWYQ</u>
QKPGQSPKLLIY<u>SASYRYS</u>GVPSRFSGSGSGTDFTLTISSLQPEDFATYYC<u>QQQYTTPYT</u>F
GQGTKLEIK (SEQ ID NO: 56)

Anti-C1s antibody hz2-8 (H1L2 G80A) (HC SEQ ID NO: 95 and LC SEQ ID NO: 97)
HC variable region (VH) of hz2-8 (H1L2 G80A) (CDRs indicated by underlining: CDR
residues that differ from parental CDR sequence indicated in bold):
MDPKGSLSWRILLFLSLAFELSYGQVQLVQSGAEVKKPGASVKVSCKASG<u>FNIKEYYM</u>
<u>H</u>WVRQAPEQGLEWMG<u>WIDPENADTIYAQKFQG</u>RVTITADTSTNTAYMELSSLRSEDT
AVYYCAR<u>SRLFFAY</u>WGQGTLVTVSS (SEQ ID NO: 61)
LC variable region (VL) of hz2-8 (H1L2 G80A) (CDRs indicated by underlining):
METDTLLLWVLLLWVPGSTGDIQMTQSPKSLSASVGDRVTITC<u>RASQDVRTALDWYQ</u>
QKPGQSPKLLIY<u>SASYRYS</u>GVPSRFSGSGSGTDFTLTISSLQPEDFATYYC<u>QQQYTTPYT</u>F
GQGTKLEIK (SEQ ID NO: 66)

TABLE 1.b

Consensus CDR sequences

Consensus CDR sequences by alignment of:
Antibody 2-7; hz2-7(H1L2); and hz2-7(H1L2 G131A)

Consensus HC CDR-1: GFTFSNYFMN (SEQ ID NO: 129)

Consensus HC CDR-2: EIRLKFTNYATHYA(E/D)SV(E/K)G (SEQ ID NO: 130)

Consensus HC CDR-3: DYGSRN(G/A)YFDY (SEQ ID NO: 131)

Consensus LC CDR-1: RSSKSLLHSNGNTFLY (SEQ ID NO: 132)

Consensus LC CDR-2: RMSNLAS (SEQ ID NO: 133)

Consensus LC CDR-3: MQHLEYPYT (SEQ ID NO: 134)

Consensus CDR sequences by alignment of:
Antibody 2-8; hz2-8(H1L2); hz2-8(H1L2 G80A/T82A); and hz2-8(H1L2 G80A)

Consensus HC CDR-1: GFNIKEYYMH (SEQ ID NO: 135)

Consensus HC CDR-2: WIDPEN(G/A)D(T/A)IY(D/A)(P/Q)KFQG (SEQ ID NO: 136)

Consensus HC CDR-3: SRLFFAY (SEQ ID NO: 137)

Consensus LC CDR-1: (K/R)ASQDVRTA(V/L)D (SEQ ID NO: 138)

Consensus LC CDR-2: SASYRY(T/S) (SEQ ID NO: 139)

Consensus LC CDR-3: QQQYTTPYT (SEQ ID NO: 140)

Example 3. Binding Affinity of Anti-C1s Antibodies

Anti-C1s Antibody Affinity and Binding Kinetics: Measurements Using Bio-Layer Interferometry Bio-Layer Interferometry technology was used for anti-C1s antibody affinity measurement and binding kinetics determinations with OCTET® RED96e system (Sartorius AG). Pre-hydrated Anti-Human IgG Fc Capture (AHC) biosensors were first equilibrated in 1×KB (Kinetic Buffer, 1×PBS pH 7.4+0.02% Tween-20+0.1% BSA) for 120 sec for the first baseline, followed by loading with 10 mg/ml anti-C1s antibody (2-7, FIG. 3A; 2-8, FIG. 3B; hz2-7

Figures 3A, 3B:
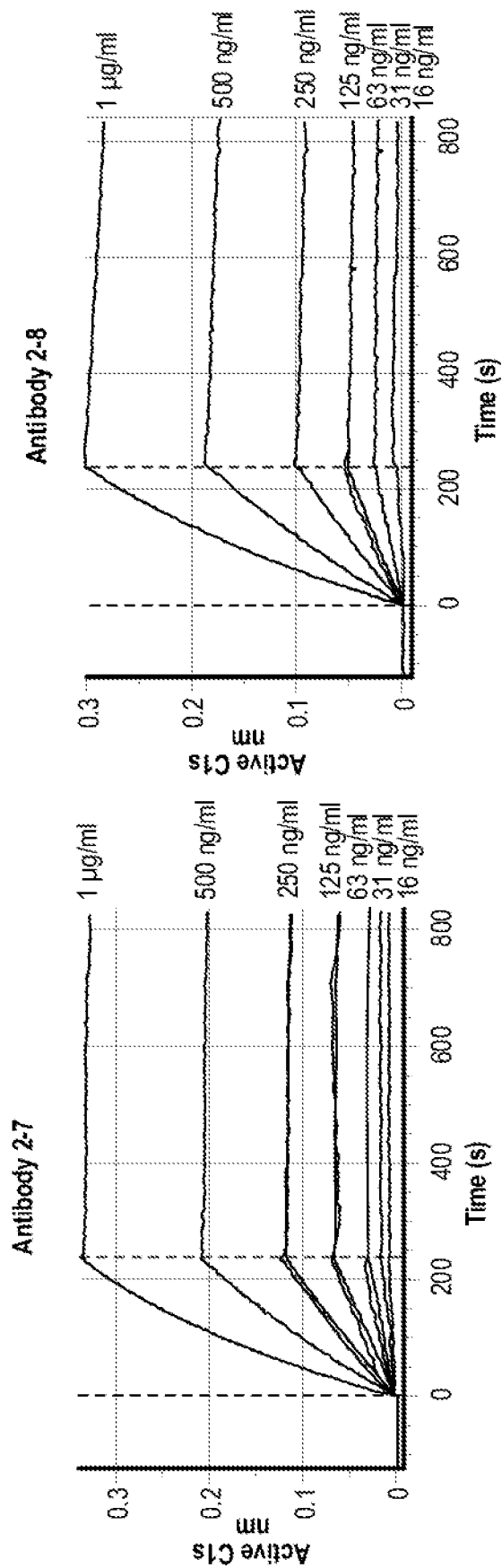
Figures 3C, 3D:
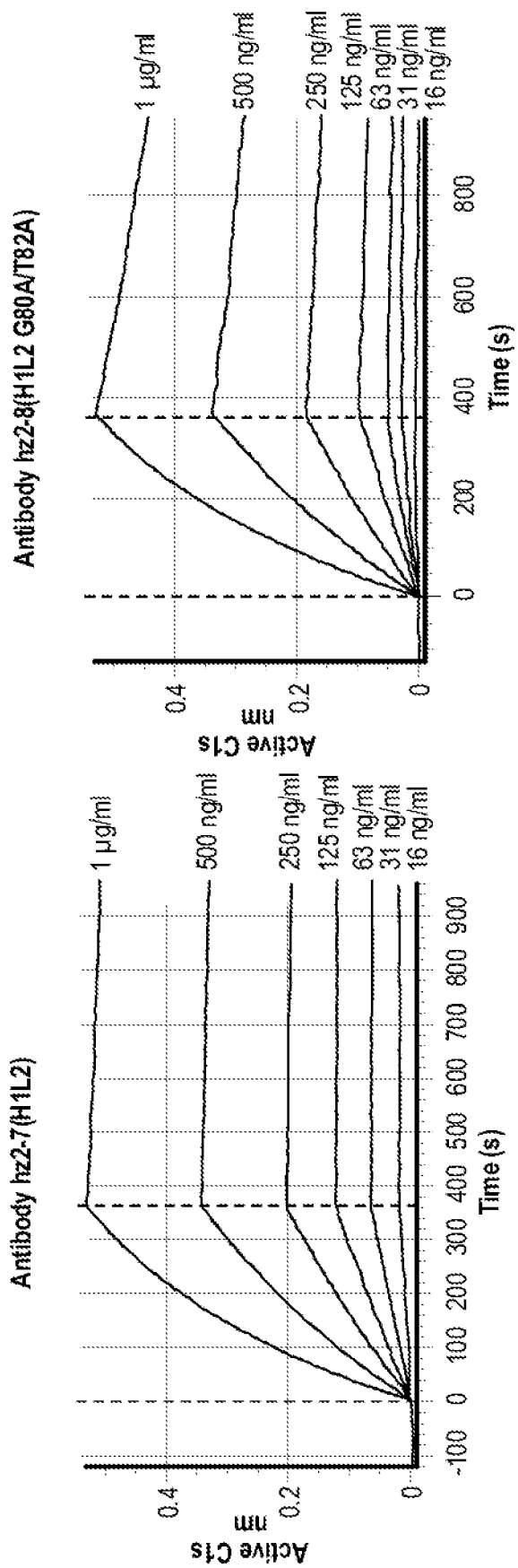

(H1L2), FIG. 3C; hz2-8(H1L2 G80A/T82A, FIG. 3D) onto AHC biosensors for 240 sec. Then, the second baseline signal was established for 120 sec before association with various concentrations of active human C1s (CompTech A104) for 240-360 sec. At last, analyte was dissociated in 1×KB for 360 sec. Anti-C1s antibodies 2-7 and 2-8 were also analyzed against human C1s proenzyme (CompTech A103) (data not shown). Data analysis was carried out using OCTET® Data Analysis HT Software (Sartorius AG). KD, $k_{on}$, $k_{off}$ and $R^2$ values were calculated for each antibody and target combination, as summarized in FIG. 3E showing high affinity binding with KD values in the low nanomolar to picomolar range. FIG. 3E further shows that anti-C1s antibodies 2-7 and 2-8 gave exactly the same calculated values for C1s proenzyme and active C1s protein, with $K_D$ values between 0.14 to 1.2 nM.

Anti-C1s Antibody Binding Affinity: Measurements Using ELISA

ELISA was carried out by first coating 96-well plates with 200 ng/well of human active C1s (CompTech A104, FIG. 3F) or human C1s proenzyme (CompTech A103, FIG. 3G) proteins overnight. The next morning, plates were blocked with SuperBlock T20 blocking buffer (Thermo Fisher Scientific Inc., Catalog No. 37536) for 1 h with gentle shaking. Then, various concentrations of anti-C1s antibodies diluted in SuperBlock T20 blocking buffer were added to the plates and incubated for 1 h with gentle shaking. Human IgG1 (BioXCell BP0297) was used as a negative control. The plates were washed before incubating with HRP conjugated secondary antibodies diluted in SuperBlock T20 blocking buffer (goat anti-human IgG antibody, HRP conjugate (Millipore AP309P)) for 1 h with gentle shaking. At last, the plates were washed and color developed with ELISA liquid substrate (Sigma-Aldrich), followed by stopping the reaction with addition of the same volume of ELISA liquid substrate of 1M $H_2SO_4$. Bound antibody was measured by absorbance at $OD_{450\ nm}$.

Figures 3F, 3G:
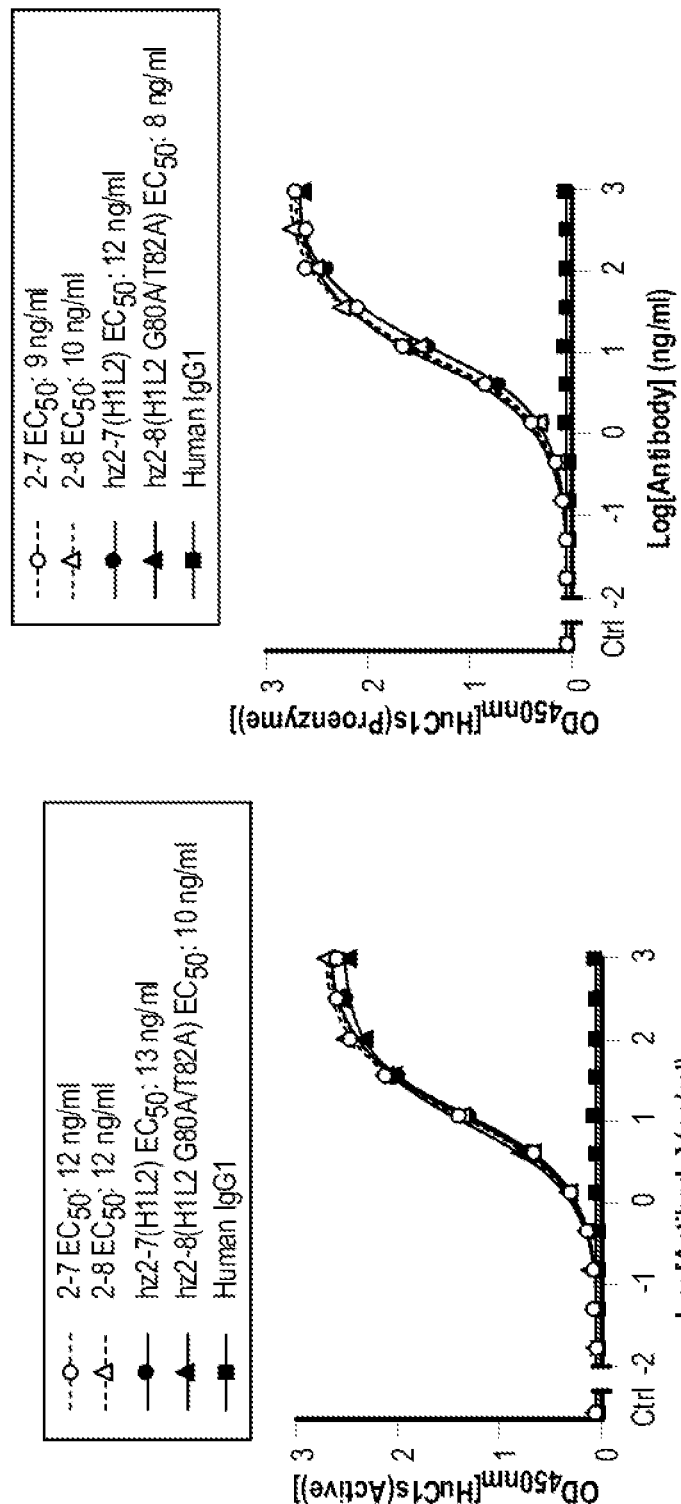
FIGS. 3F-3G show results for measurements of anti-C1s antibody binding to active and proenzyme forms of C1s using ELISA, where

FIG. 3F and FIG. 3G together demonstrate that top candidates 2-7 and 2-8, and their humanized variants hz2-7(H1L2) and hz2-8(H1L2 G80A/T82A), respectively, all showed strong binding to human active C1s (CompTech A104) (FIG. 3F) and human C1s proenzyme (CompTech A103) (FIG. 3G), with half maximal effective concentration ($EC_{50}$) values between 8 to 13 ng/ml. The $EC_{50}$ for each antibody and target combination was determined as follows: for antibody 2-7, $EC_{50}$ for human active C1s is 12 ng/ml and $EC_{50}$ for human C1s proenzyme is 9 ng/ml; for antibody 2-8, $EC_{50}$ for human active C1s is 12 ng/ml and $EC_{50}$ for human C1s proenzyme is 10 ng/ml; for variant hz2-7(1L2), $EC_{50}$ for human active C1s is 13 ng/ml and $EC_{50}$ for human C1s proenzyme is 12 ng/ml; and for variant hz2-8(H1L2 G80A/T82A), $EC_{50}$ for human active C1s is 10 ng/ml and $EC_{50}$ for human C1s proenzyme is 8 ng/ml. Control assays using human IgG1 at the same concentrations showed that these patterns did not reflect nonspecific binding (FIG. 3F-3G).

Anti-C1s Antibody Cross-Reactivity: Measurements Using Bio-Layer Interferometry

Figures 3H, 3I:
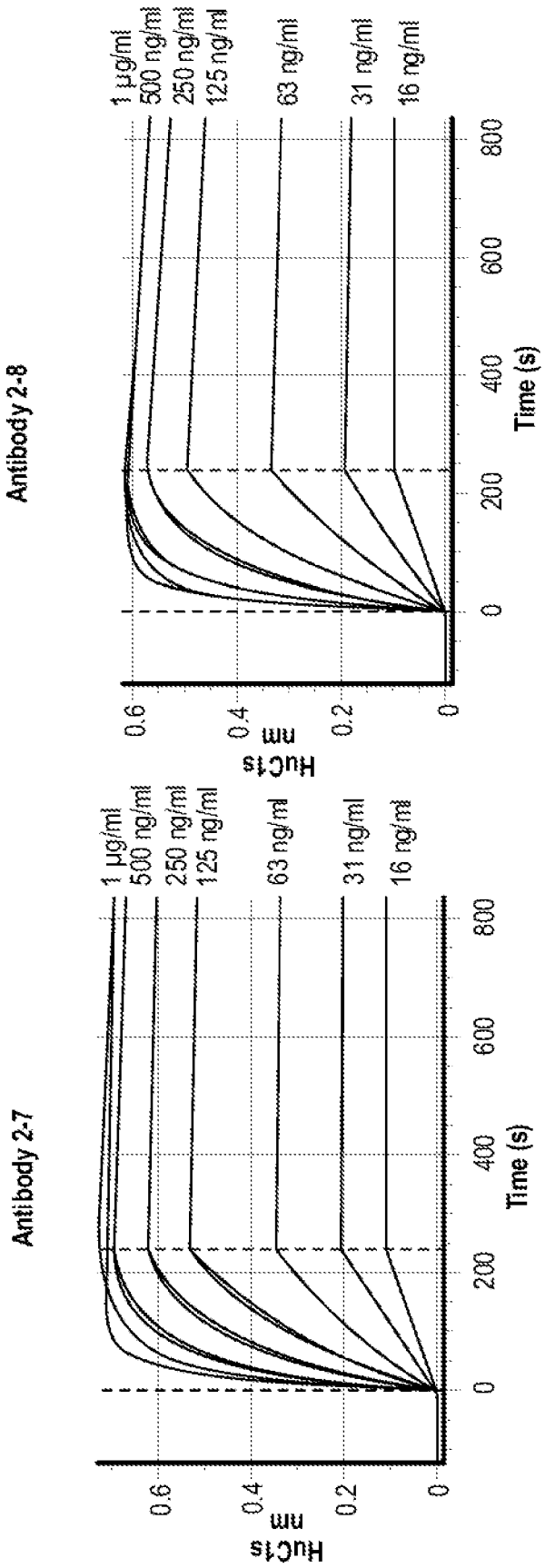
Figure 3M:
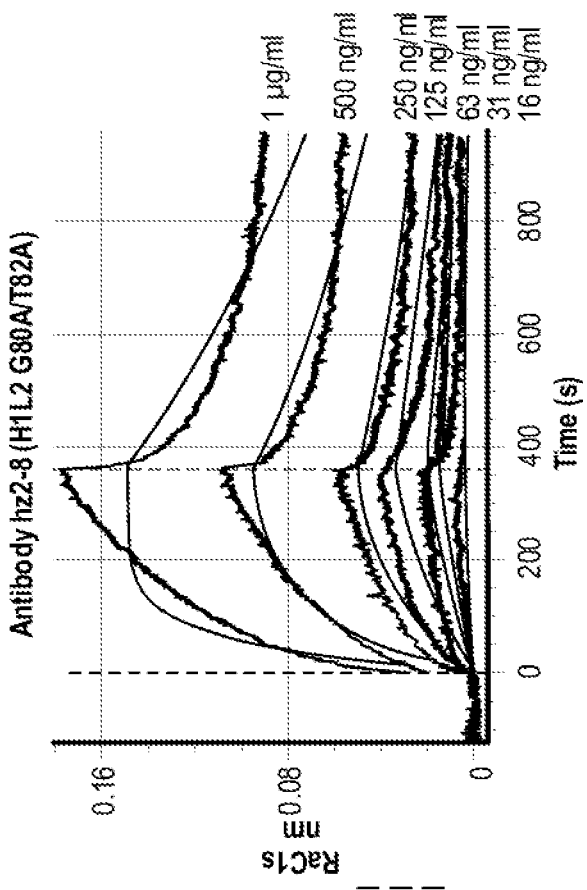
Figure 3L:
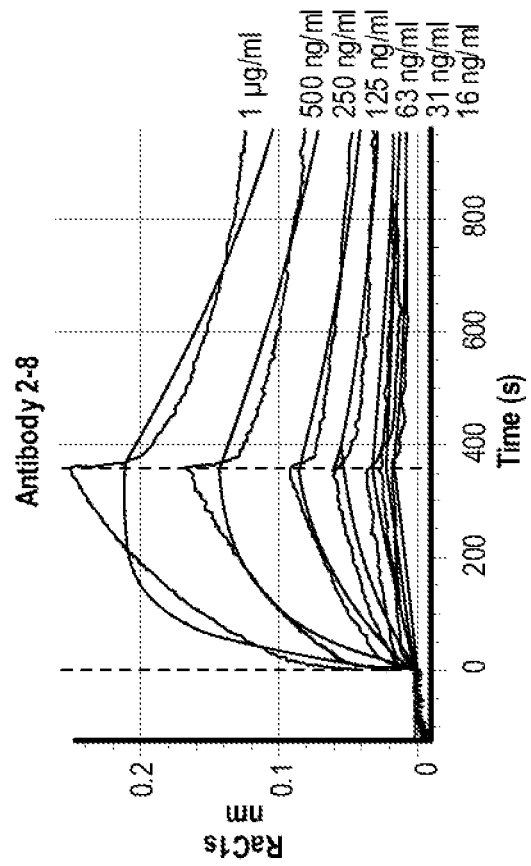
Figures 3N, 3O:
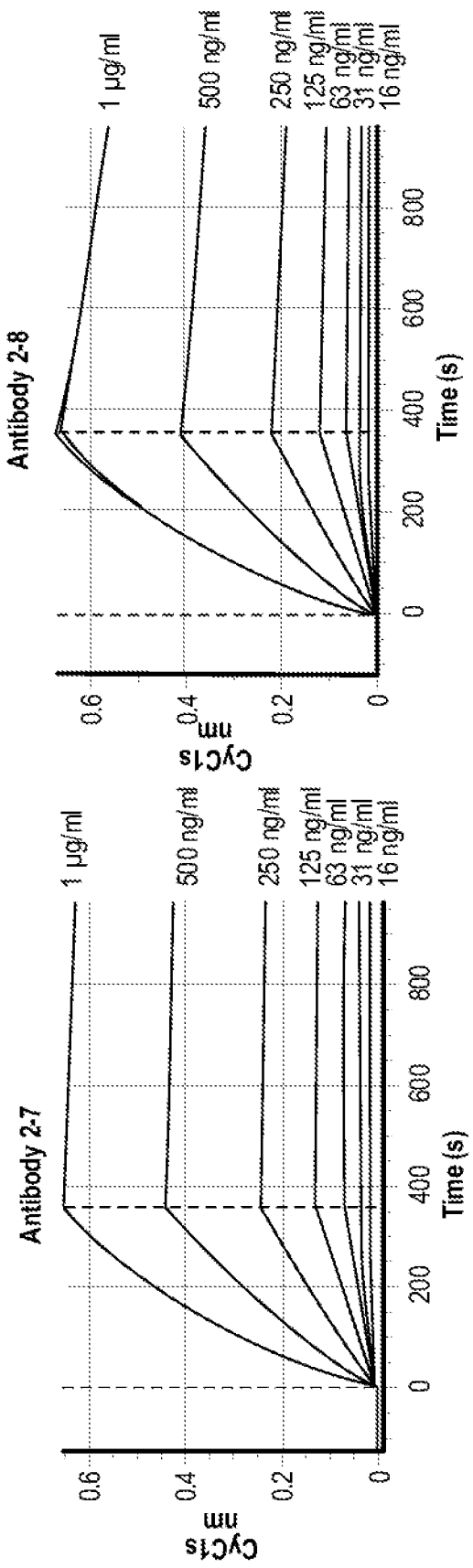
Figure 3Q:
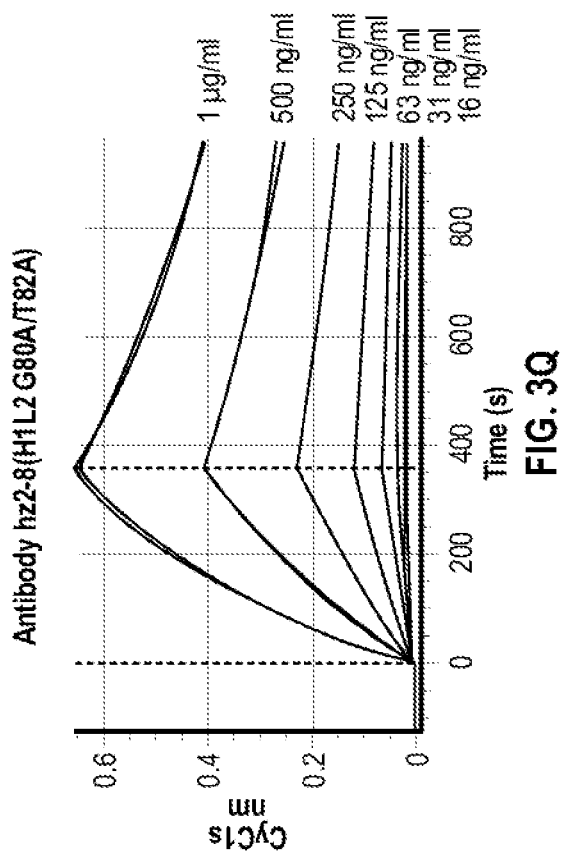
Figure 3P:
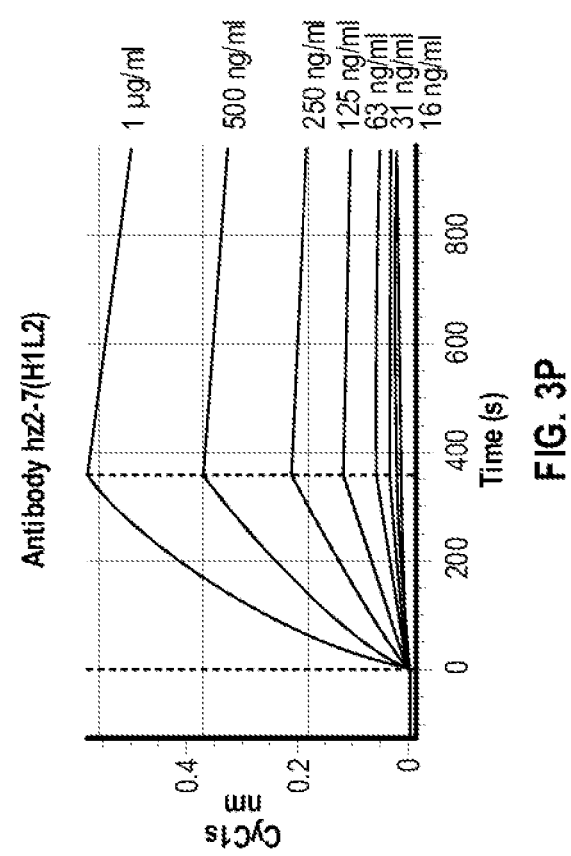

Pre-hydrated Anti-Human IgG Fc Capture (AHC) biosensors were first equilibrated in 1×KB (Kinetic Buffer, 1×PBS pH 7.4+0.02% Tween-20+0.1% BSA) for 120 sec for the first baseline, followed by loading with 10 mg/ml anti-C1s antibody (2-7, FIGS. 3H & N; 2-8, FIGS. 3I, L & O; hz2-7(H1L2), FIGS. 3J & P; hz2-8(H1L2 G80A/T82A, FIGS. 3K, M & Q) onto AHC biosensors for 240 sec. Then, the second baseline signal was established for 120 sec before association with various concentrations of human C1s (produced in house (SEQ ID NO: 99) shown in FIGS. 3H-K), rat C1s (produced in house (SEQ ID NO:105) shown in FIGS. 3L-M) or cynomolgus monkey C1s (produced in house (SEQ ID NO: 103) shown in FIGS. 3N-Q) for 240-360 sec. At last, analyte was dissociated in 1×KB for 360 sec. Data analysis was done using OCTET® Data Analysis HT Software (Sartorius AG). KD, $k_{on}$, $k_{off}$ and $R^2$ values were calculated for each antibody and target combination, as summarized in FIG. 3R. Top candidates 2-7 and 2-8, and their humanized variants hz2-7(H1L2) and hz2-8(H1L2 G80A/T82A), respectively, all showed strong binding to human C1s and cynomolgus monkey C1s, but no binding to mouse C1s (FIG. 3R) with $K_D$ between 0.012 to 3.5 nM. Anti-C1s antibody 2-7 and its humanized variant hz2-7 (H1L2) showed no binding to rat C1s, while 2-8 and its humanized variant hz2-8(H1L2 G80A/T82A) showed binding to rat C1s with $K_D$ values between 16 to 17 nM (FIG. 3R). The binding affinity of 2-8 and hz2-8(H1L2 G80A/T82A) for rat C1s was weaker than the binding affinity for human C1s and cynomolgus monkey C1s (FIG. 3R).

Anti-C1s Antibody Cross-Reactivity: Measurements Using EISA

Figure 3T:
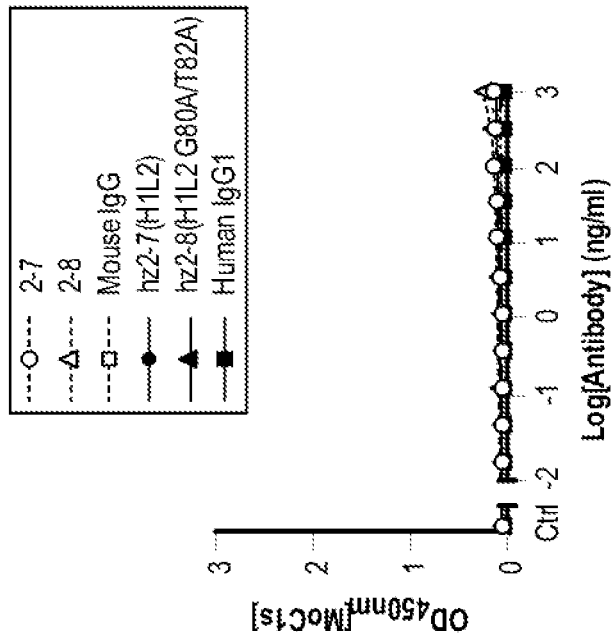
Figure 3S:
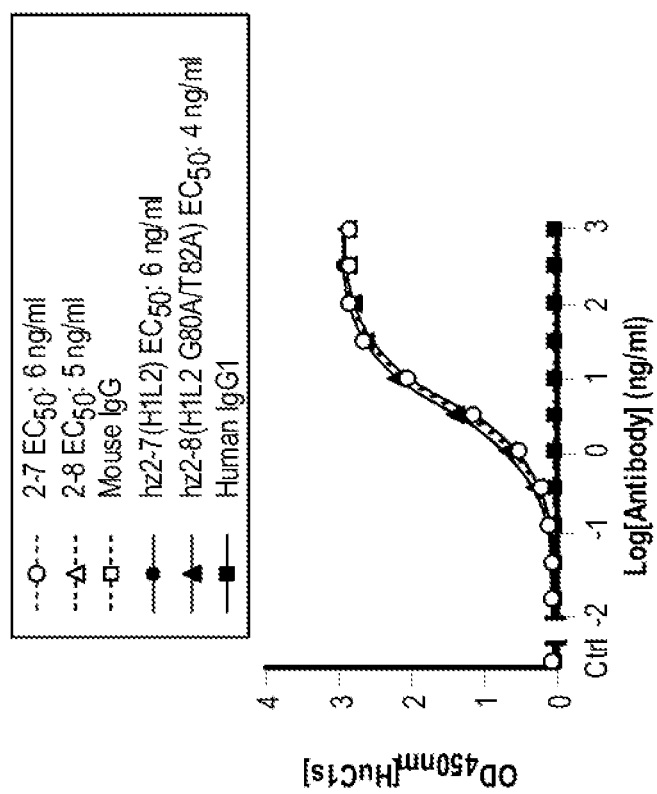
Figure 3V:
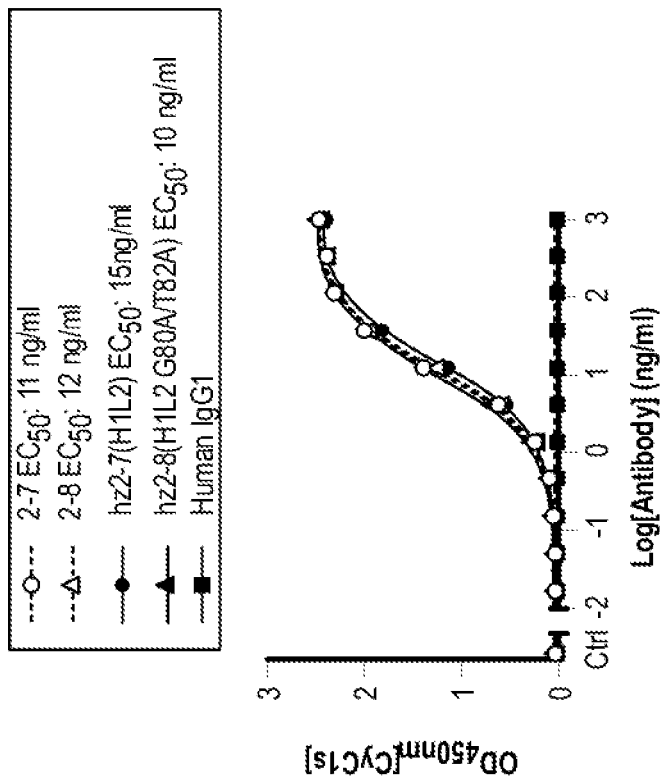
Figure 3U:
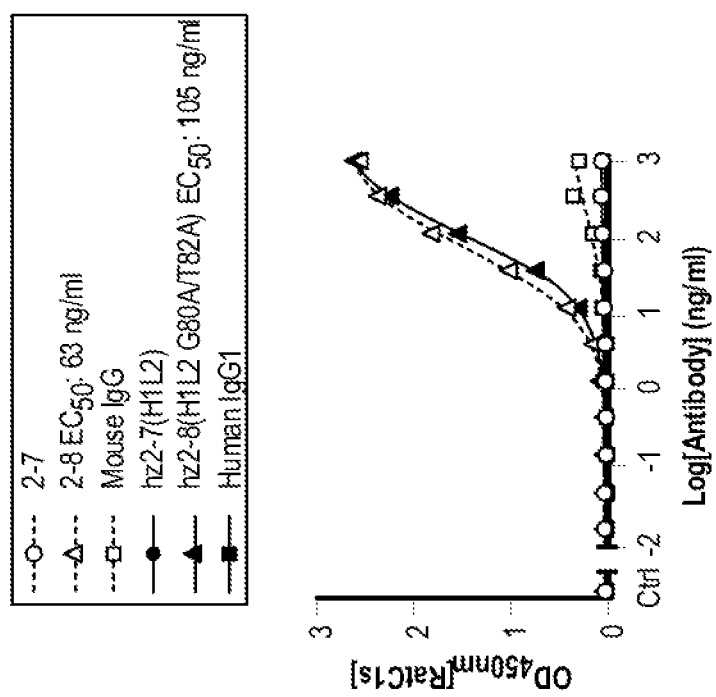

ELISA was carried out first by coating 96-well plates with 200 ng/well of human C1s (identified as full-length human C1s, HuC1s, wt human C1s)(produced in house (SEQ ID NO: 99), FIG. 3S), mouse C1s (produced in house (SEQ ID NO: 101), FIG. 3T), rat C1s (produced in house (SEQ ID NO: 105), FIG. 3U) or cynomolgus monkey C1s (produced in house (SEQ ID NO: 103). FIG. 3V) proteins overnight. The next morning, plates were blocked with SuperBlock T20 blocking buffer (Thermo Scientific 37536) for 1 h with gentle shaking. Then, various concentrations of anti-C1s antibodies diluted in SuperBlock T20 blocking buffer were added to the plates and incubated for 1 h with gentle shaking. Mouse IgG (Sigma-Aldrich I5381) and Human IgG1 (BioXCell BP0297) were used as negative controls. The plates were washed before incubating with HRP conjugated secondary antibodies diluted in SuperBlock T20 blocking buffer (goat anti-mouse IgG (H+L) cross-adsorbed secondary antibody HRP (Invitrogen G-21040) or goat anti-human IgG antibody, HRP conjugate (Millipore AP309P)) for 1 h with gentle shaking. At last, the plates were washed and color developed with ELISA liquid substrate (Sigma-Aldrich), followed by stopping the reaction with addition of the same volume of ELISA liquid substrate of 1M $H_2SO_4$. Bound antibody was measured by absorbance at $OD_{450\ nm}$. Top candidates 2-7 and 2-8, and their humanized variants hz2-7(H1L2) and hz2-8(H1L2 G80A/T82A), respectively, all showed strong binding to human C1s (FIG. 3S) and cynomolgus monkey C1s (FIG. 3V), but no binding to mouse C1s (FIG. 3T) with $EC_{50}$ between 4 to 15 ng/ml. Anti-C1s 2-7 and its humanized variant hz2-7(H1L2) showed no binding to rat C1s, while 2-8 and its humanized variant hz2-8(H1L2 G80A/T82A) showed weaker binding to rat C1s (FIG. 3U) with $EC_{50}$ between 63 to 105 ng/ml.

Example 4. Binding of Anti-C1s Antibodies to Full-Length and Truncated C1s Measured by ELISA Binding of anti-C1s antibodies to a full-length human C1s protein, a full-length mouse C1s protein, an NHC fragment of human C1s protein (FIG. 5B for alignment), and a middle fragment of human C1s located within the NHC (identified as "M151" or "huC1sM151"), encompassing 151 amino acids at residues 272 to 422 of human C1s, upstream of auto cleavage site R422-1423 (FIG. 5B for alignment), was measured by ELISA. Constructs were developed for expression of full length human C1s (Hu C1s, or "wt human C1s") (SEQ ID NO: 99), full length mouse C1s (moC1s) (SEQ ID NO: 101), human C1s deletion mutant 1 (huC1sM151) (SEQ ID NO: 107), and human C1s deletion mutant 2 corresponding to the NHC of C1s (huC1sNHC) (SEQ ID NO: 109), with a C-terminal 6×His tag on each expressed protein. All expression and purification of full-length and truncated C1s constructs (SEQ ID NOS: 100, 102, 108, 110) and resulting proteins (SEQ ID NOS: 99, 101, 107, 109) was performed in house.

Figure 4B:
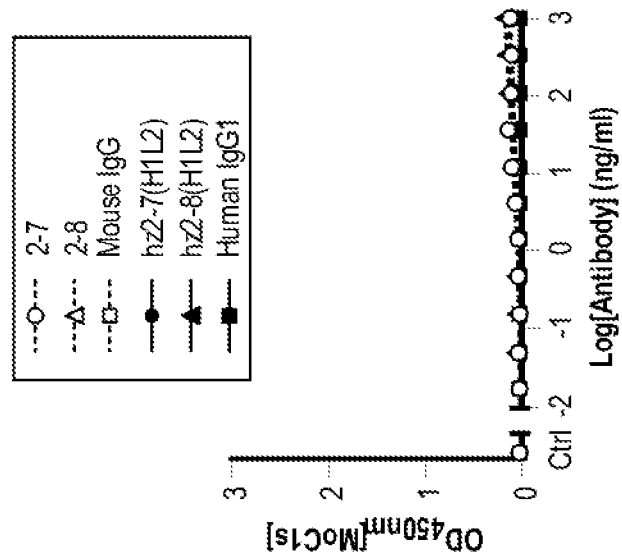
FIGS. 4A-4D show results for measurements of anti-C1s antibody binding to the full-length and different truncated forms of recombinant C1s using ELISA.
Figure 4A:
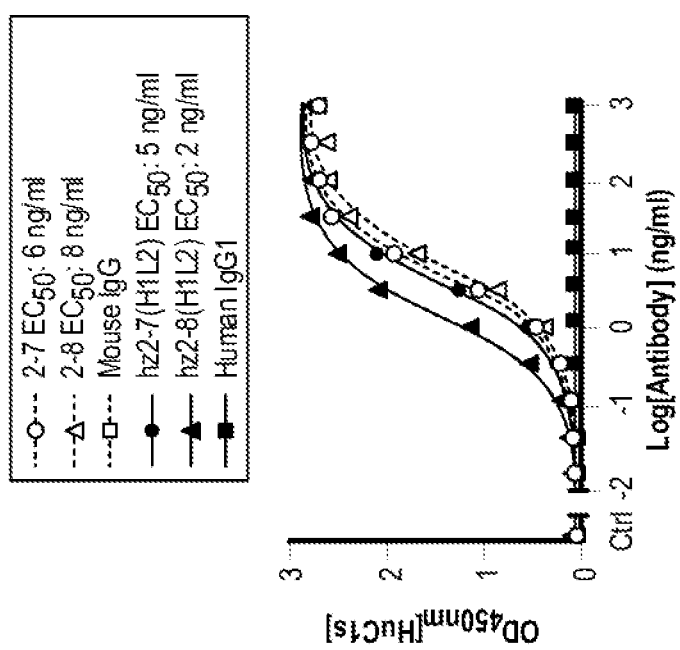
Figure 4D:
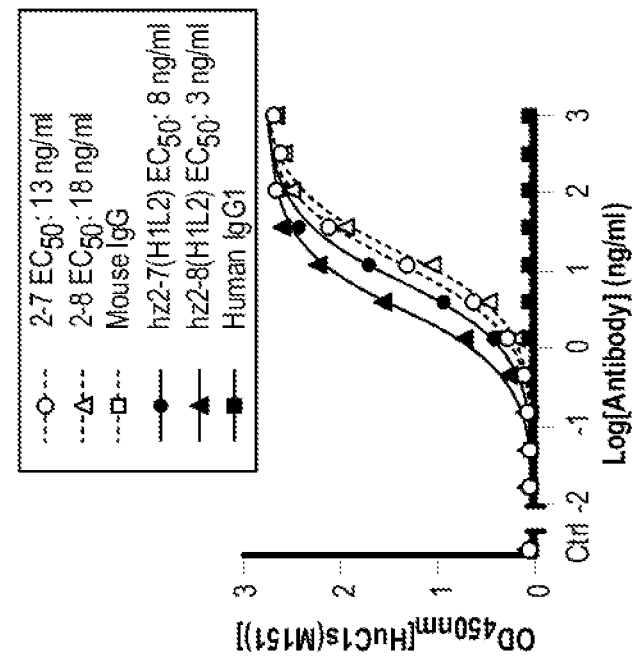
Figure 4C:
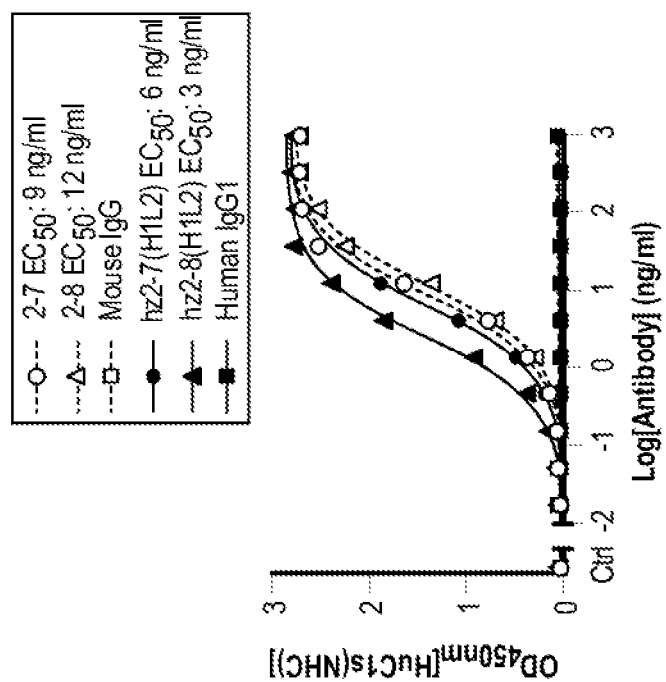

ELISA was carried out by first coating 96-well plates with 200 ng/well of full-length or truncated C1s proteins overnight. The next morning, plates were blocked with Super-Block T20 blocking buffer (Thermo Scientific 37536) for 1 h with gentle shaking. Then, various concentrations of anti-C1s antibodies diluted in SuperBlock T20 blocking buffer were added to the plates and incubated for 1 h with gentle shaking. Mouse IgG (Sigma-Aldrich 15381) and human IgG1 (BioXCell BP0297) were used as negative controls. The plates were washed before incubating with HRP conjugated secondary antibodies diluted in SuperBlock T20 blocking buffer (goat anti-mouse IgG (H+L) cross-adsorbed secondary antibody HRP (Invitrogen G-21040) or goat anti-human IgG antibody, HRP conjugate (Millipore AP309P)) for 1 h with gentle shaking. At last, the plates were washed and color developed with ELISA liquid HRP substrate (Sigma-Aldrich), followed by stopping the reaction with addition of 1M $H_2SO_4$ in the same volume as the ELISA liquid substrate. Bound antibody was measured by absorbance at $OD_{450\ nm}$. Results are shown in FIG. 4. Top candidates 2-7 and 2-8, and their humanized variants hz2-7(H1 L2) and hz2-8(H1L2), respectively, all showed strong binding to full-length human C1s (FIG. 4A) but no binding to full-length mouse C1s (FIG. 4B). All anti-C1s antibodies showed binding to both truncated human C1s (NHC and M151) with higher $EC_{50}$ compared to full-length C1s (FIGS. 4C-D), indicating that human C1s (M151) preserved the major binding sites for anti-C1s, and the flanking regions may facilitate holding the right (or preferred) conformation.

Example 5. Bending of Anti-C1s Antibodies to Full-Length and Truncated C1s Demonstrated by Western Blot Western blot analysis was first carried out by resolving 200 ng/lane full-length or truncated C1s (human C1s, mouse C1s, NHC of human C1s and M151 of human C1s) on SDS-PAGE with or without reducing agent (Invitrogen B0004), as follows: 200 ng full-length human C1s (HuC1s; SEQ ID NO:99) in lane 1, 200 ng full length mouse C1s (MoC1s; SEQ ID NO: 101) in lane 2, 200 ng truncated human C1s M151 (HuC1s(M151); SEQ ID NO:107) in lane 3, and 200 ng truncated human C1s NHC (HuC1s(NHC); SEQ ID NO: 109) in lane 4. The proteins were later transferred to nitrocellulose membranes, and blocked with 5% blotto (ChemCruz sc-2325) diluted in TBST (Teknova T1688) overnight. The next morning, the blocked membranes were first incubated with I pg/ml anti-C1s antibody diluted in 5% blotto-TBST for 1 h with gentle shaking. Then, the membranes were washed and incubated with HRP conjugated secondary antibodies diluted in 5% blotto-TBST (goat anti-human IgG antibody, HRP conjugate (Millipore AP309P)) for 1 h with gentle shaking. At last, membranes were washed extensively, and developed using SuperSignal West Dura Extended Duration Substrate (Thermo Scientific 34075) and imaged under azure biosystems. Representative results are shown in FIG. 5A presenting results for anti-C1s antibody 2-8.

Where the blot on the left is from the gel running under non-reducing conditions, and the blot on the right is from the gel running under reducing conditions. On the blot of the gel running without reducing agent (left), lane 1 shows antibody 2-8 binding to two (2) major bands of full-length human C1s (HuC1s) with the top band corresponding to the full-length HuC1s and the bottom band corresponding to the auto-cleaved heavy chain, lane 2 shows no detectable antibody 2-8 to full length mouse C1s (MoC1s), lane 3 shows antibody 2-8 binding to multiple bands of truncated human C1s M151 (HuC1s(M151)), and lane 4 shows antibody 2-8 binding to a few higher molecular weight bands of truncated human C1s NHC (HuC1s(NHC)). On the blot of the gel running with reducing agent (right), lane 1 shows a low level of antibody 2-8 binding to a band corresponding to the auto-cleaved heavy chain of the full-length human C1s (HuC1s), lane 2 shows no detectable antibody 2-8 to full length mouse C1s (MoC1s), lane 3 shows a low level of antibody 2-8 binding to the monomer of truncated human C1s M151 (HuC1s(M1S1)), and lane 4 shows a low level of antibody 2-8 binding to the monomer of truncated human C1s NHC (HuC1s(NHC)).

Figure 5A:
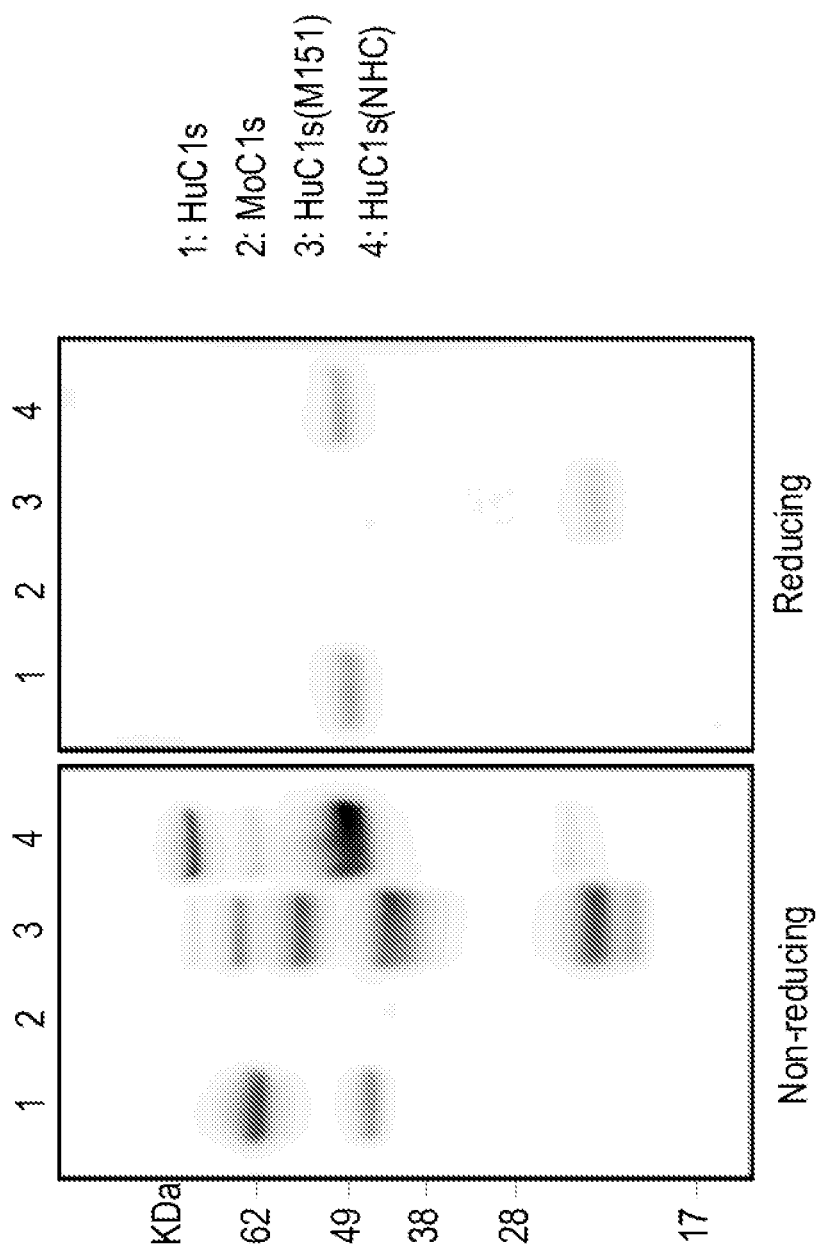
FIGS. 5A-5B show binding to and schematic comparison of full-length and truncated forms (including deletion mutants) of C1s.

Results using anti-C1s antibodies 2-7, hz2-7(H1L2), and hz2-8(H1L2)) showed the same binding pattern (data not shown) as the results for antibody 2-8 shown in FIG. 5A. These results showed that the binding site for anti-C1s antibody 2-7, anti-C1s antibody 2-8, anti-C1s antibody hz2-7(H1L2), and anti-C1s antibody hz2-8(H1L2) is within the human C1s M151 region on the NHC.

Figure 5B:
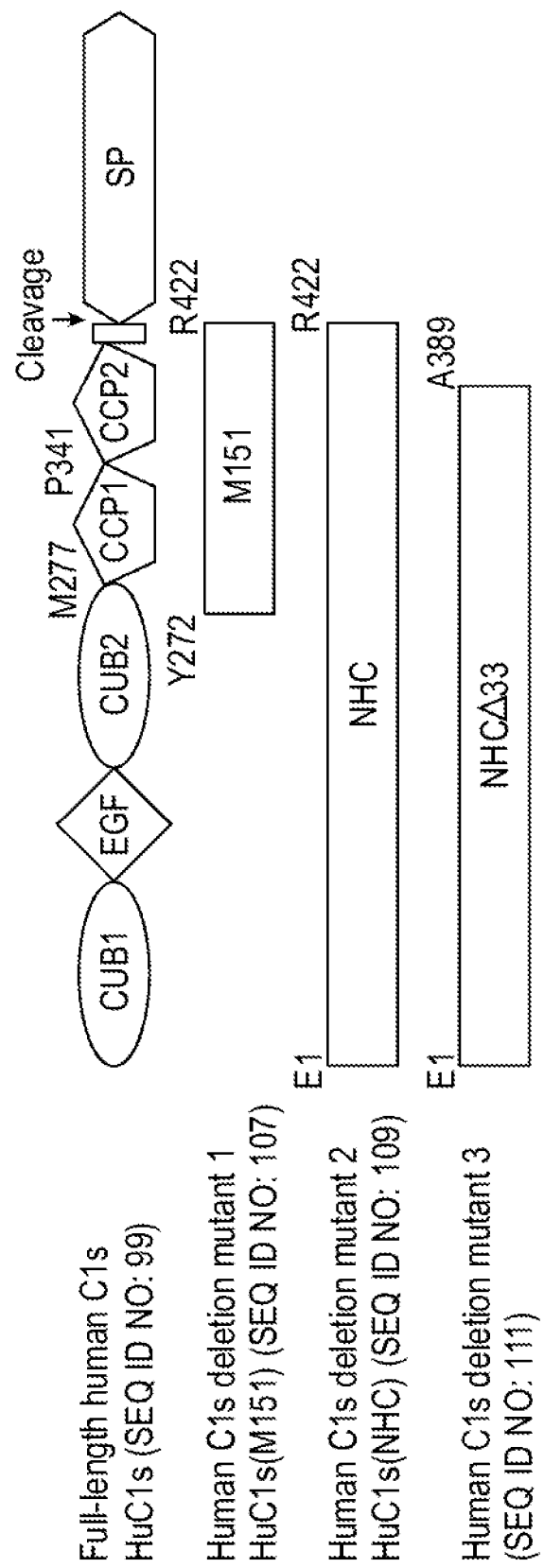

Example 6. Epitope Mapping of Anti-C1s Antibodies Using Truncated C1s and C1s with Point Mutations As indicated in Examples 4-5, the epitopes of anti-C1s antibodies disclosed herein are located within human C1s (M151) (SEQ ID NO: 107). Human C1s (M151) is the last 151 amino acids upstream of auto-cleavage site (R422-1423) within the human C1s NHC. In order to further define the epitopes within human C1s (M151), a further truncated C1s mutant was designed. This mutant is named human C1s deletion mutant 3 (NHCΔ33) (SEQ ID NO:111) and is lacking the last 33 amino acids, corresponding to G390-R422 fragment of human C1s NHC (FIG. 5B for alignment). C1s (NHCΔ33) (SEQ ID NO: 111) was cloned and expressed with a C-terminal 6×His tag, and its expression and purification were performed in house. FIG. 5B shows a schematic comparison and alignment of full-length human C1s, HuC1s (SEQ ID NO: 99), human C1s deletion mutant 1 (M151), HuC1s(M151), (SEQ ID NO: 107), human deletion mutant 2 (NHC), HuC1s(NHC) (SEQ ID NO: 109) and human C1s deletion mutant 3 (NHCΔ33), human C1s (NHCΔ33) (SEQ ID NO:111) used in these experiments.

Figure 6A:
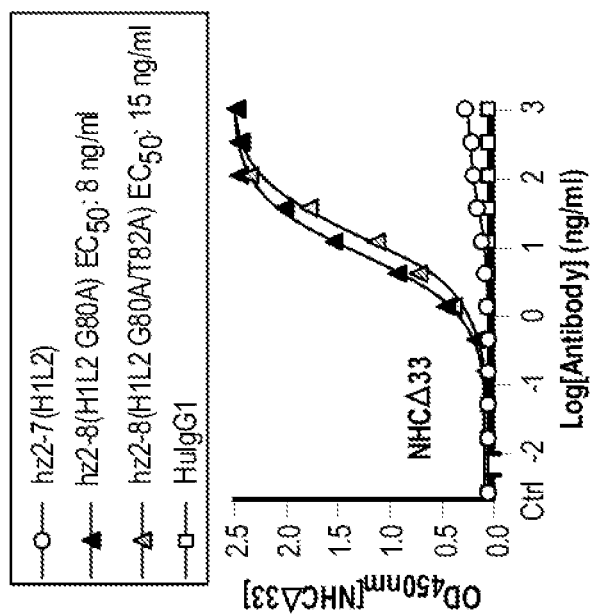
Figure 6C:
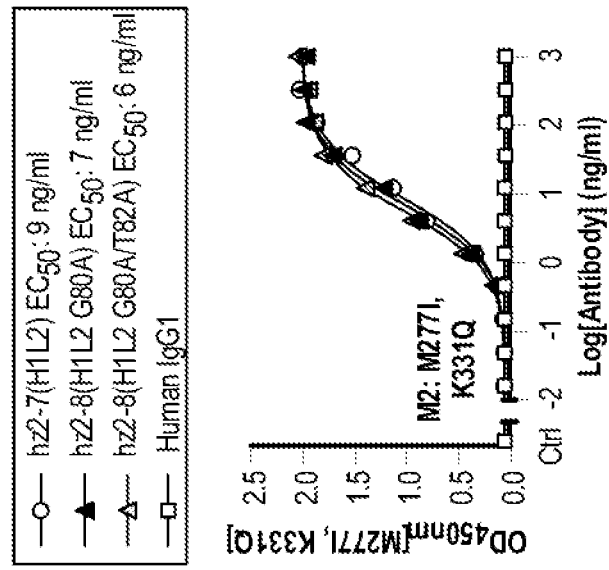
FIG. 6C shows binding to M2 (M277I & K331Q)

Binding of various anti-C1s antibodies to human C1s (NHCΔ33) (SEQ ID NO: 111) was carried out by ELISA as described in Example 4, and results are shown in FIG. 6A. Hz2-7(H1L2) showed almost no binding to human C1s (NHCΔ33), while hz2-8(H1L2 G80A) and hz2-8(H1L2 80A/T82A) showed strong binding to C1s (NHCΔ33) with ECO values of 8 ng/ml and 15 ng/ml, respectively. As expected, human IgG showed no binding. Such distinct binding profiles of humanized 2-7 variant versus humanized 2-8 variants strongly suggest that antibody 2-7 and 2-8 bind to distinct epitopes within the human C1s (M151) as demonstrated in Example 4. The results indicate that the epitopes of hz2-7(H1L2) are within the 33 amino acids located upstream of cleavage sites (G390-R422), and the epitopes of hz2-8(H1L2 G80A) and hz2-8(H1L2 G80A-T82A) are within the rest of M151 (Y272-A389).

In order to identify the epitopes of hz2-8(H1L2 G80A) and hz2-8(H1L2 G80A/T82A), we introduced various point mutations to human C1s either individually or in double/triple combinations, and obtained 20 human C1s mutants named M1-M20 (SEQ ID NOs: 112-128 and 141-143) as shown in Table 2.

For all point mutations, the residue at a certain position of human C1s was substituted for the corresponding residue of mouse C1s. Among 22 residues that were mutated, 6 are identical between human C1s and rat C1s, 10 are identical between rat C1s and mouse C1s, and the remaining 6 are unique residues at the corresponding positions for human-, rat-, and mouse C1s. M1-M20 of human C1s (SEQ ID NOS: 112-128 and 141-143) were cloned with a C-terminal 6×His tag, expressed and purified in house.

TABLE 2

Point mutations of human C1s and corresponding residues of rat- and mouse C1s

| Point mutation | Human C1s | Rat C1s | Mouse C1s | C1s mutants with point mutation |
|---|---|---|---|---|
| M277I | M | | I | M1 (SEQ ID NO: 112), M2 (SEQ ID NO: 113), M3 (SEQ ID NO: 114) |
| P278S | P | | S | M3 (SEQ ID NO: 114) |
| P280A | P | | A | M4 (SEQ ID NO: 115), M6 (SEQ ID NO: 117) |
| E282K | E | | K | M4 (SEQ ID NO: 115), M6 (SEQ ID NO: 117) |
| D283I | D | | I | M10 (SEQ ID NO: 121) |
| P285A | P | | A | M10 (SEQ ID NO: 121) |
| V288T | V | I | T | M18 (SEQ ID NO: 141) |
| A292D | A | E | D | M13 (SEQ ID NO: 124) |
| Q303K | Q | | K | M19 (SEQ ID NO: 142) |
| R316H | R | N | H | M14 (SEQ ID NO: 125) |
| A320S | A | | S | M20 (SEQ ID NO: 143) |
| N329D | N | | D | M3 (SEQ ID NO: 114) |
| K331Q | K | | Q | M2 (SEQ ID NO: 113) |
| K336G | K | R | G | M5 (SEQ ID NO: 116), M6 (SEQ ID NO: 117), M9 (SEQ ID NO: 120) |
| D343Y | D | | Y | M7 (SEQ ID NO: 118), M9 (SEQ ID NO: 120) |
| S349P | S | | P | M11 (SEQ ID NO: 122) |
| E351A | E | | A | M7 (SEQ ID NO: 118), M8 (SEQ ID NO: 119), M9 (SEQ ID NO: 120) |
| S360N | S | D | N | M15 (SEQ ID NO: 126) |
| R368H | R | | H | M16 (SEQ ID NO: 127) |
| N380H | N | Q | H | M17 (SEQ ID NO: 128) |
| G381E | G | | E | M12 (SEQ ID NO: 123) |
| G382E | G | | E | M12 (SEQ ID NO: 123) |

Figure 6B:
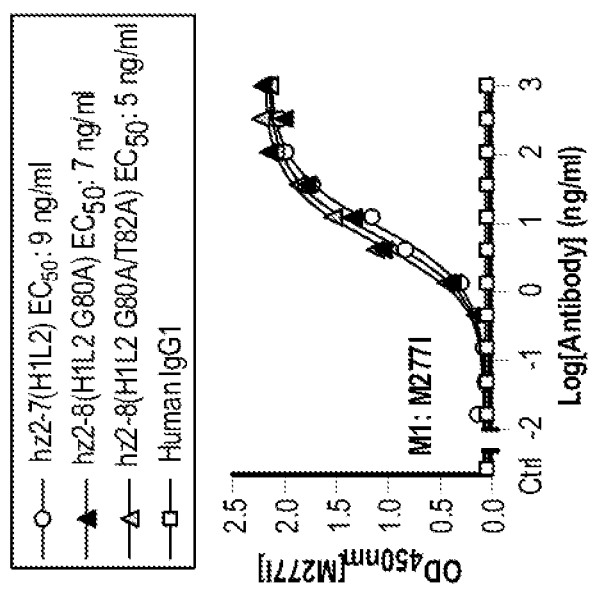
FIG. 6B shows binding to M1 (M277I)
Figure 6E:
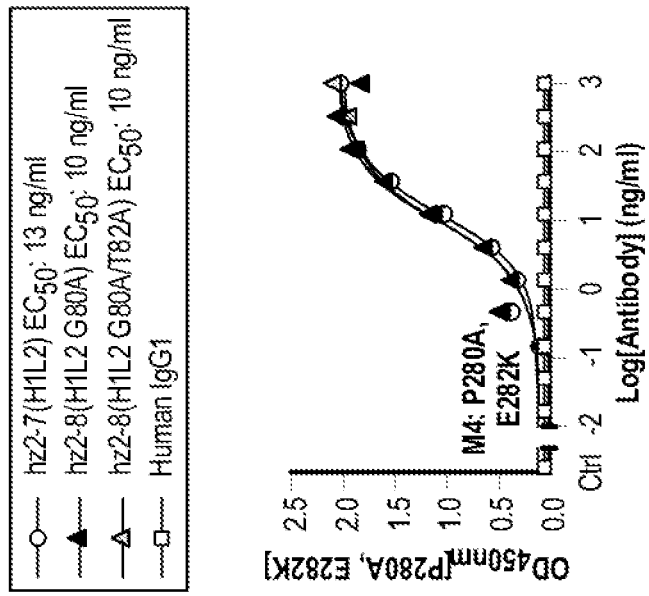
FIG. 6E shows binding to M4 (P280A & E282K)
Figure 6D:
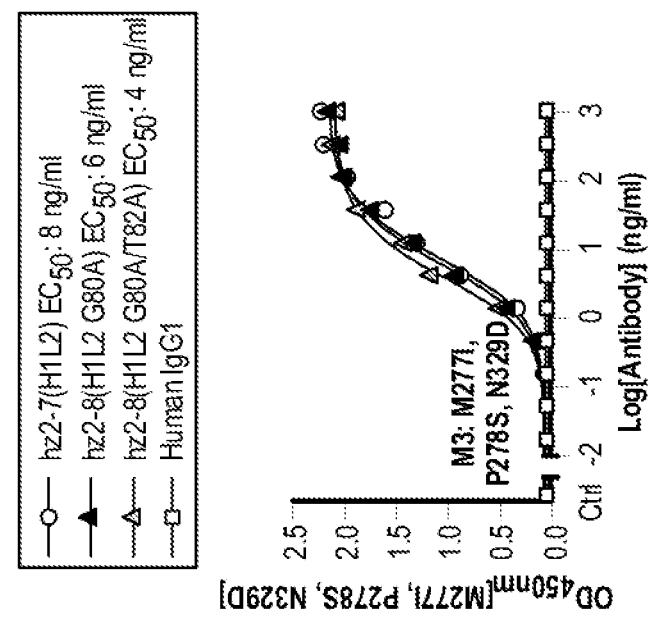
FIG. 6D shows binding to M3 (M277I, P278S & N329D)
Figure 6G:
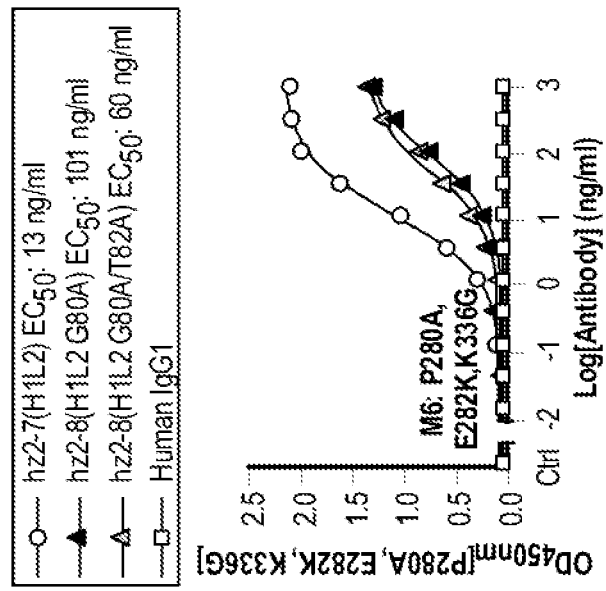
FIG. 6G shows binding to M6 (P280A, E282K & K336G)
Figure 6F:
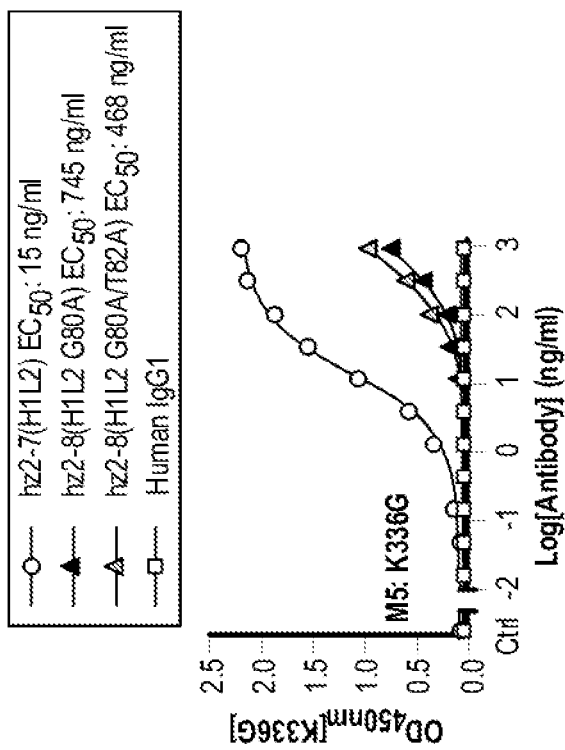
FIG. 6F shows binding to M5 (K336G)
Figure 6I:
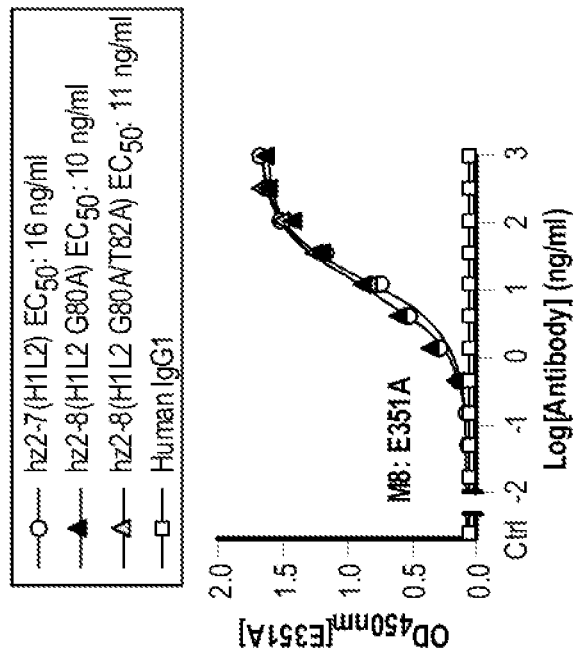
FIG. 6I shows binding to M8 (E351A)
Figure 6H:
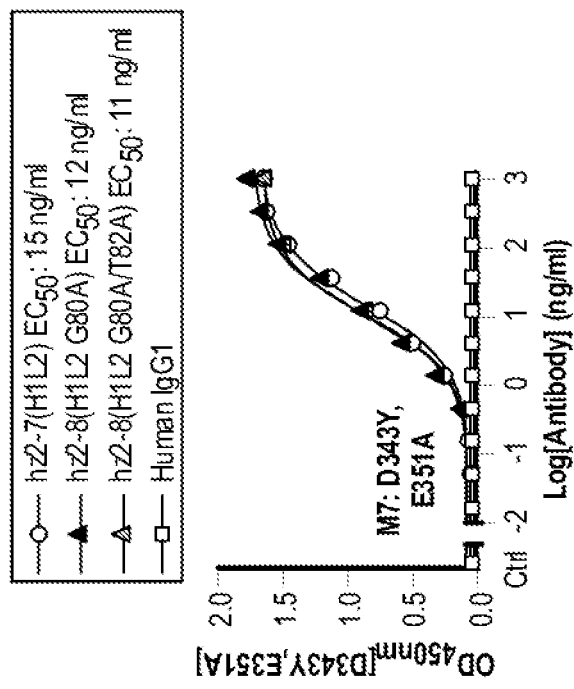
FIG. 6H shows binding to M7 (D343Y & E351A)
Figure 6K:
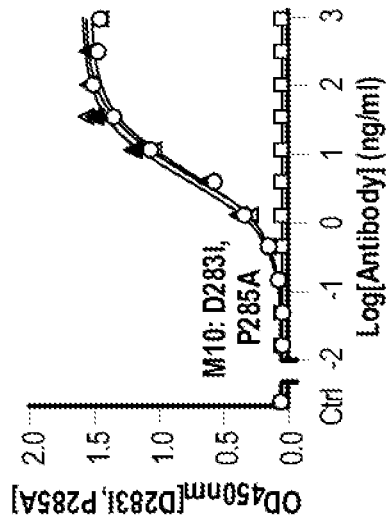
FIG. 6K shows binding to M10 (D2831 & P285A)
Figure 6J:
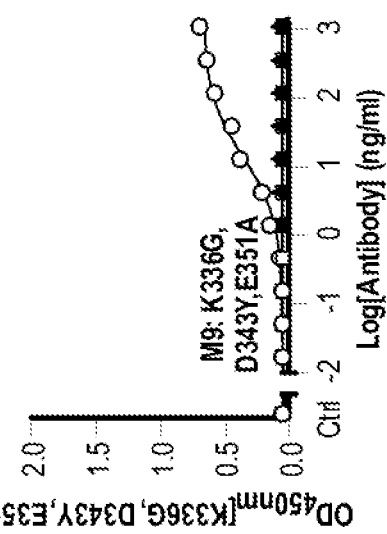
FIG. 6J shows binding to M9 (K336G, D343Y & E351A)
Figure 6M:
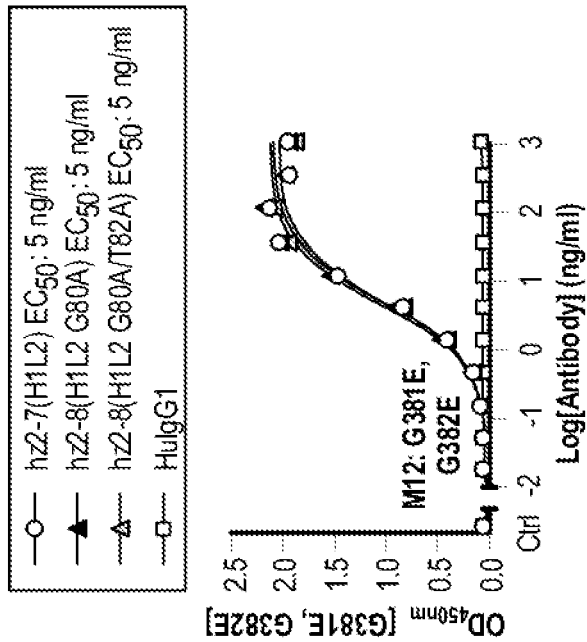
FIG. 6M shows binding to M12 (G381E & G382E)
Figure 6L:
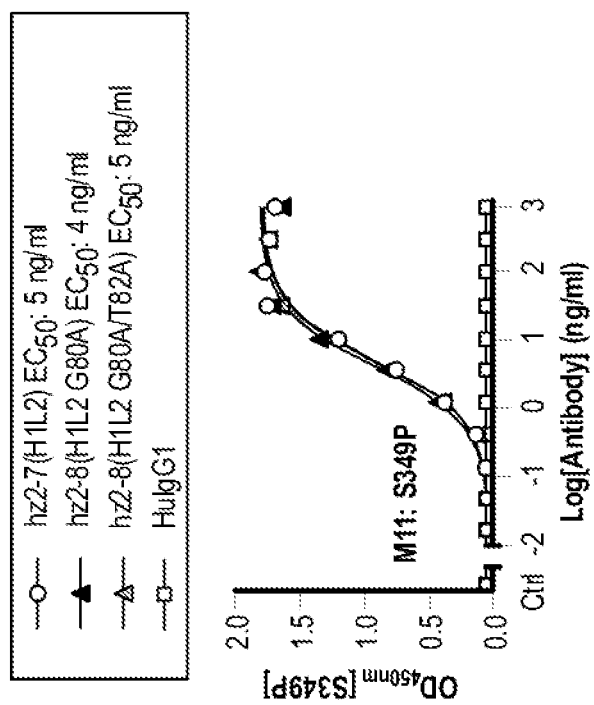
FIG. 6L shows binding to M11 (S349P)
Figures 6N, 6O:
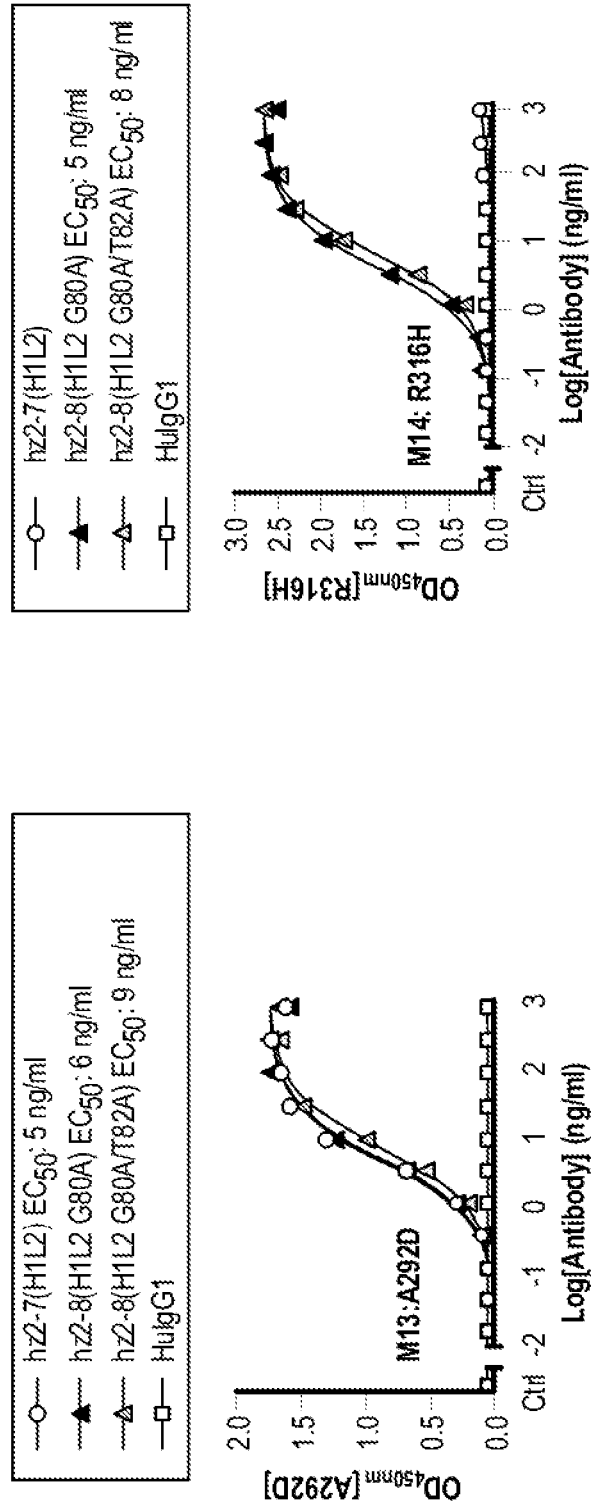
FIG. 6N shows binding to M13 (A292D)
FIG. 6O shows binding to M14 (R316H)
Figures 6P, 6Q:
FIG. 6P shows binding to M15 (S360N)
FIG. 6Q shows binding to M16 (R368H)
Figure 6R:
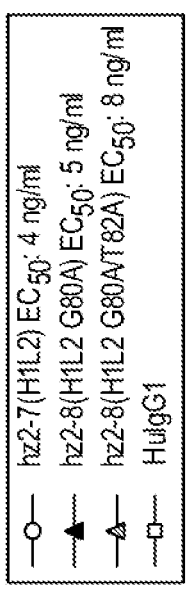
FIG. 6R shows binding to M17 (N380H).
Figure 6R:
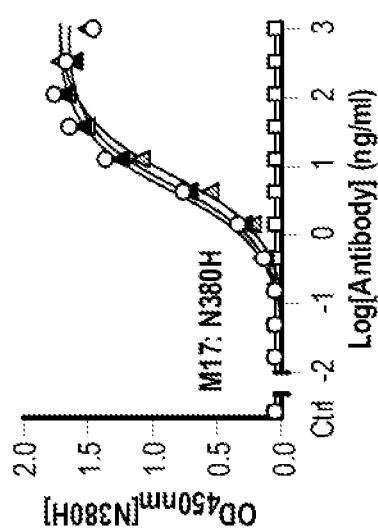
Figure 6S:
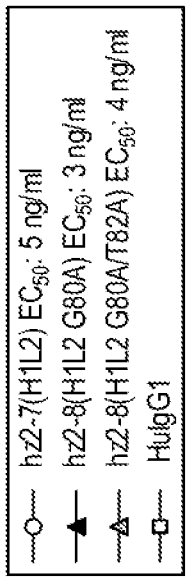
FIG. 6S shows binding to M18 (V288T)
Figure 6S:
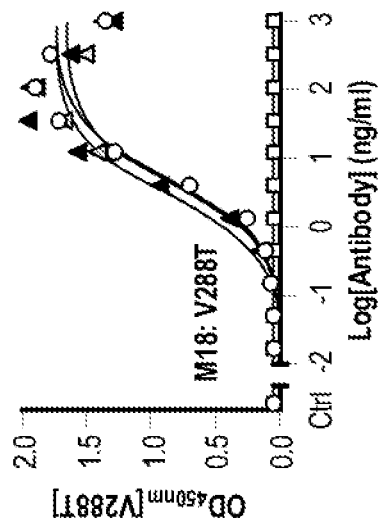

Binding of anti-C1s antibodies to mutants M1-M20 of human C1s was measured by ELISA as described in Example 4, and results are shown in FIGS. 6B-6U. All anti-C1s humanized variants including hz2-7(H1L2), hz2-8 (H1L2 G80A) and hz2-8(H1L2 G80A/T82A) maintained strong binding properties to the majority (16 out of 20) of C1s mutants including M1 (FIG. 6B combination with other non-essential residues (M6). As shown in FIG. 6F-G. K336G single mutation resulted in a significantly reduced binding of hz2-8(H1L2 G80A) and hz2-8(H1L2 G80A % T82A) but had no effect on hz2-7 (H1L2), confirmed that K336 is the key residue for binding of hz2-8(H1L2 G80A) and hz2-8(H1L2 G80A/T82A) to C1s, constituting a unique epitope for 2-8 antibody.

Taken together, the epitope of hz2-7(H1L2) comprises R316 and G390-R422, and the critical residue for binding of hz2-8(H1L2 G80A) and hz2-8(H1L2 G80A/T82A) to C1s is K336. The results indicated that epitopes of antibody 2-7 versus antibody 2-8 are distinct although all occur within the middle 151 amino acid region of human C1s (M151).

Example 7. Inhibition by Anti-C1S Antibodies of Complement-Mediated Lysis of Antibody-Sensitized Sheep Erythrocyte Sheep red blood cells coated with rabbit anti-sheep erythrocyte antiserum (hemolysin), which is also known as antibody-sensitized sheep erythrocytes (EA), have traditionally been used to assay the activity of the complement classical pathway in serum samples, where these assays allow determination of the CH50 titer of the serum. Taking advantage of commercially available EA (Complement Technology. #B202), inhibition of complement-mediated lysis of EA by anti-C1s antibodies was assessed. Briefly, humanized anti-C1s variants, including hz2-7(H1L2), hz2-8(H1L2), hz2-8 (H1L2 G80A) and hz2-8(H1L2 G80A/T82A), were first serially diluted in (GVB++ buffer (Complement Technology, Catalog #B100, manufacturer ingredient list: 0.1% gelatin, 5 mM Veronal, 145 mM NaCl, 0.025% $NaN_3$, 0.15 mM calcium chloride, 0.5 mM magnesium chloride, pH 7.3). The diluted anti-C1s antibodies were then mixed with normal human serum (NHS, FIG. 7A) or with cynomolgus monkey serum (CMS, FIG. 7B) to reach a final serum concentration of 1%. Antibody and serum mixture were equilibrated at room temperature before adding EA cells. For each reaction, approximately $0.5\text{-}1\times10^8$ EA cells were used. To determine the 0% lysis background control value, EA cells were mixed with buffer only ("no serum controls"). To determine the 100% lysis control value, GVB++ buffer was replaced with water. EA cells were gently mixed with the antibody and serum, then the mixtures were incubated at 37° C. for 1 hr with periodic mixing. After incubation, the remaining EA cells were spun down, and the absorbance of supernatant were determined by measuring $OD_{540\ nm}$. To calculate the percentage of lysis that occurred under specific incubation conditions, the value of the 0% lysis background was first subtracted from each absorbance reading, and the results were then normalized to the 100% lysis control (with 0% lysis background subtracted) to determine the percentage of lysis that occurred.

The results for human complement inhibition by anti-C1s antibody are shown in FIG. 7A. Antibody hz2-8(H1L2) was the most potent inhibitor of complement-mediated lysis of EA, with $IC_{50}$ of 0.2 μg/ml. Antibodies hz2-8(H1L2 G80A) and hz2-8(H1L2 G80A/T82A), each of which are sequence-optimized variants of hz2-8(H1L2), also effectively inhibited human complement-mediated lysis of EA with similar $IC_{50}$ between 0.4-0.5 μg/ml, hz2-7(H1L2) was the weakest inhibitor in this case with $IC_{50}$ of 4.1 μg/ml, and the maximal inhibition only reached about 50% at the highest concentration tested (4 μg/ml). The results for cynomolgus monkey complement inhibition as shown in FIG. 7B are similar to the human serum results, where hz2-8(H1L2) was the most potent inhibitor of cynomolgus monkey complement-mediated lysis of EA with an $IC_{50}$ of 0.1 μg/ml, and its variants hz2-8(H1L2 G80A) and hz2-8(111 L2 G80A/T82A) also maintained high inhibition potency with similar $IC_{50}$ values between 0.3-0.4 μg/ml. Hz2-7(H1L2) inhibited cynomolgus monkey complement more effectively than human complement, with $IC_{50}$ of 0.8 μg/ml and an extent of inhibition that reaches maximum (FIG. 7B). These results strongly support the role of various anti-C1s antibodies in the inhibition of classical complement pathway, which is consistent with findings from Example 2.

While the present invention has been described with reference to certain specific embodiments thereof, it should be understood by those skilled in the art that changes and modifications in the specifically-described embodiments may be carried out without departing from the principles of the present invention, which is intended to be limited only by the scope of the appended claims.

What is claimed is:

1. A recombinant anti-C1s antibody or an antigen-binding fragment thereof that is capable of specifically binding to human C1s and inhibiting C1s, comprising a heavy chain variable region (VH) comprising three heavy chain complementarity determining regions (HC CDRs) and a light chain variable region (VL) comprising three light chain complementarity determining regions (LC CDRs), selected from:
   (a) the VH comprising an HC CDR1 having the amino acid sequence GFTFSNYFMN (SEQ ID NO: 129), an HC CDR2 having the amino acid sequence EIRLKFTNYATHYA(E/D)SV(EX)G (SEQ ID NO: 130), and an HC CDR3 having the amino acid sequence DYGSRN(G/A)YFDY (SEQ ID NO: 131), and the VL comprising an LC CDR1 having the amino acid sequence RSSKSLLHSNGNTFLY (SEQ ID NO: 132), an LC CDR2 having the amino acid sequence RMSNLAS (SEQ ID NO: 133), and an LC CDR3 having the amino acid sequence MQHLEYPYT (SEQ ID NO: 134), and
   (b) the VH comprising an HC CDR1 having the amino acid sequence GFNIKEYYMH (SEQ ID NO: 135), an HC CDR2 having the amino acid sequence WIDPEN(G/A)D(T/A)IY(D/A)(P/Q)KFQG (SEQ ID NO: 136), and an HC CDR3 having the amino acid sequence SRLFFAY (SEQ ID NO: 137), and the VL comprising an LC CDR1 having the amino acid sequence ASQDVRTA(V/L)D (SEQ ID NO: 138), an LC CDR2 comprising the amino acid sequence SASYRY(T/S) (SEQ ID NO: 139), and LC CDR3 comprising the amino acid sequence QQQYTTPYT (SEQ ID NO: 140).

2. The anti-C1s antibody of claim 1, wherein the antibody is capable of binding to at least one of residues K336, R316, and a region encompassing A390-R422 of human C1s (SEQ ID NO: 99).

3. The anti-C1s antibody of claim 1, wherein the anti-C1s antibody is capable of inhibiting the activity of the classical pathway (CP) of complement activation.

4. The anti-C1s antibody of claim 3, wherein the anti-C1s antibody is capable of at least one of inhibiting downstream effects of C1s activation, inhibiting IgM-induced deposition of C4 from serum, inhibiting antibody-antigen complex mediated C4 cleavage, inhibiting antibody-antigen complex mediated deposition of C4b, inhibiting formation of C3 convertase, and inhibiting downstream effects of CP activation.

5. The anti-C1s antibody of claim 1, wherein the antibody shows cross-reactivity with at least one non-human C1s.

6. The anti-C1s antibody of claim 5, wherein the non-human C1s is cynomolgus monkey C1s.

7. The anti-C1s antibody of claim 6, wherein the anti-C1s antibody shows cross-reactivity with rat C1s.

8. The anti-C1s antibody of claim 1, wherein the antibody is at least one of a chimeric antibody, a humanized antibody, and an antigen-binding fragment.

9. The anti-C1s antibody of claim 1, comprising at least one polypeptide having an amino acid sequence selected from: SEQ ID NO: 1; SEQ ID NO: 2; SEQ ID NO: 3; SEQ ID NO: 4; SEQ ID NO: 6; SEQ ID NO: 7; SEQ ID NO: 8; SEQ ID NO: 9; SEQ ID NO: 11; SEQ ID NO: 12; SEQ ID NO: 13; SEQ ID NO: 14; SEQ ID NO: 16; SEQ ID NO: 17; SEQ ID NO: 18; SEQ ID NO: 19; SEQ ID NO: 21; SEQ ID NO: 22; SEQ ID NO: 23; SEQ ID NO: 24; SEQ ID NO: 26; SEQ ID NO: 27; SEQ ID NO: 28; SEQ ID NO: 29; SEQ ID NO: 31; SEQ ID NO: 32; SEQ ID NO: 33; SEQ ID NO: 34; SEQ ID NO: 36; SEQ ID NO: 37; SEQ ID NO: 38; SEQ ID NO: 39; SEQ ID NO: 41; SEQ ID NO: 42; SEQ ID NO: 43; SEQ ID NO: 44; SEQ ID NO: 46; SEQ ID NO: 47; SEQ ID NO: 48; SEQ ID NO: 49; SEQ ID NO: 51; SEQ ID NO: 52; SEQ ID NO: 53; SEQ ID NO: 54; SEQ ID NO: 56; SEQ ID NO: 57; SEQ ID NO: 58; SEQ ID NO: 59; SEQ ID NO: 61; SEQ ID NO: 62; SEQ ID NO: 63; SEQ ID NO: 64; SEQ ID NO: 66; SEQ ID NO: 67; SEQ ID NO: 68; SEQ ID NO: 69; SEQ ID NO: 71; SEQ ID NO: 73; SEQ ID NO: 75; SEQ ID NO: 77; SEQ ID NO: 79; SEQ ID NO: 81; SEQ ID NO: 83; SEQ ID NO: 85; SEQ ID NO: 87; SEQ ID NO: 89; SEQ ID NO: 91; SEQ ID NO: 93; SEQ ID NO: 95; or SEQ ID NO: 97.

10. The anti-C1s antibody of claim 1, wherein the antibody is one of:
   a. an antibody comprising a heavy chain (HC) polypeptide having the amino acid sequence of SEQ JD NO: 71 or a sequence at least about 85% identical to SEQ ID NO: 71, and a light chain (LC) polypeptide having the amino acid sequence of SEQ ID NO: 73 or a sequence at least about 85% identical to SEQ ID NO: 73;
   b. an antibody comprising an HC polypeptide having the amino acid sequence of SEQ ID NO: 75 or a sequence at least about 85% identical to SEQ ID NO: 75, and an LC polypeptide having the amino acid sequence of SEQ ID NO: 77 or a sequence at least about 85% identical to SEQ ID NO: 77;
   c. an antibody comprising an HC polypeptide having the amino acid sequence of SEQ ID NO: 79 or a sequence at least about 85% identical to SEQ ID NO: 79, and an LC polypeptide having the amino acid sequence of SEQ ID NO: 81 or a sequence at least about 85% identical to SEQ ID NO: 81;
   d. an antibody comprising an HC polypeptide having the amino acid sequence of SEQ ID NO: 83 or a sequence at least about 85% identical to SEQ ID NO: 83, and an LC polypeptide having the amino acid sequence of SEQ ID NO: 85 or a sequence at least about 85% identical to SEQ ID NO: 85;
   e. an antibody comprising an HC polypeptide having the amino acid sequence of SEQ ID NO: 87 or a sequence at least about 85% identical to SEQ ID NO: 87, and an LC polypeptide having the amino acid sequence of SEQ ID NO: 89 or a sequence at least about 85% identical to SEQ ID NO: 89;
   f. an antibody comprising an HC polypeptide having the amino acid sequence of SEQ ID NO: 91 or a sequence at least about 85% identical to SEQ ID NO: 91, and an LC polypeptide having the amino acid sequence of SEQ ID NO: 93 or a sequence at least about 85% identical to SEQ ID NO: 93; or
   g. an antibody comprising an HC polypeptide having the amino acid sequence of SEQ ID NO: 95 or a sequence at least about 85% identical to SEQ ID NO: 95, and an LC polypeptide having the amino acid sequence of SEQ ID NO: 97 or a sequence at least about 85% identical to SEQ ID NO: 97.

11. The anti-C1s antibody of claim 1, wherein the antibody is one of:
   a. an antibody comprising a heavy chain variable region (VH) having the amino acid sequence of SEQ ID NO: 1 or a sequence at least about 85% identical to SEQ ID NO: 1, and a light chain variable region (VL) having the amino acid sequence of SEQ ID NO: 6 or a sequence at least about 85% identical to SEQ ID NO: 6;
   b. an antibody comprising a VH having the amino acid sequence of SEQ ID NO: 11 or a sequence at least about 85% identical to SEQ ID NO: 11, and an VL having the amino acid sequence of SEQ ID NO: 16 or a sequence at least about 85% identical to SEQ ID NO: 16;

c. an antibody comprising a VH having the amino acid sequence of SEQ ID NO: 21 or a sequence at least about 85% identical to SEQ ID NO: 21, and an VL having the amino acid sequence of SEQ ID NO: 26 or a sequence at least about 85% identical to SEQ ID NO: 26;

d. an antibody comprising a VH having the amino acid sequence of SEQ ID NO: 31 or a sequence at least about 85% identical to SEQ ID NO: 31, and an VL having the amino acid sequence of SEQ ID NO: 36 or a sequence at least about 85% identical to SEQ ID NO: 36;

e. an antibody comprising a VH having the amino acid sequence of SEQ ID NO: 41 or a sequence at least about 85% identical to SEQ ID NO: 41, and an VL having the amino acid sequence of SEQ ID NO: 46 or a sequence at least about 85% identical to SEQ ID NO: 46;

f. an antibody comprising a VH having the amino acid sequence of SEQ ID NO: 51 or a sequence at least about 85% identical to SEQ ID NO: 51, and an VL having the amino acid sequence of SEQ ID NO: 56 or a sequence at least about 85% identical to SEQ ID NO: 56; or g. an antibody comprising a VH having the amino acid sequence of SEQ ID NO: 61 or a sequence at least about 85% identical to SEQ ID NO: 61, and an VL having the amino acid sequence of SEQ ID NO: 66 or a sequence at least about 85% identical to SEQ ID NO: 66.

12. The anti-C1s antibody of claim 1, wherein the antibody comprises an HC CDR1 of SEQ ID NO: 22, an HC CDR2 of SEQ ID NO: 23, an HC CDR3 of SEQ ID NO: 24, an LC CDR1 of SEQ ID NO: 27, an LC CDR2 of SEQ ID NO: 28, and an LC CDR3 of SEQ ID NO: 29, and further wherein the antibody may comprise 3 or fewer total amino acid substitutions in the CDR regions.

13. The anti-C1s antibody of claim 1, wherein the antibody comprises an HC CDR1 of SEQ ID NO: 52, an HC CDR2 of SEQ ID NO: 53, an HC CDR3 of SEQ ID NO: 54, an LC CDR1 of SEQ ID NO: 57, an LC CDR2 of SEQ ID NO: 58, and an LC CDR3 of SEQ ID NO: 59, and further wherein the antibody may comprise 6 or fewer total amino acid substitutions in the CDR regions.

14. A method of treating a complement-mediated disorder, comprising administering an effective amount of an anti-C1s antibody of claim 1 to a subject in need thereof, wherein administration of the effective amount of anti-C1s antibody inhibits the activity of the CP.

15. The method of claim 14, wherein the complement-mediated disorder is an autoimmune disorder characterized by binding of complement-fixing antibodies to at least one self-antigen.

16. The method of claim 15, wherein the autoimmune disorder is selected from one of immune thrombocytopenic purpura (ITP) and neuromyelitis optica (NMO).

17. The method of claim 14, wherein administration of the effective amount of anti-C1s antibody inhibits at least one of C1s activation, antibody-antigen complex mediated C4 cleavage, and formation of a common complement pathway effector.

18. The method of claim 14, wherein the effective amount of anti-C1s antibody is administered during an acute phase of the disorder.

19. A pharmaceutical composition comprising the anti-C1s antibody of claim 1 and a suitable carrier and/or excipient.

20. An isolated nucleic acid molecule that encodes at least a portion of the anti-C1s antibody of claim 1, wherein the nucleic acid comprises at least one nucleotide sequence selected from a. a heavy-chain (HC) nucleotide sequence selected from: a nucleotide sequence comprising the sequence of SEQ ID NO: 5, a nucleotide sequence comprising a sequence at least about 85% identical to SEQ ID NO: 5, a nucleotide sequence comprising the sequence of SEQ ID NO: 15, a nucleotide sequence comprising a sequence at least about 85% identical to SEQ ID NO: 15, a nucleotide sequence comprising the sequence of SEQ ID NO. 25, a nucleotide sequence comprising a sequence at least about 85% identical to SEQ ID NO: 25, a nucleotide sequence comprising the sequence of SEQ ID NO: 35, a nucleotide sequence comprising a sequence at least about 85% identical to SEQ ID NO: 35, a nucleotide sequence comprising the sequence of SEQ ID NO: 45, a nucleotide sequence comprising a sequence at least about 85% identical to SEQ ID NO: 45, a nucleotide sequence comprising the sequence of SEQ ID NO: 55, a nucleotide sequence comprising a sequence at least about 85% identical to SEQ ID NO: 55, a nucleotide sequence comprising the sequence of SEQ ID NO: 65, and a nucleotide sequence comprising a sequence at least about 85% identical to SEQ ID NO: 65, and b. a light chain (LC) nucleotide sequence selected from: a nucleotide sequence comprising the sequence of SEQ ID NO: 10, a nucleotide sequence comprising a sequence at least about 85% identical to SEQ ID NO: 10, a nucleotide sequence comprising the sequence of SEQ ID NO: 20, a nucleotide sequence comprising a sequence at least about 85% identical to SEQ ID NO: 20, a nucleotide sequence comprising the sequence of SEQ ID NO. 30, a nucleotide sequence comprising a sequence at least about 85% identical to SEQ ID NO: 30, a nucleotide sequence comprising the sequence of SEQ ID NO: 40, a nucleotide sequence comprising a sequence at least about 85% identical to SEQ ID NO: 40, a nucleotide sequence comprising the sequence of SEQ ID NO: 50, a nucleotide sequence comprising a sequence at least about 85% identical to SEQ ID NO: 50, a nucleotide sequence comprising the sequence of SEQ ID NO: 60, a nucleotide sequence comprising a sequence at least about 85% identical to SEQ ID NO: 60, a nucleotide sequence comprising the sequence of SEQ ID NO: 70, and a nucleotide sequence comprising a sequence at least about 85% identical to SEQ ID NO: 70.

21. A vector comprising a nucleic acid molecule of claim 20.

22. A host cell comprising the vector of claim 21.

* * * * *

SEQUENCE LISTING

```
<160> NUMBER OF SEQ ID NOS: 143

<210> SEQ ID NO 1
<211> LENGTH: 141
<212> TYPE: PRT
<213> ORGANISM: Mus musculus
<220> FEATURE:
<223> OTHER INFORMATION: Protein sequence of antibody 2-7 VH

<400> SEQUENCE: 1

Met Tyr Leu Gly Leu Asn Cys Val Phe Ile Val Phe Leu Leu Lys Gly
1               5                   10                  15

Val Gln Ser Glu Val Lys Leu Glu Glu Ser Gly Gly Gly Leu Val Pro
            20                  25                  30

Pro Gly Gly Ser Met Lys Leu Ser Cys Val Ala Ser Gly Phe Thr Phe
        35                  40                  45

Ser Asn Tyr Phe Met Asn Trp Val Arg Gln Ser Pro Glu Lys Gly Leu
    50                  55                  60

Glu Trp Val Ala Glu Ile Arg Leu Lys Phe Thr Asn Tyr Ala Thr His
65                  70                  75                  80
```

```
Tyr Ala Glu Ser Val Glu Gly Arg Phe Thr Ile Ser Arg Asp Asp Ser
            85                  90                  95

Lys Ser Ser Val Tyr Leu Gln Met Asn Asn Leu Arg Ala Glu Asp Thr
        100                 105                 110

Gly Ile Tyr Tyr Cys Thr Arg Asp Tyr Gly Ser Arg Asn Gly Tyr Phe
        115                 120                 125

Asp Tyr Trp Gly Gln Gly Thr Thr Leu Thr Val Ser Ser
    130                 135                 140

<210> SEQ ID NO 2
<211> LENGTH: 10
<212> TYPE: PRT
<213> ORGANISM: Mus musculus
<220> FEATURE:
<223> OTHER INFORMATION: 2-7 HC CDR-1

<400> SEQUENCE: 2

Gly Phe Thr Phe Ser Asn Tyr Phe Met Asn
1               5                   10

<210> SEQ ID NO 3
<211> LENGTH: 19
<212> TYPE: PRT
<213> ORGANISM: Mus musculus
<220> FEATURE:
<223> OTHER INFORMATION: 2-7 HC CDR-2

<400> SEQUENCE: 3

Glu Ile Arg Leu Lys Phe Thr Asn Tyr Ala Thr His Tyr Ala Glu Ser
1               5                   10                  15

Val Glu Gly

<210> SEQ ID NO 4
<211> LENGTH: 11
<212> TYPE: PRT
<213> ORGANISM: Mus musculus
<220> FEATURE:
<223> OTHER INFORMATION: 2-7 HC CDR-3

<400> SEQUENCE: 4

Asp Tyr Gly Ser Arg Asn Gly Tyr Phe Asp Tyr
1               5                   10

<210> SEQ ID NO 5
<211> LENGTH: 423
<212> TYPE: DNA
<213> ORGANISM: Mus musculus
<220> FEATURE:
<223> OTHER INFORMATION: Nucleotide sequence of antibody 2-7 VH

<400> SEQUENCE: 5
atgtacttgg gactgaactg tgtattcata gttttctctc taaaaggtgt ccagagtgaa    60
gtgaagcttg aggagtctgg aggaggcttg gtgccacctg gaggatccat gaaactctcc   120
tgtgttgcct ctggattcac tttcagtaac tactttatga actgggtccg ccagtctcca   180
gagaaggggc ttgagtgggt tgctgaaatt agattgaaat tactaattta tgcaacacat   240
tatgcggagt ctgtggaagg gaggttcacc atctcaagag atgattccaa agtagtgtc    300 tacctccaaa tgaacaactt aagagctgaa gacactggca tttattactg taccagggac   360
tacggtagta ggaatgggta ctttgactac tggggccaag gcaccactct cacagtctcc   420
tca                                                                 423
```

```
<210> SEQ ID NO 6
<211> LENGTH: 132
<212> TYPE: PRT
<213> ORGANISM: Mus musculus
<220> FEATURE:
<223> OTHER INFORMATION: Protein sequence of antibody 2-7 VL

<400> SEQUENCE: 6

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Ser Lys Ser
        35                  40                  45

Leu Leu His Ser Asn Gly Asn Thr Phe Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Val Ser Arg Val Glu Ala Glu Asp Val Gly Ile Tyr Tyr
            100                 105                 110

Cys Met Gln His Leu Glu Tyr Pro Tyr Thr Phe Gly Gly Gly Thr Lys
        115                 120                 125

Leu Glu Ile Lys
    130

<210> SEQ ID NO 7
<211> LENGTH: 16
<212> TYPE: PRT
<213> ORGANISM: Mus musculus
<220> FEATURE:
<223> OTHER INFORMATION: 2-7 LC CDR-1

<400> SEQUENCE: 7

Arg Ser Ser Lys Ser Leu Leu His Ser Asn Gly Asn Thr Phe Leu Tyr
1               5                   10                  15

<210> SEQ ID NO 8
<211> LENGTH: 7
<212> TYPE: PRT
<213> ORGANISM: Mus musculus
<220> FEATURE:
<223> OTHER INFORMATION: 2-7 LC CDR-2

<400> SEQUENCE: 8

Arg Met Ser Asn Leu Ala Ser
1               5

<210> SEQ ID NO 9
<211> LENGTH: 9
<212> TYPE: PRT
<213> ORGANISM: Mus musculus
<220> FEATURE:
<223> OTHER INFORMATION: 2-7 LC CDR-3

<400> SEQUENCE: 9

Met Gln His Leu Glu Tyr Pro Tyr Thr
1               5

<210> SEQ ID NO 10
```

-continued

```
<211> LENGTH: 396
<212> TYPE: DNA
<213> ORGANISM: Mus musculus
<220> FEATURE:
<223> OTHER INFORMATION: Nucleotide sequence of antibody 2-7 VL

<400> SEQUENCE: 10
atgaggtgcc tagctgagtt cctggggctg cttgtgctct ggatccctgg agccattggg      60
gatattgtga tgactcaggc tgcaccctct gtacctgtca ctcctggaga gtcagtatcc     120
atctcctgca ggtctagtaa gagtctcctg catagtaacg gcaacacttt cttgtattgg     180
ttcctacaga ggccaggcca gtctcctcag ctcctgatat atcggatgtc caaccttgcc     240
tcaggagtcc cagacaggtt cagtggcagt gggtcaggaa ctgctttcac actgagagtc     300
agtagagtgg aggctgagga tgtgggtatt tattactgta tgcaacatct agaatatccg     360
tacacgttcg gaggggggac caagctggaa ataaaa                               396

<210> SEQ ID NO 11
<211> LENGTH: 135
<212> TYPE: PRT
<213> ORGANISM: Mus musculus
<220> FEATURE:
<223> OTHER INFORMATION: Protein sequence of antibody 2-8 VH

<400> SEQUENCE: 11

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Lys Glu Tyr Tyr Met His Trp Val Lys Gln Arg Pro Glu Gln Gly Leu
    50                  55                  60

Glu Trp Ile Gly Trp Ile Asp Pro Glu Asn Gly Asp Thr Ile Tyr Asp
65                  70                  75                  80

Pro Lys Phe Gln Gly Lys Ala Ser Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Arg Ser Arg Leu Phe Phe Ala Tyr Trp Gly Gln Gly
        115                 120                 125

Thr Leu Val Thr Val Ser Ala
    130                 135

<210> SEQ ID NO 12
<211> LENGTH: 10
<212> TYPE: PRT
<213> ORGANISM: Mus musculus
<220> FEATURE:
<223> OTHER INFORMATION: 2-8 HC CDR-1

<400> SEQUENCE: 12

Gly Phe Asn Ile Lys Glu Tyr Tyr Met His
1               5                   10

<210> SEQ ID NO 13
<211> LENGTH: 17
<212> TYPE: PRT
<213> ORGANISM: Mus musculus
<220> FEATURE:
<223> OTHER INFORMATION: 2-8 HC CDR-2
```

<400> SEQUENCE: 13

Trp Ile Asp Pro Glu Asn Gly Asp Thr Ile Tyr Asp Pro Lys Phe Gln
1               5                   10                  15

Gly

<210> SEQ ID NO 14
<211> LENGTH: 7
<212> TYPE: PRT
<213> ORGANISM: Mus musculus
<220> FEATURE:
<223> OTHER INFORMATION: 2-8 HC CDR-3

<400> SEQUENCE: 14

Ser Arg Leu Phe Phe Ala Tyr
1               5

<210> SEQ ID NO 15
<211> LENGTH: 405
<212> TYPE: DNA
<213> ORGANISM: Mus musculus
<220> FEATURE:
<223> OTHER INFORMATION: Nucleotide sequence of antibody 2-8 VH

<400> SEQUENCE: 15
atgaaatgca gctgggtcat cttcttcctg atggcagtgg ttacaggggt caattcagag      60
gttcagctgc agcagtctgg ggctgaactt gtgaggccag ggccttagt caagttgtcc     120 tgcaaagctt ctggcttcaa cattaaagag tattatatgc attgggtgaa gcagaggcct     180
gaacagggcc tggagtggat tggatggatt gatcctgaga atggtgatac tatatatgac     240
ccgaagttcc agggcaaggc cagtataaca gcagacacat cctccaacac agcctacctg     300
caactcagca gcctgacatc tgaggacact gccgtctatt actgtgctag atcgagacta     360
ttctttgctt actggggcca agggactctg gtcactgtct ctgca                     405

<210> SEQ ID NO 16
<211> LENGTH: 127
<212> TYPE: PRT
<213> ORGANISM: Mus musculus
<220> FEATURE:
<223> OTHER INFORMATION: Protein sequence of antibody 2-8 VL

<400> SEQUENCE: 16

Met Glu Ser Gln Ile Gln Val Leu Val Phe Val Phe Leu Trp Leu Ser
1               5                   10                  15

Gly Val Asp Gly Asp Ile Val Met Thr Gln Ser His Lys Phe Met Ser
                20                  25                  30

Thr Ser Val Gly Asp Arg Val Ser Phe Thr Cys Lys Ala Ser Gln Asp
            35                  40                  45

Val Arg Thr Ala Val Asp Trp Tyr Gln Gln Lys Pro Gly Gln Ser Pro
        50                  55                  60

Lys Leu Leu Ile Tyr Ser Ala Ser Tyr Arg Tyr Thr Gly Val Pro Asp
65                  70                  75                  80

Arg Phe Thr Gly Thr Gly Ser Gly Thr Asp Phe Thr Phe Thr Ile Ser
                85                  90                  95

Ser Val Gln Ala Glu Asp Leu Ala Val Tyr Phe Cys Gln Gln Gln Tyr
                100                 105                 110

Thr Thr Pro Tyr Thr Phe Gly Gly Gly Thr Lys Leu Glu Ile Lys
            115                 120                 125

<210> SEQ ID NO 17
<211> LENGTH: 11
<212> TYPE: PRT
<213> ORGANISM: Mus musculus
<220> FEATURE:
<223> OTHER INFORMATION: 2-8 LC CDR-1

<400> SEQUENCE: 17

Lys Ala Ser Gln Asp Val Arg Thr Ala Val Asp
1               5                   10

<210> SEQ ID NO 18
<211> LENGTH: 7
<212> TYPE: PRT
<213> ORGANISM: Mus musculus
<220> FEATURE:
<223> OTHER INFORMATION: 2-8 LC CDR-2

<400> SEQUENCE: 18

Ser Ala Ser Tyr Arg Tyr Thr
1               5

<210> SEQ ID NO 19
<211> LENGTH: 9
<212> TYPE: PRT
<213> ORGANISM: Mus musculus
<220> FEATURE:
<223> OTHER INFORMATION: 2-8 LC CDR-3

<400> SEQUENCE: 19

Gln Gln Gln Tyr Thr Thr Pro Tyr Thr
1               5

<210> SEQ ID NO 20
<211> LENGTH: 381
<212> TYPE: DNA
<213> ORGANISM: Mus musculus
<220> FEATURE:
<223> OTHER INFORMATION: Nucleotide sequence of antibody 2-8 VL

<400> SEQUENCE: 20
atggagtcac agattcaggt ccttgtattc gtgtttctct ggttgtctgg tgttgacgga      60
gacattgtaa tgacccagtc tcacaaattc atgtccacat cagtaggaga cagggtcagc     120
ttcacctgca aggccagtca ggatgtgcgc actgctgtag actggtatca acagaaacca     180
ggacaatctc ctaaactact gatttactcg gcatcctacc ggtacactgg agtccctgat     240
cgcttcactg gcactggatc tgggacggat ttcactttca ccatcagcag tgtgcaggct     300
gaagacctgg cagtttactt ctgtcagcaa caatatacta ctccgtacac gttcggaggg     360
gggaccaagc tggaaataaa a                                               381

<210> SEQ ID NO 21
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of antibody hz2-7(H1L2) VH

<400> SEQUENCE: 21

Met Asp Pro Lys Gly Ser Leu Ser Trp Arg Ile Leu Leu Phe Leu Ser
1               5                   10                  15

```
Leu Ala Phe Glu Leu Ser Tyr Gly Glu Val Gln Leu Glu Ser Gly
                20                  25                  30
Gly Gly Leu Val Gln Pro Gly Gly Ser Leu Arg Leu Ser Cys Ala Ala
        35                  40                  45
Ser Gly Phe Thr Phe Ser Asn Tyr Phe Met Asn Trp Val Arg Gln Ala
50                  55                  60
Pro Gly Lys Gly Leu Glu Trp Val Ser Glu Ile Arg Leu Lys Phe Thr
65                  70                  75                  80
Asn Tyr Ala Thr His Tyr Ala Asp Ser Val Lys Gly Arg Phe Thr Ile
                85                  90                  95
Ser Arg Asp Asp Ser Lys Ser Thr Leu Tyr Leu Gln Met Asn Ser Leu
            100                 105                 110
Arg Ala Glu Asp Thr Ala Val Tyr Tyr Cys Thr Arg Asp Tyr Gly Ser
        115                 120                 125
Arg Asn Gly Tyr Phe Asp Tyr Trp Gly Gln Gly Thr Leu Val Thr Val
    130                 135                 140
Ser Ser
145

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2) HC CDR-1

<400> SEQUENCE: 22

Gly Phe Thr Phe Ser Asn Tyr Phe Met Asn
1               5                   10

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2) HC CDR-2

<400> SEQUENCE: 23

Glu Ile Arg Leu Lys Phe Thr Asn Tyr Ala Thr His Tyr Ala Asp Ser
1               5                   10                  15
Val Lys Gly

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2) HC CDR-3

<400> SEQUENCE: 24

Asp Tyr Gly Ser Arg Asn Gly Tyr Phe Asp Tyr
1               5                   10

<210> SEQ ID NO 25
```

```
<211> LENGTH: 438
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence of antibody hz2-7(H1L2) VH

<400> SEQUENCE: 25
atggacccca agggcagcct gagctggaga atcctgctgt tcctgagcct ggccttcgag      60
ctgagctacg gcgaggttca gctgctcgag agcggaggtg gtctggtgca gcctggcggt     120
agcctgaggc tgagctgcgc cgcaagcggc tttaccttca gcaactactt tatgaattgg     180
gtgaggcagg caccgggcaa gggcctggag tgggtaagcg agatcaggct gaagttcacc     240
aattacgcta cccattacgc cgacagcgtg aagggccgct tcaccatcag cagggacgac     300
tctaagagca ccctgtacct gcagatgaac tcactgaggg ccgaggacac cgccgtgtac     360
tactgcacta gggactacgg cagcaggaac ggctacttcg actactgggg ccagggcact     420
ctggtcaccg tgagcagc                                                   438

<210> SEQ ID NO 26
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of antibody hz2-7(H1L2) VL

<400> SEQUENCE: 26

Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Pro
            20                  25                  30

Val Thr Pro Gly Glu Pro Ala Ser Ile Ser Cys Arg Ser Ser Lys Ser
        35                  40                  45

Leu Leu His Ser Asn Gly Asn Thr Phe Leu Tyr Trp Phe Leu Gln Lys
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Leu Glu Ile Lys
    130

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2) LC CDR-1

<400> SEQUENCE: 27
```

Arg Ser Ser Lys Ser Leu Leu His Ser Asn Gly Asn Thr Phe Leu Tyr
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2) LC CDR-2

<400> SEQUENCE: 28

Arg Met Ser Asn Leu Ala Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2) LC CDR-3

<400> SEQUENCE: 29

Met Gln His Leu Glu Tyr Pro Tyr Thr
1               5

<210> SEQ ID NO 30
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence of antibody hz2-7(H1L2) VL

<400> SEQUENCE: 30
atggagaccg acaccctgct gctctgggtg ctgctgctct gggtgcccgg ctccaccgga      60
gacatcgtga tgacccagac accctgagc ctgcccgtga cccccggtga gcccgccagc     120
atcagctgca ggtcaagcaa gagcctcctg cacagcaacg gcaacacctt tctgtactgg     180
ttcctgcaga agccgggaca gagcccccag ctgctgatct acaggatgag caacctggcc     240
tctggcgtgc ccgacaggtt cagcggcagt ggcagcggaa ccgacttcac cctgaagatt     300
agcagggtgg aggccgagga cgtgggcgtg tactactgta tgcagcacct ggagtacccc     360
tacaccttcg gcggagggac caaactggaa atcaag                                396

<210> SEQ ID NO 31
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of antibody hz2-7(H1L2 G131A)
      VH

<400> SEQUENCE: 31

Met Asp Pro Lys Gly Ser Leu Ser Trp Arg Ile Leu Leu Phe Leu Ser
1               5                   10                  15

-continued

```
Leu Ala Phe Glu Leu Ser Tyr Gly Glu Val Gln Leu Glu Ser Gly
         20                  25                  30

Gly Gly Leu Val Gln Pro Gly Gly Ser Leu Arg Leu Ser Cys Ala Ala
            35                  40                  45

Ser Gly Phe Thr Phe Ser Asn Tyr Phe Met Asn Trp Val Arg Gln Ala
 50                  55                  60

Pro Gly Lys Gly Leu Glu Trp Val Ser Glu Ile Arg Leu Lys Phe Thr
 65                  70                  75                  80

Asn Tyr Ala Thr His Tyr Ala Asp Ser Val Lys Gly Arg Phe Thr Ile
                 85                  90                  95

Ser Arg Asp Asp Ser Lys Ser Thr Leu Tyr Leu Gln Met Asn Ser Leu
            100                 105                 110

Arg Ala Glu Asp Thr Ala Val Tyr Tyr Cys Thr Arg Asp Tyr Gly Ser
            115                 120                 125

Arg Asn Ala Tyr Phe Asp Tyr Trp Gly Gln Gly Thr Leu Val Thr Val
    130                 135                 140

Ser Ser
145

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2 G131A) HC CDR-1

<400> SEQUENCE: 32

Gly Phe Thr Phe Ser Asn Tyr Phe Met Asn
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2 G131A) HC CDR-2

<400> SEQUENCE: 33

Glu Ile Arg Leu Lys Phe Thr Asn Tyr Ala Thr His Tyr Ala Asp Ser
1               5                   10                  15

Val Lys Gly

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2 G131A) HC CDR-3

<400> SEQUENCE: 34

Asp Tyr Gly Ser Arg Asn Ala Tyr Phe Asp Tyr
1               5                   10
```

<210> SEQ ID NO 35
<211> LENGTH: 438
<212> TYPE: DNA
<213> ORGANISM: Artificial Sequence
<220> FEATURE:
<223> OTHER INFORMATION: Description of Artificial Sequence: Synthetic
   polynucleotide
<220> FEATURE:
<223> OTHER INFORMATION: Nucleotide sequence of antibody hz2-7(H1L2
   G131A) VH

<400> SEQUENCE: 35

```
atggacccca agggcagcct gagctggaga atcctgctgt tcctgagcct ggccttcgag    60
ctgagctacg gcgaggttca gctgctcgag agcggaggtg gtctggtgca gcctggcggt   120
agcctgaggc tgagctgcgc cgcaagcggc tttaccttca gcaactactt tatgaattgg   180
gtgaggcagg caccgggcaa gggcctggag tgggtaagcg agatcaggct gaagttcacc   240
aattacgcta cccattacgc cgacagcgtg aagggccgct tcaccatcag cagggacgac   300
tctaagagca ccctgtacct gcagatgaac tcactgaggg ccgaggacac cgccgtgtac   360
tactgcacta gggactacgg cagcaggaac gcctacttcg actactgggg ccagggcact   420
ctggtcaccg tgagcagc                                                  438
```

<210> SEQ ID NO 36
<211> LENGTH: 132
<212> TYPE: PRT
<213> ORGANISM: Artificial Sequence
<220> FEATURE:
<223> OTHER INFORMATION: Description of Artificial Sequence: Synthetic
   polypeptide
<220> FEATURE:
<223> OTHER INFORMATION: Protein sequence of antibody hz2-7(H1L2 G131A)
   VL

<400> SEQUENCE: 36

```
Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Pro
                20                  25                  30

Val Thr Pro Gly Glu Pro Ala Ser Ile Ser Cys Arg Ser Ser Lys Ser
            35                  40                  45

Leu Leu His Ser Asn Gly Asn Thr Phe Leu Tyr Trp Phe Leu Gln Lys
        50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Leu Glu Ile Lys
    130
```

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
   peptide
<220> FEATURE:

<223> OTHER INFORMATION: hz2-7(H1L2 G131A) LC CDR-1

<400> SEQUENCE: 37

Arg Ser Ser Lys Ser Leu Leu His Ser Asn Gly Asn Thr Phe Leu Tyr
1               5                   10                  15

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2 G131A) LC CDR-2

<400> SEQUENCE: 38

Arg Met Ser Asn Leu Ala Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-7(H1L2 G131A) LC CDR-3

<400> SEQUENCE: 39

Met Gln His Leu Glu Tyr Pro Tyr Thr
1               5

<210> SEQ ID NO 40
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence of antibody hz2-7(H1L2
      G131A) VL

<400> SEQUENCE: 40
atggagaccg acaccctgct gctctgggtg ctgctgctct gggtgcccgg ctccaccgga      60
gacatcgtga tgacccagac acccctgagc ctgcccgtga cccccggtga gcccgccagc     120
atcagctgca ggtcaagcaa gagcctcctg cacagcaacg gcaacacctt tctgtactgg     180
ttcctgcaga agccgggaca gagcccccag ctgctgatct acaggatgag caacctggcc     240
tctggcgtgc ccgacaggtt cagcggcagt ggcagcggaa ccgacttcac cctgaagatt     300
agcagggtgg aggccgagga cgtgggcgtg tactactgta tgcagcacct ggagtacccc     360
tacaccttcg gcggagggac caaactggaa atcaag                               396

<210> SEQ ID NO 41
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of antibody hz2-8(H1L2) VH

<400> SEQUENCE: 41

-continued

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Phe Asn Ile Lys Glu Tyr Tyr Met His Trp Val Arg Gln Ala
    50                  55                  60

Pro Glu Gln Gly Leu Glu Trp Met Gly Trp Ile Asp Pro Glu Asn Gly
65                  70                  75                  80

Asp Thr Ile Tyr Ala Gln Lys Phe Gln Gly Arg Val Thr Ile Thr Ala
                85                  90                  95

Asp Thr Ser Thr Asn Thr Ala Tyr Met Glu Leu Ser Ser Leu Arg Ser
            100                 105                 110

Glu Asp Thr Ala Val Tyr Tyr Cys Ala Arg Ser Arg Leu Phe Phe Ala
        115                 120                 125

Tyr Trp Gly Gln Gly Thr Leu Val Thr Val Ser Ser
    130                 135                 140

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8(H1L2) HC CDR-1

<400> SEQUENCE: 42

Gly Phe Asn Ile Lys Glu Tyr Tyr Met His
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8(H1L2) HC CDR-2

<400> SEQUENCE: 43

Trp Ile Asp Pro Glu Asn Gly Asp Thr Ile Tyr Ala Gln Lys Phe Gln
1               5                   10                  15

Gly

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8(H1L2) HC CDR-3

<400> SEQUENCE: 44

Ser Arg Leu Phe Phe Ala Tyr
1               5
```

```
<210> SEQ ID NO 45
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence of antibody hz2-8(H1L2) VH

<400> SEQUENCE: 45
atggacccca agggcagcct gagctggaga atcctgctgt tcctgagcct ggccttcgag    60
ctgagctacg gccaggtgca gctggtgcag agtggggccg aggtgaagaa gccgggagcc   120
agcgtgaagg tgagctgcaa ggccagcggc ttcaacatca aggagtacta catgcactgg   180
gtgaggcaag cgccggaaca gggcctggag tggatgggct ggatcgaccc cgagaacggc   240
gataccatct acgcccagaa gttccagggc agggtgacca tcaccgctga caccagcacc   300
aacaccgcct acatggagct gagcagcctg agaagcgagg acacagccgt gtactactgc   360
gccaggtcac gcttgttctt cgcctactgg ggccaaggca ccctggtgac cgtgagctct   420

<210> SEQ ID NO 46
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of antibody hz2-8(H1L2) VL

<400> SEQUENCE: 46

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Lys Ser Leu Ser
            20                  25                  30

Ala Ser Val Gly Asp Arg Val Thr Ile Thr Cys Arg Ala Ser Gln Asp
        35                  40                  45

Val Arg Thr Ala Leu Asp Trp Tyr Gln Gln Lys Pro Gly Gln Ser Pro
    50                  55                  60

Lys Leu Leu Ile Tyr Ser Ala Ser Tyr Arg Tyr Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Gln Tyr
            100                 105                 110

Thr Thr Pro Tyr Thr Phe Gly Gln Gly Thr Lys Leu Glu Ile Lys
        115                 120                 125

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8(H1L2) LC CDR-1

<400> SEQUENCE: 47

Arg Ala Ser Gln Asp Val Arg Thr Ala Leu Asp
1               5                   10
```

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8(H1L2) LC CDR-2

<400> SEQUENCE: 48

Ser Ala Ser Tyr Arg Tyr Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8(H1L2) LC CDR-3

<400> SEQUENCE: 49

Gln Gln Gln Tyr Thr Thr Pro Tyr Thr
1               5

<210> SEQ ID NO 50
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence of antibody hz2-8(H1L2) VL

<400> SEQUENCE: 50
atggagaccg acaccctgct gctctgggtg ctgctgctct gggtgcccgg ctccaccgga      60
gacatccaga tgacccaaag cccaaagagc ctgagcgcca gcgtgggcga cagggtgacg     120
atcacctgca gagccagcca ggacgtgagg accgccctgg attggtatca gcagaagccc     180
ggtcagagcc ccaagctcct gatctacagc gcaagctaca ggtacagcgg cgtgcccagc     240
aggttcagcg gctccggcag cggcaccgac ttcactctta ccatcagctc actgcagccc     300
gaggacttcg ccacctacta ctgccagcag cagtacacca ccccctacac cttcggccag     360
ggcaccaagt tggagatcaa g                                               381

<210> SEQ ID NO 51
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of antibody hz2-8 (H1L2 G80A/
      T82A)

<400> SEQUENCE: 51

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

```
Ala Glu Val Lys Lys Pro Gly Ala Ser Val Lys Val Ser Cys Lys Ala
         35                  40                  45

Ser Gly Phe Asn Ile Lys Glu Tyr Tyr Met His Trp Val Arg Gln Ala
 50                  55                  60

Pro Glu Gln Gly Leu Glu Trp Met Gly Trp Ile Asp Pro Glu Asn Ala
 65                  70                  75                  80

Asp Ala Ile Tyr Ala Gln Lys Phe Gln Gly Arg Val Thr Ile Thr Ala
                 85                  90                  95

Asp Thr Ser Thr Asn Thr Ala Tyr Met Glu Leu Ser Ser Leu Arg Ser
                100                 105                 110

Glu Asp Thr Ala Val Tyr Tyr Cys Ala Arg Ser Arg Leu Phe Phe Ala
            115                 120                 125

Tyr Trp Gly Gln Gly Thr Leu Val Thr Val Ser Ser
130                 135                 140
```

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8 (H1L2 G80A/T82A) HC CDR-1

<400> SEQUENCE: 52

```
Gly Phe Asn Ile Lys Glu Tyr Tyr Met His
 1               5                  10
```

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8 (H1L2 G80A/T82A) HC CDR-2

<400> SEQUENCE: 53

```
Trp Ile Asp Pro Glu Asn Ala Asp Ala Ile Tyr Ala Gln Lys Phe Gln
 1               5                  10                  15

Gly
```

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8 (H1L2 G80A/T82A) HC CDR-3

<400> SEQUENCE: 54

```
Ser Arg Leu Phe Phe Ala Tyr
 1               5
```

<210> SEQ ID NO 55
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide

```
<220> FEATURE:
<223> OTHER INFORMATION: Nucleotide sequence of antibody hz2-8 (H1L2
      G80A/T82A) VH

<400> SEQUENCE: 55
atggaccctg agggctctct gtcttggaga atcctgctgt tcctgagcct ggccttcgag     60
ctgtcttatg ccaggtgca gctggtgcag tctggcgccg aagtgaaaaa gcctggcgcc    120
tctgtgaagg tgtcctgcaa ggcctctggc ttcaacatca agaatatta catgcactgg    180 gtccgacagg cccctgagca aggattggaa tggatgggct ggatcgaccc cgagaacgcc    240
gatgccatct acgcccagaa attccagggc agagtgacca tcaccgccga cacctctacc    300
aacaccgcct acatggaact gtccagcctg agatctgagg acaccgccgt gtactactgc    360
gcccggtcca gactgttctt cgcctattgg ggccagggca ccctggtcac agtttcttcc    420

<210> SEQ ID NO 56
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of antibody hz2-8 (H1L2 G80A/
      T82A) VL

<400> SEQUENCE: 56

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Lys Ser Leu Ser
            20                  25                  30

Ala Ser Val Gly Asp Arg Val Thr Ile Thr Cys Arg Ala Ser Gln Asp
        35                  40                  45

Val Arg Thr Ala Leu Asp Trp Tyr Gln Gln Lys Pro Gly Gln Ser Pro
    50                  55                  60

Lys Leu Leu Ile Tyr Ser Ala Ser Tyr Arg Tyr Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Gln Tyr
            100                 105                 110

Thr Thr Pro Tyr Thr Phe Gly Gln Gly Thr Lys Leu Glu Ile Lys
        115                 120                 125

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8 (H1L2 G80A/T82A) LC CDR-1

<400> SEQUENCE: 57

Arg Ala Ser Gln Asp Val Arg Thr Ala Leu Asp
1               5                   10

<210> SEQ ID NO 58
<211> LENGTH: 7
<212> TYPE: PRT
<213> ORGANISM: Artificial Sequence
```

<220> FEATURE:
<223> OTHER INFORMATION: Description of Artificial Sequence: Synthetic
      peptide
<220> FEATURE:
<223> OTHER INFORMATION: hz2-8 (H1L2 G80A/T82A) LC CDR-2

<400> SEQUENCE: 58

Ser Ala Ser Tyr Arg Tyr Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8 (H1L2 G80A/T82A) LC CDR-3

<400> SEQUENCE: 59

Gln Gln Gln Tyr Thr Thr Pro Tyr Thr
1               5

<210> SEQ ID NO 60
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence of antibody hz2-8 (H1L2
      G80A/T82A) VL

<400> SEQUENCE: 60
atggaaaccg acacactgct gctgtgggtg ctgctcttgt gggtgccagg atctaccggc       60
gacatccaga tgacccagtc tccaaagtct ctgtccgcct ccgtgggcga cagagtgacc      120
atcacctgta gagcctctca ggacgtgcgg accgctctgg attggtatca gcagaagcct      180
ggccagtctc ctaagctgct gatctactcc gcctcctacc ggtactctgg cgtgccctcc      240
agattctccg gctctggctc tggcaccgac tttaccctga caatctccag cctgcagcct      300
gaggacttcg ccacctacta ctgccagcaa cagtacacca caccttacac cttcggccag      360
ggcaccaagc tggaaatcaa g                                                381

<210> SEQ ID NO 61
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of antibody hz2-8 (H1L2 G80A)
      VH

<400> SEQUENCE: 61

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
                20                  25                  30

Ala Glu Val Lys Lys Pro Gly Ala Ser Val Lys Val Ser Cys Lys Ala
            35                  40                  45

Ser Gly Phe Asn Ile Lys Glu Tyr Tyr Met His Trp Val Arg Gln Ala

```
                50                  55                  60
Pro Gln Gly Leu Glu Trp Met Gly Trp Ile Asp Pro Glu Asn Ala
65                  70                  75                  80

Asp Thr Ile Tyr Ala Gln Lys Phe Gln Gly Arg Val Thr Ile Thr Ala
                85                  90                  95

Asp Thr Ser Thr Asn Thr Ala Tyr Met Glu Leu Ser Ser Leu Arg Ser
            100                 105                 110

Glu Asp Thr Ala Val Tyr Tyr Cys Ala Arg Ser Arg Leu Phe Phe Ala
        115                 120                 125

Tyr Trp Gly Gln Gly Thr Leu Val Thr Val Ser Ser
        130                 135                 140
```

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8 (H1L2 G80A) HC CDR-1

<400> SEQUENCE: 62

```
Gly Phe Asn Ile Lys Glu Tyr Tyr Met His
1               5                   10
```

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8 (H1L2 G80A) HC CDR-2

<400> SEQUENCE: 63

```
Trp Ile Asp Pro Glu Asn Ala Asp Thr Ile Tyr Ala Gln Lys Phe Gln
1               5                   10                  15

Gly
```

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8 (H1L2 G80A) HC CDR-3

<400> SEQUENCE: 64

```
Ser Arg Leu Phe Phe Ala Tyr
1               5
```

<210> SEQ ID NO 65
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence of antibody hz2-8 (H1L2
      G80A) VH

<400> SEQUENCE: 65

```
atggaccctaa agggctctct gtcttggaga atcctgctgt tcctgagcct ggccttcgag      60
ctgtcttatg ccaggtgca gctggtgcag tctggcgccg aagtgaaaaa gcctggcgcc      120
tctgtgaagg tgtcctgcaa ggcctctggc ttcaacatca agaatatta catgcactgg      180
gtccgacagg cccctgagca aggattggaa tggatgggct ggatcgaccc cgagaacgcc      240
gataccatct acgcccagaa attccagggc agagtgacca tcaccgccga cacctctacc      300
aacaccgcct acatggaact gtccagcctg agatctgagg acaccgccgt gtactactgc      360
gcccggtcca gactgttctt cgcctattgg ggccagggca ccctggtcac agtttcttcc      420
```

<210> SEQ ID NO 66
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Protein sequence of antibody hz2-8 (H1L2 G80A) VL

<400> SEQUENCE: 66

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Lys Ser Leu Ser
            20                  25                  30

Ala Ser Val Gly Asp Arg Val Thr Ile Thr Cys Arg Ala Ser Gln Asp
        35                  40                  45

Val Arg Thr Ala Leu Asp Trp Tyr Gln Gln Lys Pro Gly Gln Ser Pro
    50                  55                  60

Lys Leu Leu Ile Tyr Ser Ala Ser Tyr Arg Tyr Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Gln Tyr
            100                 105                 110

Thr Thr Pro Tyr Thr Phe Gly Gln Gly Thr Lys Leu Glu Ile Lys
        115                 120                 125
```

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: hz2-8 (H1L2 G80A) LC CDR-1

<400> SEQUENCE: 67

```
Arg Ala Ser Gln Asp Val Arg Thr Ala Leu Asp
1               5                   10
```

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:

<223> OTHER INFORMATION: hz2-8 (H1L2 G80A) LC CDR-2

<400> SEQUENCE: 68

Ser Ala Ser Tyr Arg Tyr Ser
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hz2-8 (H1L2 G80A) LC CDR-3

<400> SEQUENCE: 69

Gln Gln Gln Tyr Thr Thr Pro Tyr Thr
1               5

<210> SEQ ID NO 70
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence of antibody hz2-8 (H1L2
      G80A) VL

<400> SEQUENCE: 70
atggaaaccg acacactgct gctgtgggtg ctgctcttgt gggtgccagg atctaccggc      60
gacatccaga tgacccagtc tccaaagtct ctgtccgcct ccgtgggcga cagagtgacc     120
atcacctgta gagcctctca ggacgtgcgg accgctctgg attggtatca gcagaagcct     180
ggccagtctc ctaagctgct gatctactcc gcctcctacc ggtactctgg cgtgccctcc     240
agattctccg gctctggctc tggcaccgac tttaccctga caatctccag cctgcagcct     300
gaggacttcg ccacctacta ctgccagcaa cagtacacca caccttacac cttcggccag     360
ggcaccaagc tggaaatcaa g                                               381

<210> SEQ ID NO 71
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full length antibody 2-7 HC protein sequence

<400> SEQUENCE: 71

Met Tyr Leu Gly Leu Asn Cys Val Phe Ile Val Phe Leu Leu Lys Gly
1               5                   10                  15

Val Gln Ser Glu Val Lys Leu Glu Glu Ser Gly Gly Gly Leu Val Pro
            20                  25                  30

Pro Gly Gly Ser Met Lys Leu Ser Cys Val Ala Ser Gly Phe Thr Phe
        35                  40                  45

Ser Asn Tyr Phe Met Asn Trp Val Arg Gln Ser Pro Glu Lys Gly Leu
    50                  55                  60

Glu Trp Val Ala Glu Ile Arg Leu Lys Phe Thr Asn Tyr Ala Thr His
65                  70                  75                  80

Tyr Ala Glu Ser Val Glu Gly Arg Phe Thr Ile Ser Arg Asp Asp Ser
            85                  90                  95

Lys Ser Ser Val Tyr Leu Gln Met Asn Asn Leu Arg Ala Glu Asp Thr
           100                 105                 110

Gly Ile Tyr Tyr Cys Thr Arg Asp Tyr Gly Ser Arg Asn Gly Tyr Phe
           115                 120                 125

Asp Tyr Trp Gly Gln Gly Thr Thr Leu Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
        210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 72
<211> LENGTH: 1413
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full length antibody 2-7 HC nucleotide sequence

<400> SEQUENCE: 72

```
atgtacttgg gactgaactg tgtattcata gtttttctct taaaaggtgt ccagagtgaa     60
gtgaagcttg aggagtctgg aggaggcttg gtgccacctg gaggatccat gaaactctcc    120
tgtgttgcct ctggattcac tttcagtaac tactttatga actgggtccg ccagtctcca    180 gagaagggc ttgagtgggt tgctgaaatt agattgaaat ttactaatta tgcaacacat    240
tatgcggagt ctgtggaagg gaggttcacc atctcaagag atgattccaa agtagtgtc    300 tacctccaaa tgaacaactt aagagctgaa gacactggca tttattactg taccagggac    360
tacggtagta ggaatgggta ctttgactac tggggccaag caccactct cacagtctcc    420 tcagccagca ccaagggccc ttccgtgttt ccactggccc cctcctctaa atccacatct    480
ggcggcaccg ccgccctggg ctgtctggtg aaggactact cccagagcc tgtgacagtg    540 tcctggaact ctggcgccct gacatccggc gtgcacacat tccagccgt gctgcagagc    600 tccggcctgt acagcctgtc tagcgtggtg acagtgccct cctctagcct gggcacacag    660
acctatatct gcaacgtgaa tcacaagcca agcaatacca aggtggacaa gaaggtggag    720
cccaagtcct gtgataagac acacctgc ccccttgtc ctgctcccga gctgctgggc    780
ggccctagcg tgttcctgtt ccacccaag cctaaggaca ccctgatgat ctcccggaca    840
cccgaggtga cctgcgtggt ggtggacgtg tctcacgagg atcctgaggt gaagttcaac    900
tggtatgtgg atggcgtgga ggtgcacaat gccaagacca gcccagaga ggagcagtac    960 aactctacat ataggggtgg gagcgtgctg accgtgctgc accaggactg gctgaacggc   1020
aaggagtata gtgcaaggt gtccaataag gccctgcccg cccccatcga aagacaatc    1080 agcaaggcca agggccagcc tcgggagcca caggtgtaca ccctgcctcc atccagagac   1140
gagctgacaa agaaccaggt gtctctgaca tgtctggtga agggcttcta tcctagcgat   1200
atcgccgtgg agtgggagtc caatggccag ccagagaaca attacaagac cacacccct    1260 gtgctggact ccgatggctc cttctttctg tattccaagc tgaccgtgga taagtctcgg   1320
tggcagcagg gcaacgtgtt cagctgttcc gtgatgcacg aagccctgca taatcactat   1380
actcagaaat ccctgtccct gtcacctgga aag                                1413
```

<210> SEQ ID NO 73
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full-length antibody 2-7 LC protein sequence

<400> SEQUENCE: 73

```
Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
                20                  25                  30

Val Thr Pro Gly Glu Ser Val Ser Ile Ser Cys Arg Ser Ser Lys Ser
            35                  40                  45
```

Leu Leu His Ser Asn Gly Asn Thr Phe Leu Tyr Trp Phe Leu Gln Arg
 50                  55                  60

Pro Gly Gln Ser Pro Gln Leu Leu Ile Tyr Arg Met Ser Asn Leu Ala
 65                  70                  75                  80

Ser Gly Val Pro Asp Arg Phe Ser Gly Ser Gly Ser Gly Thr Ala Phe
                 85                  90                  95

Thr Leu Arg Val Ser Arg Val Glu Ala Glu Asp Val Gly Ile Tyr Tyr
            100                 105                 110

Cys Met Gln His Leu Glu Tyr Pro Tyr Thr Phe Gly Gly Gly Thr Lys
            115                 120                 125

Leu Glu Ile Lys Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 74
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full-length antibody 2-7 LC nucleotide sequence

<400> SEQUENCE: 74
atgaggtgcc tagctgagtt cctggggctg cttgtgctct ggatccctgg agccattggg      60
gatattgtga tgactcaggc tgcaccctct gtacctgtca ctcctggaga gtcagtatcc     120
atctcctgca ggtctagtaa gagtctcctg catagtaacg gcaacacttt cttgtattgg     180
ttcctacaga ggccaggcca gtctcctcag ctcctgatat atcggatgtc aaccttgcc      240 tcaggagtcc cagacaggtt cagtggcagt gggtcaggaa ctgctttcac actgagagtc     300
agtagagtgg aggctgagga tgtgggtatt tattactgta tgcaacatct agaatatccg     360
tacacgttcg gaggggggac caagctggaa ataaaaacag tggccgcccc aagcgtgttc     420
atctttcccc cttccgacga gcagctgaag tctggcaccg ccagcgtggt gtgcctgctg     480
aacaacttct accctcggga ggccaaggtc cagtggaagg tggataacgc cctgcagtct     540
ggcaatagcc aggagtccgt gaccgagcag gactctaagg atagcacata tccctgtct     600 agcaccctga cactgagcaa ggccgattac gagaagcaca aggtgtatgc ctgtgaagtc     660
acccatcagg gcctgtcatc acccgtcact aagtcattca tcgcggagaa atgc          714

<210> SEQ ID NO 75
<211> LENGTH: 465
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: Full length antibody 2-8 HC protein sequence

<400> SEQUENCE: 75

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Lys Glu Tyr Tyr Met His Trp Val Lys Gln Arg Pro Glu Gln Gly Leu
    50                  55                  60

Glu Trp Ile Gly Trp Ile Asp Pro Glu Asn Gly Asp Thr Ile Tyr Asp
65                  70                  75                  80

Pro Lys Phe Gln Gly Lys Ala Ser Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Arg Ser Arg Leu Phe Phe Ala Tyr Trp Gly Gln Gly
        115                 120                 125

Thr Leu Val Thr Val Ser Ala Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

-continued

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 76
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full length antibody 2-8 HC nucleotide sequence

<400> SEQUENCE: 76
atgaaatgca gctgggtcat cttcttcctg atggcagtgg ttacaggggt caattcagag      60
gttcagctgc agcagtctgg ggctgaactt gtgaggccag ggccttagt caagttgtcc     120 tgcaaagctt ctggcttcaa cattaaagag tattatatgc attgggtgaa gcagaggcct     180
gaacagggcc tggagtggat tggatggatt gatcctgaga atggtgatac tatatatgac     240
ccgaagttcc agggcaaggc cagtataaca gcagacacat cctccaacac agcctacctg     300
caactcagca gcctgacatc tgaggacact gccgtctatt actgtgctag atcgagacta     360
ttctttgctt actggggcca agggactctg gtcactgtct ctgcagccag caccaagggc     420
ccttccgtgt tccactggc ccctcctct aaatccacat ctggcggcac cgccgccctg     480
ggctgtctgg tgaaggacta cttcccagag cctgtgacag tgtcctggaa ctctggcgcc     540
ctgacatccg gcgtgcacac atttccagcc gtgctgcaga gctccggcct gtacagcctg     600
tctagcgtgg tgacagtgcc ctcctctagc ctgggcacac agacctatat ctgcaacgtg     660
aatcacaagc caagcaatac caaggtggac aagaaggtgg agcccaagtc ctgtgataag     720
acacacacct gccccccttg tcctgctccc gagctgctgg gcggccctag cgtgttcctg     780
tttccaccca gcctaagga caccctgatg atctcccgga cacccgaggt gacctgcgtg     840
gtggtggacg tgtctcacga ggatcctgag gtgaagttca ctggtatgt ggatggcgtg     900 gaggtgcaca atgccaagac caagcccaga gaggagcagt acaactctac atataggtg     960 gtgagcgtgc tgaccgtgct gcaccaggac tggctgaacg gcaaggagta taagtgcaag    1020
gtgtccaata aggccctgcc cgcccccatc gagaagacaa tcagcaaggc caagggccag    1080
cctcgggagc acaggtgta caccctgcct ccatccagag acgagctgac aaagaaccag    1140
gtgtctctga catgtctggt gaagggcttc tatcctagcg atatcgccgt ggagtgggag    1200
tccaatggcc agccagagaa caattacaag accacacccc ctgtgctgga ctccgatggc    1260
tccttctttc tgtattccaa gctgaccgtg gataagtctc ggtggcagca gggcaacgtg    1320
ttcagctgtt ccgtgatgca cgaagccctg cataatcact atactcagaa atccctgtcc    1380
ctgtcacctg gaaag                                                      1395
```

<210> SEQ ID NO 77
<211> LENGTH: 233
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Full-length antibody 2-8 LC protein sequence

<400> SEQUENCE: 77

```
Met Glu Ser Gln Ile Gln Val Leu Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Phe Thr Cys Lys Ala Ser Gln Asp
        35                  40                  45

Val Arg Thr Ala Val Asp Trp Tyr Gln Gln Lys Pro Gly Gln Ser Pro
    50                  55                  60

Lys Leu Leu Ile Tyr Ser Ala Ser Tyr Arg Tyr Thr Gly Val Pro Asp
65                  70                  75                  80

Arg Phe Thr Gly Thr Gly Ser Gly Thr Asp Phe Thr Phe Thr Ile Ser
                85                  90                  95

Ser Val Gln Ala Glu Asp Leu Ala Val Tyr Phe Cys Gln Gln Tyr
            100                 105                 110

Thr Thr Pro Tyr Thr Phe Gly Gly Gly Thr Lys Leu Glu Ile Lys Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 78
<211> LENGTH: 699
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Full-length antibody 2-8 LC nucleotide sequence

<400> SEQUENCE: 78

```
atggagtcac agattcaggt ccttgtattc gtgtttctct ggttgtctgg tgttgacgga      60
gacattgtaa tgacccagtc tcacaaattc atgtccacat cagtaggaga cagggtcagc     120
ttcacctgca aggccagtca ggatgtgcgc actgctgtag actggtatca acagaaacca     180
ggacaatctc ctaaactact gatttactcg gcatcctacc ggtacactgg agtccctgat     240
```

```
cgcttcactg gcactggatc tgggacggat ttcactttca ccatcagcag tgtgcaggct    300
gaagacctgg cagtttactt ctgtcagcaa caatatacta ctccgtacac gttcggaggg    360
gggaccaagc tggaaataaa aacagtggcc gccccaagcg tgttcatctt tccccttcc    420 gacgagcagc tgaagtctgg caccgccagc gtggtgtgcc tgctgaacaa cttctaccct    480
cgggaggcca aggtccagtg gaaggtggat aacgccctgc agtctggcaa tagccaggag    540
tccgtgaccg agcaggactc taaggatagc acatattccc tgtctagcac cctgacactg    600
agcaaggccg attacgagaa gcacaaggtg tatgcctgtg aagtcaccca tcagggctg    660 tcatcacccg tcactaagtc attcaatcgc ggagaatgc                          699
```

<210> SEQ ID NO 79
<211> LENGTH: 475
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Full length antibody hz2-7(H1L2) HC protein sequence

<400> SEQUENCE: 79

```
Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Leu Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Asn Tyr Phe Met Asn Trp Val Arg Gln Ala
    50                  55                  60

Pro Gly Lys Gly Leu Glu Trp Val Ser Glu Ile Arg Leu Lys Phe Thr
65                  70                  75                  80

Asn Tyr Ala Thr His Tyr Ala Asp Ser Val Lys Gly Arg Phe Thr Ile
                85                  90                  95

Ser Arg Asp Asp Ser Lys Ser Thr Leu Tyr Leu Gln Met Asn Ser Leu
            100                 105                 110

Arg Ala Glu Asp Thr Ala Val Tyr Tyr Cys Thr Arg Asp Tyr Gly Ser
        115                 120                 125

Arg Asn Gly Tyr Phe Asp Tyr Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
```

```
                    260                 265                 270
Pro Pro Lys Pro Lys Asp Thr Leu Met Ile Ser Arg Thr Pro Glu Val
            275                 280                 285
Thr Cys Val Val Asp Val Ser His Glu Asp Pro Glu Val Lys Phe
        290                 295                 300
Asn Trp Tyr Val Asp Gly Val Glu Val His Asn Ala Lys Thr Lys Pro
305                 310                 315                 320
Arg Glu Glu Gln Tyr Asn Ser Thr Tyr Arg Val Val Ser Val Leu Thr
                325                 330                 335
Val Leu His Gln Asp Trp Leu Asn Gly Lys Glu Tyr Lys Cys Lys Val
            340                 345                 350
Ser Asn Lys Ala Leu Pro Ala Pro Ile Glu Lys Thr Ile Ser Lys Ala
        355                 360                 365
Lys Gly Gln Pro Arg Glu Pro Gln Val Tyr Thr Leu Pro Pro Ser Arg
    370                 375                 380
Glu Glu Met Thr Lys Asn Gln Val Ser Leu Thr Cys Leu Val Lys Gly
385                 390                 395                 400
Phe Tyr Pro Ser Asp Ile Ala Val Glu Trp Glu Ser Asn Gly Gln Pro
                405                 410                 415
Glu Asn Asn Tyr Lys Thr Thr Pro Pro Val Leu Asp Ser Asp Gly Ser
            420                 425                 430
Phe Phe Leu Tyr Ser Lys Leu Thr Val Asp Lys Ser Arg Trp Gln Gln
        435                 440                 445
Gly Asn Val Phe Ser Cys Ser Val Met His Glu Ala Leu His Asn His
    450                 455                 460
Tyr Thr Gln Lys Ser Leu Ser Leu Ser Pro Gly
465                 470                 475

<210> SEQ ID NO 80
<211> LENGTH: 1428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full length antibody hz2-7(H1L2) HC nucleotide
      sequence

<400> SEQUENCE: 80
atggacccca agggcagcct gagctggaga atcctgctgt tcctgagcct ggccttcgag      60
ctgagctacg cgaggttca gctgctcgag agcggaggtg gtctggtgca gcctggcggt      120
agcctgaggc tgagctgcgc cgcaagcggc tttaccttca gcaactactt tatgaattgg     180
gtgaggcagg caccgggcaa gggcctggag tgggtaagcg agatcaggct gaagttcacc     240
aattacgcta cccattacgc cgacagcgtg aagggccgct tcaccatcag cagggacgac     300
tctaagagca ccctgtacct gcagatgaac tcactgaggg ccgaggacac cgccgtgtac     360
tactgcacta gggactacgg cagcaggaac ggctacttcg actactgggg ccagggcact     420
ctggtcaccg tgagcagcgc tagcaccaag ggccccagcg tgttccctct ggccccagc     480 agcaagagca ccagcggcgg aaccgccgcc ctgggctgcc tggtgaagga ctacttcccc     540
gagcccgtga ccgtgtcctg aacagcggc gctctgacca gcggagtgca caccttccct     600
gccgtgctgc agagcagcgg cctgtactcc ctgagcagcg tggtgaccgt gcccagcagc     660
agcctgggca cccagaccta catctgcaac gtgaaccaca gccctccaa caccaaggtg     720
```

```
gacaagaagg tggagcctaa gagctgcgac aagacccaca cctgccctcc ctgccccgcc      780
cccgagctgc tgggcggacc cagcgtgttc ctgttccctc caagcccaa ggacaccctg       840 atgatcagcc gcaccccga ggtgacctgc gtggtggtgg acgtgagcca cgaggacccc       900
gaggtgaagt tcaactggta cgtggacggc gtggaggtgc acaacgccaa gaccaagcct      960
cgggaggagc agtacaactc cacctaccgc gtggtgagcg tgctgaccgt gctgcaccag     1020
gactggctga acggcaagga gtacaagtgc aaggtgagca acaaggccct gcccgctccc     1080
atcgagaaga ccatcagcaa ggccaagggc cagccccggg agcctcaggt gtacaccctg     1140 cccccagcc gcgaagagat gaccaagaac caggtgagcc tgacctgcct ggtgaagggc      1200 ttctaccct ccgacatcgc cgtggagtgg gagagcaacg gccagcctga aacaactac       1260 aagaccaccc ctcccgtgct ggacagcgac ggcagcttct tcctgtacag caagctgacc     1320
gtggacaagt cccggtggca gcaggcaac gtgttcagct gcagcgtgat gcacgaggcc      1380
ctgcacaacc actacaccca gaagagcctg agcctgagcc ccggatag                  1428
```

<210> SEQ ID NO 81
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Full-length antibody hz2-7(H1L2) LC protein sequence

<400> SEQUENCE: 81

```
Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Pro
            20                  25                  30

Val Thr Pro Gly Glu Pro Ala Ser Ile Ser Cys Arg Ser Ser Lys Ser
        35                  40                  45

Leu Leu His Ser Asn Gly Asn Thr Phe Leu Tyr Trp Phe Leu Gln Lys
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220
```

Gly Leu Ser Ser Pro Val Thr Lys Ser Phe Asn Arg Gly Glu Cys
225                 230                 235

<210> SEQ ID NO 82
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full-length antibody hz2-7(H1L2) LC nucleotide
      sequence

<400> SEQUENCE: 82
atggagaccg acaccctgct gctctgggtg ctgctgctct gggtgcccgg ctccaccgga    60
gacatcgtga tgacccagac ccccctgagc ctgcccgtga ccccggtga gcccgccagc   120 atcagctgca ggtcaagcaa gagcctcctc cacagcaacg caacaccctt tctgtactgg   180
ttcctgcaga agccgggaca gagcccccag ctgctgatct acaggatgag caacctggcc   240
tctggcgtgc ccgacaggtt cagcggcagt ggcagcggaa ccgacttcac cctgaagatt   300
agcagggtgg aggccgagga cgtgggcgtg tactactgta tgcagcacct ggagtacccc   360
tacaccttcg gcggagggac caaactggaa atcaagcgga ccgtggccgc ccccagcgtg   420
ttcatcttcc ctcccagcga cgagcagctg aagtctggca ccgccagcgt ggtgtgcctg   480
ctgaacaact ctaccccccg cgaggccaag gtgcagtgga aggtggacaa cgccctgcag   540
agcggcaaca gccaggagag cgtgaccgag caggactcca aggacagcac ctacagcctg   600
agcagcaccc tgaccctgag caaggccgac tacgagaagc acaaggtgta cgcctgcgag   660
gtgacccacc agggactgtc tagccccgtg accaagagct tcaaccgggg cgagtgctaa   720

<210> SEQ ID NO 83
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full length antibody hz2-7(H1L2 G131A) HC
      protein sequence

<400> SEQUENCE: 83

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Leu Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Asn Tyr Phe Met Asn Trp Val Arg Gln Ala
    50                  55                  60

Pro Gly Lys Gly Leu Glu Trp Val Ser Glu Ile Arg Leu Lys Phe Thr
65                  70                  75                  80

Asn Tyr Ala Thr His Tyr Ala Asp Ser Val Lys Gly Arg Phe Thr Ile
                85                  90                  95

Ser Arg Asp Asp Ser Lys Ser Thr Leu Tyr Leu Gln Met Asn Ser Leu
            100                 105                 110

Arg Ala Glu Asp Thr Ala Val Tyr Tyr Cys Thr Arg Asp Tyr Gly Ser
        115                 120                 125

```
Arg Asn Ala Tyr Phe Asp Tyr Trp Gly Gln Gly Thr Leu Val Thr Val
            130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly
465                 470                 475

<210> SEQ ID NO 84
<211> LENGTH: 1428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full length antibody hz2-7(H1L2 G131A) HC
      nucleotide sequence
```

<400> SEQUENCE: 84

```
atggacccca agggcagcct gagctggaga atcctgctgt tcctgagcct ggccttcgag      60
ctgagctacg gcgaggttca gctgctcgag agcggaggtg gtctggtgca gcctggcggt     120
agcctgaggc tgagctgcgc cgcaagcggc tttaccttca gcaactactt tatgaattgg     180
gtgaggcagg caccgggcaa gggcctggag tgggtaagcg agatcaggct gaagttcacc     240
aattacgcta cccattacgc cgacagcgtg aagggccgct tcaccatcag cagggacgac     300
tctaagagca ccctgtacct gcagatgaac tcactgaggg ccgaggacac cgccgtgtac     360
tactgcacta gggactacgg cagcaggaac gcctacttcg actactgggg ccagggcact     420
ctggtcaccg tgagcagcgc tagcaccaag ggccccagcg tgttccctct ggcccccagc     480
agcaagagca ccagcggcgg aaccgccgcc ctgggctgcc tggtgaagga ctacttcccc     540
gagcccgtga ccgtgtcctg gaacagcggc gctctgacca gcggagtgca caccttccct     600
gccgtgctgc agagcagcgg cctgtactcc ctgagcagcg tggtgaccgt gccccagcag     660
agcctgggca cccagaccta catctgcaac gtgaaccaca agccctccaa caccaaggtg     720
gacaagaagg tggagcctaa gagctgcgac aagacccaca cctgccctcc ctgccccgcc     780
cccgagctgc tgggcggacc cagcgtgttc ctgttccctc ccaagcccaa ggacaccctg     840
atgatcagcc gcaccccga ggtgacctgc gtggtggtgg acgtgagcca cgaggacccc     900
gaggtgaagt tcaactggta cgtggacggc gtggaggtgc acaacgccaa gaccaagcct     960
cgggaggagc agtacaactc cacctaccgc gtggtgagcg tgctgaccgt gctgcaccag    1020
gactggctga acggcaagga gtacaagtgc aaggtgagca caaggccct gcccgctccc    1080
atcgagaaga ccatcagcaa ggccaagggc cagccccggg agcctcaggt gtacaccctg    1140
ccccccagcc gcgaagagat gaccaagaac caggtgagcc tgacctgcct ggtgaagggc    1200
ttctacccct ccgacatcgc cgtggagtgg gagagcaacg gccagcctga gaacaactac    1260
aagaccaccc ctcccgtgct ggacagcgac ggcagcttct tcctgtacag caagctgacc    1320
gtggacaagt cccggtggca gcagggcaac gtgttcagct gcagcgtgat gcacgaggcc    1380
ctgcacaacc actacaccca gaagagcctg agcctgagcc ccggatag              1428
```

<210> SEQ ID NO 85
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Full-length antibody hz2-7(H1L2 G131A) LC protein sequence

<400> SEQUENCE: 85

```
Met Glu Thr Asp Thr Leu Leu Leu Trp Val Leu Leu Leu Trp Val Pro
  1               5                  10                  15

Gly Ser Thr Gly Asp Ile Val Met Thr Gln Thr Pro Leu Ser Leu Pro
                 20                  25                  30

Val Thr Pro Gly Glu Pro Ala Ser Ile Ser Cys Arg Ser Ser Lys Ser
             35                  40                  45

Leu Leu His Ser Asn Gly Asn Thr Phe Leu Tyr Trp Phe Leu Gln Lys
         50                  55                  60

Pro Gly Gln Ser Pro Gln Leu Leu Ile Tyr Arg Met Ser Asn Leu Ala
 65                  70                  75                  80
```

Ser Gly Val Pro Asp Arg Phe Ser Gly Ser Gly Ser Gly Thr Asp Phe
            85                  90                  95

Thr Leu Lys Ile Ser Arg Val Glu Ala Glu Asp Val Gly Val Tyr Tyr
        100                 105                 110

Cys Met Gln His Leu Glu Tyr Pro Tyr Thr Phe Gly Gly Gly Thr Lys
    115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 86
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full-length antibody hz2-7(H1L2 G131A) LC
      nucleotide sequence

<400> SEQUENCE: 86
atggagaccg acaccctgct gctctgggtg ctgctgctct gggtgcccgg ctccaccgga      60
gacatcgtga tgacccagac acccctgagc ctgcccgtga ccccggtga gcccgccagc     120 atcagctgca ggtcaagcaa gagcctcctg cacagcaacg gcaacacctt tctgtactgg    180
ttcctgcaga agccgggaca gagcccccag ctgctgatct acaggatgag caacctggcc    240
tctggcgtgc ccgacaggtt cagcggcagt ggcagcggaa ccgacttcac cctgaagatt    300
agcagggtgg aggccgagga cgtgggcgtg tactactgta tgcagcacct ggagtacccc    360
tacaccttcg gcggagggac caaactggaa atcaagcgga ccgtggccgc ccccagcgtg    420
ttcatcttcc ctcccagcga cgagcagctg aagtctggca ccgccagcgt ggtgtgcctg    480 ctgaacaact␣tctaccccg cgaggccaag gtgcagtgga aggtggacaa cgccctgcag    540
agcggcaaca gccaggagag cgtgaccgag caggactcca aggacagcac ctacagcctg    600
agcagcaccc tgaccctgag caaggccgac tacgagaagc acaaggtgta cgcctgcgag    660
gtgacccacc agggactgtc tagccccgtg accaagagct tcaaccgggg cgagtgctaa    720

<210> SEQ ID NO 87
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full length antibody hz2-8(H1L2) HC protein
      sequence

<400> SEQUENCE: 87

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Phe Asn Ile Lys Glu Tyr Tyr Met His Trp Val Arg Gln Ala
    50                  55                  60

Pro Glu Gln Gly Leu Glu Trp Met Gly Trp Ile Asp Pro Glu Asn Gly
65                  70                  75                  80

Asp Thr Ile Tyr Ala Gln Lys Phe Gln Gly Arg Val Thr Ile Thr Ala
                85                  90                  95

Asp Thr Ser Thr Asn Thr Ala Tyr Met Glu Leu Ser Ser Leu Arg Ser
            100                 105                 110

Glu Asp Thr Ala Val Tyr Cys Ala Arg Ser Arg Leu Phe Phe Ala
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
```

```
                    405                 410                 415
Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly
465

<210> SEQ ID NO 88
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full length antibody hz2-8(H1L2) HC nucleotide
      sequence

<400> SEQUENCE: 88
atggacccca agggcagcct gagctggaga atcctgctgt cctgagcct ggccttcgag     60 ctgagctacg ccaggtgca gctggtgcag agtggggccg aggtgaagaa gccgggagcc    120
agcgtgaagg tgagctgcaa ggccagcggc ttcaacatca ggagtacta catgcactgg    180 gtgaggcaag cgccggaaca gggcctggag tggatgggct ggatcgaccc cgagaacggc    240
gataccatct acgcccagaa gttccagggc agggtgacca tcaccgctga caccagcacc    300
aacaccgcct acatggagct gagcagcctg agaagcgagg acacagccgt gtactactgc    360
gccaggtcac gcttgttctt cgcctactgg ggccaaggca ccctggtgac cgtgagctct    420
gctagcacca agggcccag cgtgttccct ctggcccca gcagcaagag caccagcggc    480
ggaaccgccg ccctgggctg cctggtgaag gactacttcc ccgagcccgt gaccgtgtcc    540
tggaacagcg gcgctctgac cagcggagtg cacaccttcc ctgccgtgct gcagagcagc    600
ggcctgtact ccctgagcag cgtggtgacc gtgcccagca gcagcctggg cacccagacc    660
tacatctgca acgtgaacca caagccctcc aacaccaagg tggacaagaa ggtggagcct    720
aagagctgcg acaagaccca cacctgccct cctgcccg cccccgagct gctgggcgga    780
cccagcgtgt tcctgttccc tcccaagccc aaggacaccc tgatgatcag ccgcaccccc    840
gaggtgacct gcgtggtggt ggacgtgagc cacgaggacc ccgaggtgaa gttcaactgg    900
tacgtggacg gcgtggaggt gcacaacgcc aagaccaagc ctcgggagga gcagtacaac    960
tccacctacc gcgtggtgag cgtgctgacc gtgctgcacc aggactggct gaacggcaag   1020
gagtacaagt gcaaggtgag caacaaggcc ctgcccgctc ccatcgagaa gaccatcagc   1080
aaggccaagg gccagccccg ggagcctcag gtgtacaccc tgcccccag ccgcgaagag   1140 atgaccaaga accaggtgag cctgacctgc ctggtgaagg cttctaccc ctccgacatc   1200 gccgtggagt gggagagcaa cggccagcct gagaacaact acaagaccac ccctcccgtg   1260
ctggacagcg acggcagctt cttcctgtac agcaagctga ccgtggacaa gtcccggtgg   1320
cagcagggca acgtgttcag ctgcagcgtg atgcacgagg ccctgcacaa ccactacacc   1380
cagaagagcc tgagcctgag ccccggatag                                    1410

<210> SEQ ID NO 89
<211> LENGTH: 234
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full-length antibody hz2-8(H1L2) LC protein
      sequence

<400> SEQUENCE: 89
```

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Lys Ser Leu Ser
            20                  25                  30

Ala Ser Val Gly Asp Arg Val Thr Ile Thr Cys Arg Ala Ser Gln Asp
        35                  40                  45

Val Arg Thr Ala Leu Asp Trp Tyr Gln Gln Lys Pro Gly Gln Ser Pro
50                  55                  60

Lys Leu Leu Ile Tyr Ser Ala Ser Tyr Arg Tyr Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Gln Tyr
            100                 105                 110

Thr Thr Pro Tyr Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

```
<210> SEQ ID NO 90
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full-length antibody hz2-8(H1L2) LC nucleotide
      sequence

<400> SEQUENCE: 90
```
atggagaccg acaccctgct gctctgggtg ctgctgctct gggtgcccgg ctccaccgga      60
gacatccaga tgacccaaag cccaaagagc ctgagcgcca gcgtgggcga cagggtgacg     120
atcacctgca gagccagcca ggacgtgagg accgccctgg attggtatca gcagaagccc     180
ggtcagagcc ccaagctcct gatctacagc gcaagctaca gtacagcgg cgtgcccagc      240 aggttcagcg gctccggcag cggcaccgac ttcactctta ccatcagctc actgcagccc     300

```
gaggacttcg ccacctacta ctgccagcag cagtacacca cccctacac cttcggccag    360 ggcaccaagt tggagatcaa gcggaccgtg gccgccccca gcgtgttcat cttccctccc    420
agcgacgagc agctgaagtc tggcaccgcc agcgtggtgt gcctgctgaa caacttctac    480
ccccgcgagg ccaaggtgca gtggaaggtg acaacgccc tgcagagcgg caacagccag    540
gagagcgtga ccgagcagga ctccaaggac agcacctaca gcctgagcag caccctgacc    600
ctgagcaagg ccgactacga aagcacaag gtgtacgcct gcgaggtgac ccaccaggga    660
ctgtctagcc ccgtgaccaa gagcttcaac cggggcgagt gctaa              705
```

<210> SEQ ID NO 91
<211> LENGTH: 469
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Full length antibody hz2-8 (H1L2 G80A/T82A) HC protein sequence

<400> SEQUENCE: 91

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Phe Asn Ile Lys Glu Tyr Tyr Met His Trp Val Arg Gln Ala
    50                  55                  60

Pro Glu Gln Gly Leu Glu Trp Met Gly Trp Ile Asp Pro Glu Asn Ala
65                  70                  75                  80

Asp Ala Ile Tyr Ala Gln Lys Phe Gln Gly Arg Val Thr Ile Thr Ala
                85                  90                  95

Asp Thr Ser Thr Asn Thr Ala Tyr Met Glu Leu Ser Ser Leu Arg Ser
            100                 105                 110

Glu Asp Thr Ala Val Tyr Tyr Cys Ala Arg Ser Arg Leu Phe Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270
```

```
Thr Leu Met Ile Ser Arg Thr Pro Glu Val Thr Cys Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
                370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro Gly
465
```

<210> SEQ ID NO 92
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full length antibody hz2-8 (H1L2 G80A/T82A) HC
      nucleotide sequence

<400> SEQUENCE: 92

```
atggaccctg agggctctct gtcttggaga atcctgctgt tcctgagcct ggccttcgag    60
ctgtcttatg ccaggtgca gctggtgcag tctggcgccg aagtgaaaaa gcctggcgcc   120
tctgtgaagg tgtcctgcaa ggcctctggc ttcaacatca agaatatta catgcactgg   180 gtccgacagg cccctgagca aggattggaa tggatgggct ggatcgaccc cgagaacgcc   240
gatgccatct acgcccagaa attccagggc agagtgacca tcaccgccga cacctctacc   300
aacaccgcct acatggaact gtccagcctg agatctgagg acaccgccgt gtactactgc   360
gcccggtcca gactgttctt cgcctattgg ggccagggca ccctggtcac agtttcttcc   420
gcttccacca agggacccag cgtgttccct ctggctcctt ccagcaagtc tacctctggc   480
ggaacagctg ctctgggctg cctggtcaag gactactttc cagagcctgt gaccgtgtcc   540
tggaactctg gcgctctgac atctggcgtg cacacctttc cagctgtgct gcagtcctcc   600
ggcctgtact ctctgtcctc tgtcgtgacc gtgccttcca gctctctggg aacccagacc   660
tacatctgca atgtgaacca caagcctctcc aacaccaagg tggacaagaa ggtggaaccc   720
aagtcctgcg acaagaccca cacctgtcct ccatgtcctg ctccagaact gctcggcgga   780
```

```
ccttccgtgt tcctgtttcc tccaaagcct aaggacaccc tgatgatctc tcggacccct    840
gaagtgacct gcgtggtggt ggatgtgtct cacgaggacc cagaagtgaa gttcaattgg    900
tacgtggacg gcgtggaagt gcacaacgcc aagaccaagc ctagagagga cagtacaac     960 tccacctaca gagtggtgtc cgtgctgacc gtgctgcacc aggattggct gaacggcaaa    1020
gagtacaagt gcaaggtgtc caacaaggca ctgcccgctc ctatcgaaaa gaccatctcc    1080
aaggccaagg gccagcctag gaacccccag gtttacaccc tgcctccaag ccgggaagag    1140
atgaccaaga accaggtgtc cctgacctgc ctcgtgaagg gcttctaccc ttccgacatc    1200
gccgtggaat gggagagcaa tggccagcca gagaacaact acaagacaac ccctcctgtg    1260
ctggactccg acggctcatt cttcctgtac tccaagctga cagtggacaa gtccagatgg    1320
cagcagggca acgtgttctc ctgctccgtg atgcacgagg ccctgcacaa tcactacaca    1380
cagaagtccc tgtctctgtc ccctggctag                                     1410
```

<210> SEQ ID NO 93
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Full-length antibody hz2-8 (H1L2 G80A/T82A) LC protein sequence

<400> SEQUENCE: 93

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Lys Ser Leu Ser
            20                  25                  30

Ala Ser Val Gly Asp Arg Val Thr Ile Thr Cys Arg Ala Ser Gln Asp
        35                  40                  45

Val Arg Thr Ala Leu Asp Trp Tyr Gln Gln Lys Pro Gly Gln Ser Pro
    50                  55                  60

Lys Leu Leu Ile Tyr Ser Ala Ser Tyr Arg Tyr Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Gln Tyr
            100                 105                 110

Thr Thr Pro Tyr Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220
```

Val Thr Lys Ser Phe Asn Arg Gly Glu Cys
225                 230

<210> SEQ ID NO 94
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full-length antibody hz2-8 (H1L2 G80A/T82A) LC
      nucleotide sequence

<400> SEQUENCE: 94
atggaaaccg acacactgct gctgtgggtg ctgctcttgt gggtgccagg atctaccggc      60
gacatccaga tgacccagtc tccaaagtct ctgtccgcct ccgtgggcga cagagtgacc     120
atcacctgta gagcctctca ggacgtgcgg accgctctgg attggtatca gcagaagcct     180
ggccagtctc ctaagctgct gatctactcc gcctcctacc ggtactctgg cgtgccctcc     240
agattctccg gctctggctc tggcaccgac tttaccctga caatctccag cctgcagcct     300
gaggacttcg ccacctacta ctgccagcaa cagtacacca cccttacac cttcggccag      360
ggcaccaagc tggaaatcaa gagaaccgtg gccgctcctt ccgtgttcat cttcccacct     420
tccgacgagc agctgaagtc cggcacagct tctgtcgtgt gcctgctgaa caacttctac     480
cctcgggaag ccaaggtgca gtggaaggtg gacaatgccc tgcagtccgg caactcccaa     540
gagtctgtga ccgagcagga ctccaaggac agcacctaca gcctgtcctc cacactgaca     600
ctgtccaagg ccgactacga aagcacaag gtgtacgcct gcgaagtgac ccatcagggc      660
ctgtctagcc ctgtgaccaa gtctttcaac cggggcgagt gttag                     705

<210> SEQ ID NO 95
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Full length antibody hz2-8 (H1L2 G80A) HC
      protein sequence

<400> SEQUENCE: 95

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Phe Asn Ile Lys Glu Tyr Tyr Met His Trp Val Arg Gln Ala
    50                  55                  60

Pro Glu Gln Gly Leu Glu Trp Met Gly Trp Ile Asp Pro Glu Asn Ala
65                  70                  75                  80

Asp Thr Ile Tyr Ala Gln Lys Phe Gln Gly Arg Val Thr Ile Thr Ala
                85                  90                  95

Asp Thr Ser Thr Asn Thr Ala Tyr Met Glu Leu Ser Ser Leu Arg Ser
            100                 105                 110

Glu Asp Thr Ala Val Tyr Tyr Cys Ala Arg Ser Arg Leu Phe Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly
465

<210> SEQ ID NO 96
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Full length antibody hz2-8 (H1L2 G80A) HC
      nucleotide sequence

<400> SEQUENCE: 96

-continued

```
atggaccota agggctctct gtcttggaga atcctgctgt tcctgagcct ggccttcgag        60
ctgtcttatg gccaggtgca gctggtgcag tctggcgccg aagtgaaaaa gcctggcgcc       120
tctgtgaagg tgtcctgcaa ggcctctggc ttcaacatca agaatatta catgcactgg        180
gtccgacagg cccctgagca aggattggaa tggatgggct ggatcgaccc cgagaacgcc       240
gataccatct acgcccagaa attccagggc agagtgacca tcaccgccga cacctctacc       300
aacaccgcct acatggaact gtccagcctg agatctgagg acaccgccgt gtactactgc       360
gcccggtcca gactgttctt cgcctattgg ggccagggca ccctggtcac agtttcttcc       420
gcttccacca agggacccag cgtgttccct ctggctcctt ccagcaagtc tacctctggc       480
ggaacagctg ctctgggctg cctggtcaag gactactttc cagagcctgt gaccgtgtcc       540
tggaactctg gcgctctgac atctggcgtg cacacctttc cagctgtgct gcagtcctcc       600
ggcctgtact ctctgtcctc tgtcgtgacc gtgccttcca gctctctggg aacccagacc       660
tacatctgca atgtgaacca caagccttcc aacaccaagg tggacaagaa ggtggaaccc       720
aagtcctgcg acaagaccca cacctgtcct ccatgtcctg ctccagaact gctcggcgga       780
ccttccgtgt tcctgttcc tccaaagcct aaggacaccc tgatgatctc tcggaccct       840
gaagtgacct gcgtggtggt ggatgtgtct cacgaggacc cagaagtgaa gttcaattgg       900
tacgtggacg gcgtggaagt gcacaacgcc aagaccaagc ctagagagga acagtacaac       960
tccacctaca gagtggtgtc cgtgctgacc gtgctgcacc aggattggct gaacggcaaa      1020
gagtacaagt gcaaggtgtc caacaaggca ctgcccgctc ctatcgaaaa gaccatctcc      1080
aaggccaagg gccagcctag ggaaccccag gtttacaccc tgcctccaag ccgggaagag      1140
atgaccaaga accaggtgtc cctgacctgc ctcgtgaagg gcttctaccc ttccgacatc      1200
gccgtggaat gggagagcaa tggccagcca gagaacaact acaagacaac ccctcctgtg      1260
ctggactccg acggctcatt cttcctgtac tccaagctga cagtggacaa gtccagatgg      1320
cagcagggca acgtgttctc ctgctccgtg atgcacgagg ccctgcacaa tcactacaca      1380
cagaagtccc tgtctctgtc ccctggctag                                      1410
```

<210> SEQ ID NO 97
<211> LENGTH: 234
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Full-length antibody hz2-8 (H1L2 G80A) LC
    protein sequence

<400> SEQUENCE: 97

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Lys Ser Leu Ser
            20                  25                  30

Ala Ser Val Gly Asp Arg Val Thr Ile Thr Cys Arg Ala Ser Gln Asp
        35                  40                  45

Val Arg Thr Ala Leu Asp Trp Tyr Gln Gln Lys Pro Gly Gln Ser Pro
    50                  55                  60

Lys Leu Leu Ile Tyr Ser Ala Ser Tyr Arg Tyr Ser Gly Val Pro Ser
65                  70                  75                  80

Arg Phe Ser Gly Ser Gly Ser Gly Thr Asp Phe Thr Leu Thr Ile Ser
```

```
            85                  90                  95
Ser Leu Gln Pro Glu Asp Phe Ala Thr Tyr Tyr Cys Gln Gln Tyr
            100                 105                 110

Thr Thr Pro Tyr Thr Phe Gly Gln Gly Thr Lys Leu Glu Ile Lys Arg
        115                 120                 125

Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 98
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Full-length LC antibody hz2-8 (H1L2 G80A) nucleotide sequence

<400> SEQUENCE: 98

```
atggaaaccg acacactgct gctgtgggtg ctgctcttgt gggtgccagg atctaccggc    60
gacatccaga tgacccagtc tccaaagtct ctgtccgcct ccgtgggcga cagagtgacc   120
atcacctgta gagcctctca ggacgtgcgg accgctctgg attggtatca gcagaagcct   180
ggccagtctc ctaagctgct gatctactcc gcctcctacc ggtactctgg cgtgccctcc   240
agattctccg gctctggctc tggcaccgac tttaccctga caatctccag cctgcagcct   300
gaggacttcg ccacctacta ctgccagcaa cagtacacca ccttacacac cttcggccag   360
ggcaccaagc tggaaatcaa gagaaccgtg gccgctcctt ccgtgttcat cttcccacct   420
tccgacgagc agctgaagtc cggcacagct tctgtcgtgt gcctgctgaa caacttctac   480
cctcgggaag ccaaggtgca gtggaaggtg gacaatgccc tgcagtccgg caactcccaa   540
gagtctgtga ccgagcagga ctccaaggac agcacctaca gcctgtcctc cacactgaca   600
ctgtccaagg ccgactacga gaagcacaag gtgtacgcct gcgaagtgac ccatcagggc   660
ctgtctagcc ctgtgaccaa gtctttcaac cggggcgagt gttag                   705
```

<210> SEQ ID NO 99
<211> LENGTH: 673
<212> TYPE: PRT
<213> ORGANISM: Homo sapiens
<220> FEATURE:
<223> OTHER INFORMATION: Human C1s full-length wt protein sequence (huC1s)

<400> SEQUENCE: 99

Glu Pro Thr Met Tyr Gly Glu Ile Leu Ser Pro Asn Tyr Pro Gln Ala

-continued

```
1               5                   10                  15
Tyr Pro Ser Glu Val Glu Lys Ser Trp Asp Ile Glu Val Pro Glu Gly
            20                  25                  30
Tyr Gly Ile His Leu Tyr Phe Thr His Leu Asp Ile Glu Leu Ser Glu
            35                  40                  45
Asn Cys Ala Tyr Asp Ser Val Gln Ile Ile Ser Gly Asp Thr Glu Glu
 50                  55                  60
Gly Arg Leu Cys Gly Gln Arg Ser Ser Asn Pro His Ser Pro Ile
 65                  70                  75                  80
Val Glu Glu Phe Gln Val Pro Tyr Asn Lys Leu Gln Val Ile Phe Lys
                    85                  90                  95
Ser Asp Phe Ser Asn Glu Glu Arg Phe Thr Gly Phe Ala Ala Tyr Tyr
                    100                 105                 110
Val Ala Thr Asp Ile Asn Glu Cys Thr Asp Phe Val Asp Val Pro Cys
                    115                 120                 125
Ser His Phe Cys Asn Asn Phe Ile Gly Gly Tyr Phe Cys Ser Cys Pro
            130                 135                 140
Pro Glu Tyr Phe Leu His Asp Asp Met Lys Asn Cys Gly Val Asn Cys
145                 150                 155                 160
Ser Gly Asp Val Phe Thr Ala Leu Ile Gly Glu Ile Ala Ser Pro Asn
                    165                 170                 175
Tyr Pro Lys Pro Tyr Pro Glu Asn Ser Arg Cys Glu Tyr Gln Ile Arg
            180                 185                 190
Leu Glu Lys Gly Phe Gln Val Val Thr Leu Arg Arg Glu Asp Phe
            195                 200                 205
Asp Val Glu Ala Ala Asp Ser Ala Gly Asn Cys Leu Asp Ser Leu Val
            210                 215                 220
Phe Val Ala Gly Asp Arg Gln Phe Gly Pro Tyr Cys Gly His Gly Phe
225                 230                 235                 240
Pro Gly Pro Leu Asn Ile Glu Thr Lys Ser Asn Ala Leu Asp Ile Ile
                    245                 250                 255
Phe Gln Thr Asp Leu Thr Gly Gln Lys Lys Gly Trp Lys Leu Arg Tyr
            260                 265                 270
His Gly Asp Pro Met Pro Cys Pro Lys Glu Asp Thr Pro Asn Ser Val
            275                 280                 285
Trp Glu Pro Ala Lys Ala Lys Tyr Val Phe Arg Asp Val Val Gln Ile
            290                 295                 300
Thr Cys Leu Asp Gly Phe Glu Val Val Glu Gly Arg Val Gly Ala Thr
305                 310                 315                 320
Ser Phe Tyr Ser Thr Cys Gln Ser Asn Gly Lys Trp Ser Asn Ser Lys
                    325                 330                 335
Leu Lys Cys Gln Pro Val Asp Cys Gly Ile Pro Glu Ser Ile Glu Asn
                    340                 345                 350
Gly Lys Val Glu Asp Pro Glu Ser Thr Leu Phe Gly Ser Val Ile Arg
            355                 360                 365
Tyr Thr Cys Glu Glu Pro Tyr Tyr Met Glu Asn Gly Gly Gly
            370                 375                 380
Glu Tyr His Cys Ala Gly Asn Gly Ser Trp Val Asn Glu Val Leu Gly
385                 390                 395                 400
Pro Glu Leu Pro Lys Cys Val Pro Val Cys Gly Val Pro Arg Glu Pro
                    405                 410                 415
Phe Glu Glu Lys Gln Arg Ile Ile Gly Gly Ser Asp Ala Asp Ile Lys
            420                 425                 430
```

Asn Phe Pro Trp Gln Val Phe Asp Asn Pro Trp Ala Gly Gly Ala
    435                 440                 445

Leu Ile Asn Glu Tyr Trp Val Leu Thr Ala Ala His Val Val Glu Gly
    450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
                500                 505                 510

Asn Asp Ile Ala Leu Val Arg Leu Lys Asp Pro Val Lys Met Gly Pro
            515                 520                 525

Thr Val Ser Pro Ile Cys Leu Pro Gly Thr Ser Ser Asp Tyr Asn Leu
        530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
    610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp

<210> SEQ ID NO 100
<211> LENGTH: 2022
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant Human C1s nucleotide sequence
      (codon optimized)

<400> SEQUENCE: 100
gagcctacta tgtacggcga gatcctgtct cctaactacc tcaggcttac ccctccgag      60 gtggaaaagt cctgggatat cgaggtgccc gaaggctacg catccaccct gtacttcacc    120
cacctggaca tcgagctgtc cgagaactgc gcctacgact ccgtgcagat catctccggc    180
gataccgaag agggcagact gtgcggccag cggtcctcta caatcccca ctctcctatc    240 gtggaagagt tccaggtgcc atacaacaag ctgcaagtga tcttcaagtc cgacttctcc    300
aacgaggaac ggttcaccgg cttcgccgct tactatgtgg ccaccgacat caacgagtgc    360
accgacttcg tggacgtgcc ctgctctcac ttctgcaaca actttatcgg cggctacttc    420
tgcagctgcc ctcctgagta cttcctgcac gacgacatga gaactgcgg cgtgaactgc    480 tccggcgacg tgttcacagc tctgatcgga gagatcgcct ctccaaatta ccccaagcct    540

| | |
|---|---|
| tatcctgaga actcccgctg cgagtaccag atcagactgg aaaagggctt ccaggtggtg | 600 |
| gtcaccctgc ggcgcgagga ttttgatgtg gaagccgctg attccgccgg caactgcctg | 660 |
| gattctctgg tgtttgtggc cggcgacaga cagttcggcc cttattgtgg ccatggcttc | 720 |
| cccggacctc tgaacatcga dacaaagagc aacgccctgg atatcatctt ccagaccgac | 780 |
| ctgaccggcc agaagaaagg ctggaagctg agataccacg gcgacccat gccttgtcct | 840 |
| aaagaggaca cccctaactc cgtgtgggag cccgccaagg ccaaatacgt gttcagagat | 900 |
| gtggtccaga tcacctgtct ggacggcttt gaggtggtgg aaggcagagt gggcgccacc | 960 |
| tctttctact ctacctgcca gtccaacggc aagtggtcca actccaagct gaagtgccag | 1020 |
| cctgtggact gcggcatccc tgagtctatc gagaacggca aggtggaaga tcccgagagc | 1080 |
| accctgttcg gctccgtgat cagatatacc tgcgaggaac cctactacta catggaaaac | 1140 |
| ggcggaggcg gcgagtatca ctgtgctggc aatggctctt gggtcaacga ggtgctggga | 1200 |
| cccgaactgc ctaagtgtgt tcctgtgtgt ggcgtgccca gagagccctt cgaggaaaag | 1260 |
| cagagaatca tcggcggcag cgacgccgat atcaagaact cccctggca agtgttcttc | 1320 |
| gacaacccct gggctggcgg cgctctgatc aatgagtatt gggtgctgac cgccgctcac | 1380 |
| gtggtcgagg gaaatagaga acccactatg tatgtgggct ccaccagcgt gcagacctcc | 1440 |
| agactggcca agtccaagat gctgacccct gagcacgtgt tcatccatcc tggctggaaa | 1500 |
| ctgctggaag tgcccgaggg cagaacaaac ttcgataacg atatcgccct cgtgcggctg | 1560 |
| aaggaccctg tgaagatggg ccctaccgtg tctcctatct gtctgcctgg cacctcctcc | 1620 |
| gactacaacc tgatggatgg cgacctgggc ctgatctctg gatggggaag aaccgagaag | 1680 |
| cgggatagag ccgtcagact gaaggccgct agactgcctg ttgctcctct gcggaagtgc | 1740 |
| aaagaagtga aggtcgagaa gcctaccgcc gatgccgagg cctatgtgtt caccccaaac | 1800 |
| atgatctgcg ctggcggaga aaaggcatg gactcttgca agggcgattc cggcggagca | 1860 |
| ttcgcagtgc aggaccctaa cgacaagacc aagttctacg ctgccggcct ggtgtcttgg | 1920 |
| ggacctcagt gtggaaccta cggcctgtac accagagtga gaactacgt ggactggatc | 1980 |
| atgaagacca tgcaagagaa cagcaccct agagaggact ag | 2022 |

<210> SEQ ID NO 101
<211> LENGTH: 673
<212> TYPE: PRT
<213> ORGANISM: Mus musculus
<220> FEATURE:
<223> OTHER INFORMATION: Mouse C1s protein sequence (moC1s)

<400> SEQUENCE: 101

Glu Pro Thr Met His Gly Glu Ile Leu Ser Pro Asn Tyr Pro Gln Ala
1               5                   10                  15

Tyr Pro Asn Asp Val Val Lys Ser Trp Asp Ile Glu Val Pro Glu Gly
                20                  25                  30

Phe Gly Ile His Leu Tyr Phe Thr His Val Asp Ile Glu Pro Ser Glu
            35                  40                  45

Ser Cys Ala Tyr Asp Ser Val Gln Ile Ile Ser Gly Gly Ile Glu Glu
        50                  55                  60

Gly Arg Leu Cys Gly Gln Lys Thr Ser Lys Ser Pro Asn Ser Pro Ile
65                  70                  75                  80

Ile Glu Glu Phe Gln Phe Pro Tyr Asn Lys Leu Gln Val Val Phe Thr
                85                  90                  95

```
Ser Asp Phe Ser Asn Glu Glu Arg Phe Thr Gly Phe Ala Ala Tyr Tyr
            100                 105                 110

Thr Ala Ile Asp Ile Asn Glu Cys Thr Asp Phe Thr Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Arg Asn Cys Gly Val Asn Cys
145                 150                 155                 160

Ser Gly Asp Val Phe Thr Ala Leu Ile Gly Glu Ile Ser Ser Pro Asn
                165                 170                 175

Tyr Pro Asn Pro Tyr Pro Glu Asn Ser Arg Cys Glu Tyr Gln Ile Gln
            180                 185                 190

Leu Gln Glu Gly Phe Gln Val Val Thr Met Gln Arg Glu Asp Phe
        195                 200                 205

Asp Val Glu Pro Ala Asp Ser Glu Gly Asn Cys Pro Asp Ser Leu Thr
210                 215                 220

Phe Ala Ser Lys Asn Gln Gln Phe Gly Pro Tyr Cys Gly Asn Gly Phe
225                 230                 235                 240

Pro Gly Pro Leu Thr Ile Arg Thr Gln Ser Asn Thr Leu Gly Ile Val
                245                 250                 255

Phe Gln Thr Asp Leu Met Gly Gln Lys Lys Gly Trp Lys Leu Arg Tyr
            260                 265                 270

His Gly Asp Pro Ile Ser Cys Ala Lys Lys Ile Thr Ala Asn Ser Thr
            275                 280                 285

Trp Glu Pro Asp Lys Ala Lys Tyr Val Phe Lys Asp Val Val Lys Ile
290                 295                 300

Thr Cys Val Asp Gly Phe Glu Val Val Glu Gly His Val Ser Ser Thr
305                 310                 315                 320

Ser Tyr Tyr Ser Thr Cys Gln Ser Asp Gly Gln Trp Ser Asn Ser Gly
                325                 330                 335

Leu Lys Cys Gln Pro Val Tyr Cys Gly Ile Pro Asp Pro Ile Ala Asn
            340                 345                 350

Gly Lys Val Glu Glu Pro Glu Asn Ser Val Phe Gly Thr Val Val His
            355                 360                 365

Tyr Thr Cys Glu Glu Pro Tyr Tyr Met Glu His Glu Glu Gly Gly
    370                 375                 380

Glu Tyr Arg Cys Ala Ala Asn Gly Arg Trp Val Asn Asp Gln Leu Gly
385                 390                 395                 400

Ile Glu Leu Pro Arg Cys Ile Pro Ala Cys Gly Val Pro Thr Glu Pro
                405                 410                 415

Phe Gln Val His Gln Arg Ile Phe Gly Gly Gln Pro Ala Lys Ile Glu
            420                 425                 430

Asn Phe Pro Trp Gln Val Phe Phe Asn His Pro Arg Ala Ser Gly Ala
            435                 440                 445

Leu Ile Asn Glu Tyr Trp Val Leu Thr Ala Ala His Val Leu Glu Lys
    450                 455                 460

Ile Ser Asp Pro Leu Met Tyr Val Gly Thr Met Ser Val Arg Thr Thr
465                 470                 475                 480

Leu Leu Glu Asn Ala Gln Arg Leu Tyr Ser Lys Arg Val Phe Ile His
                485                 490                 495

Pro Ser Trp Lys Lys Glu Asp Asp Pro Asn Thr Arg Thr Asn Phe Asp
            500                 505                 510

Asn Asp Ile Ala Leu Val Gln Leu Lys Asp Pro Val Lys Met Gly Pro
```

```
                515                 520                 525
Lys Val Ser Pro Ile Cys Leu Pro Gly Thr Ser Ser Glu Tyr Asn Val
        530                 535                 540

Ser Pro Gly Asp Met Gly Leu Ile Ser Gly Trp Gly Ser Thr Glu Lys
545                 550                 555                 560

Lys Val Phe Val Ile Asn Leu Arg Gly Ala Lys Val Pro Val Thr Ser
                565                 570                 575

Leu Glu Thr Cys Lys Gln Val Lys Glu Glu Asn Pro Thr Val Arg Pro
            580                 585                 590

Glu Asp Tyr Val Phe Thr Asp Asn Met Ile Cys Ala Gly Glu Lys Gly
        595                 600                 605

Val Asp Ser Cys His Gly Asp Ser Gly Gly Ala Phe Ala Phe Gln Val
    610                 615                 620

Pro Asn Val Thr Val Pro Lys Phe Tyr Val Ala Gly Leu Val Ser Trp
625                 630                 635                 640

Gly Lys Arg Cys Gly Thr Tyr Gly Val Tyr Thr Lys Val Lys Asn Tyr
                645                 650                 655

Val Asp Trp Ile Leu Lys Thr Met Gln Glu Asn Ser Gly Pro Arg Lys
            660                 665                 670

Asp
```

<210> SEQ ID NO 102
<211> LENGTH: 2022
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant mouse C1s nucleotide sequence
      (codon optimized)

<400> SEQUENCE: 102

```
gagcctacaa tgcacggcga gatcctgtct ccaaactacc ctcaggctta ccccaacgac      60
gtggtcaagt cctgggatat cgaggtgcca gaaggcttcg gcatccacct gtacttcacc    120
cacgtggaca tcgagccttc cgagtcttgc gcctacgact ccgtgcagat catctccggc    180
ggaatcgaag agggcagact gtgcggccag aaaacctcca gtctcccaa ctctcccatt     240
atcgaggaat tcagttccc ctacaacaag ctgcaggtcg tgttcacctc cgacttctcc     300
aacgaggaac ggttcaccgg cttcgccgct tactacaccg ccatcgacat caacgagtgc    360
accgacttca ccgatgtgcc ctgcagccac ttctgcaaca ctttatcgg cggctacttc     420
tgcagctgcc ctcctgagta cttcctgcac gacgacatga aaactgcgg cgtgaactgc    480
tccggcacg tgttcacagc tctgatcgga gagatctcct ctcctaatta ccccaatcct    540
tatcctgaga actcccgctg cgagtaccag atccagctgc aagagggctt ccaggtggtg    600
gtcaccatgc agcgcgagga cttcgatgtg aacctgccg attctgaggg caactgccct    660
gactctctga ccttcgcctc caagaaccag cagttcggcc ttactgtgg caacggcttt    720
cctggacctc tgaccatcag aacccagagc aacaccctgg gcatcgtgtt ccagaccgat    780
ctgatgggcc agaagaaagg ctggaagctg agataccacg cgacccat cagctgcgcc     840
aagaagatca ccgccaactc cacctgggag cctgacaagg ccaaatacgt gttcaaggac    900
gtcgtgaaga tccatgcgt ggacggcttt gaggtggtgg aaggccacgt gtccagcacc     960
agctactact ctacctgcca gtctgacggc cagtggtcca actctggcct gaagtgtcag   1020
```

```
cctgtgtact gcggcatccc cgatcctatc gccaatggca aggtggaaga acccgagaac    1080
tccgtgtttg gcaccgtggt gcactatacc tgcgaggaac cctactacta catggaacat    1140
gaggaaggcg gcgagtaccg ctgtgccgct aatggaagat gggtcaacga ccagctgggc    1200
attgagctgc ccagatgcat tcctgcttgt ggcgtgccaa ccgagccttt ccaggtgcac    1260
cagagaatct ttggcggcca gcctgccaag atcgagaact cccttggca agtgttcttc    1320 aatcacccca gagcctctgg cgccctgatc aatgagtact gggtgctgac cgctgctcac    1380
gtgctggaaa agatcagcga ccctcttatg tacgtgggca ccatgtccgt gcggaccaca    1440
ctgttggaga acgcccagcg gctgtactcc aagagagtgt tcatccatcc tagctggaag    1500
aaagaggacg accccaacac caggaccaac ttcgacaacg atatcgccct ggtgcagctg    1560
aaggaccccg tgaagatggg ccctaaggtg tcccctatct gtctgcccgg cacctcctct    1620
gagtacaatg tgtctcctgg cgacatgggc ctgatctctg gctggggctc taccgagaag    1680
aaagtgttcg tgatcaacct gagaggcgcc aaggtgcccg tgacctctct ggaaacatgc    1740
aagcaagtga aagaagagaa ccccaccgtc cggcctgagg actatgtgtt caccgacaac    1800
atgatctgtg ccggcgagaa aggcgtggac tcttgccacg gcgattctgg cggagccttc    1860
gcctttcaag tgcccaatgt gaccgtgcct aagttctacg tggccggcct ggtgtcttgg    1920
ggcaagagat gtggtactta cggcgtgtac accaaagtga gaactacgt ggactggatt    1980 ctcaagacca tgcaagagaa cagcggcccc cggaaggact ag                       2022
```

<210> SEQ ID NO 103
<211> LENGTH: 673
<212> TYPE: PRT
<213> ORGANISM: Macaca fascicularis
<220> FEATURE:
<223> OTHER INFORMATION: Cynomolgus monkey C1s protein sequence (cyC1s)

<400> SEQUENCE: 103

```
Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Met Ser Gly Asp Ile Glu Glu
    50                  55                  60

Gly Arg Leu Cys Gly Gln Arg Thr Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Ala Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190
```

```
Leu Glu Lys Gly Phe Gln Val Val Thr Val Arg Arg Glu Asp Phe
            195                 200                 205

Asp Val Glu Pro Ala Asp Ser Glu Gly Asn Cys Leu Asp Ser Leu Val
    210                 215                 220

Phe Val Ala Gly Asp Gln Gln Phe Gly Pro Tyr Cys Gly Arg Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Asn Lys Gly Trp Lys Leu Arg Tyr
                260                 265                 270

His Gly Asp Pro Met Pro Cys Pro Lys Glu Thr Pro Thr Ser Val
            275                 280                 285

Trp Glu Pro Ala Lys Ala Lys Tyr Val Phe Arg Asp Val Val Arg Ile
            290                 295                 300

Thr Cys Leu Asp Gly Phe Glu Val Val Glu Gly Arg Val Gly Ala Thr
305                 310                 315                 320

Ser Phe His Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Thr Arg
            355                 360                 365

Tyr Thr Cys Glu Glu Pro Tyr Tyr Tyr Met Glu Asn Gly Gly Asn Gly
            370                 375                 380

Gln Tyr His Cys Ala Ser Asn Gly Ser Trp Val Asn Glu Ala Leu Ser
385                 390                 395                 400

Pro Glu Leu Pro Lys Cys Val Pro Val Cys Gly Val Pro Arg Glu Pro
                405                 410                 415

Phe Glu Gly Lys Gln Arg Ile Ile Gly Gly Ser Asp Ala Asp Ile Lys
                420                 425                 430

Asn Phe Pro Trp Gln Val Phe Phe Asp Asn Pro Trp Ala Gly Gly Ala
            435                 440                 445

Leu Ile Asp Glu Tyr Trp Val Leu Thr Ala Ala His Val Val Glu Gly
            450                 455                 460

Asn Gln Glu Pro Thr Met Tyr Val Gly Ser Thr Ser Val Gln Thr Ser
465                 470                 475                 480

Arg Leu Ala Lys Ser Lys Met Leu Thr Ser Glu Arg Val Phe Ile His
                485                 490                 495

Pro Gly Trp Lys Leu Leu Glu Val Pro Glu Ala Arg Thr Asn Phe Asp
                500                 505                 510

Asn Asp Ile Ala Leu Val Gln Leu Lys Asp Pro Val Lys Met Gly Pro
            515                 520                 525

Thr Val Ala Pro Ile Cys Leu Pro Gly Thr Ser Ser Asp Tyr Asn Leu
            530                 535                 540

Met Asp Gly Asp Leu Gly Leu Ile Ala Gly Trp Gly Arg Thr Glu Lys
545                 550                 555                 560

Arg Asp Arg Ala Leu Arg Leu Lys Ala Ala Arg Leu Pro Val Ala Pro
                565                 570                 575

Leu Arg Lys Cys Arg Glu Val Lys Val Glu Asn Pro Lys Ala Asp Ala
            580                 585                 590

Gly Ala Tyr Val Phe Thr Pro Asn Met Ile Cys Ala Gly Gly Glu Lys
            595                 600                 605
```

```
Gly Met Asp Ser Cys Lys Gly Asp Ser Gly Gly Ala Phe Ala Val Gln
    610                 615                 620

Asp Pro Asn Asp Lys Ala Lys Phe Tyr Val Ala Gly Leu Val Ser Trp
625                 630                 635                 640

Gly Pro Gln Cys Gly Thr Tyr Gly Leu Tyr Thr Arg Val Gln Asn Tyr
                645                 650                 655

Val Asp Trp Ile Lys Lys Thr Met Gln Glu Asn Ser Thr Pro Ser Lys
                660                 665                 670

Asp

<210> SEQ ID NO 104
<211> LENGTH: 2022
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant cynomolgus monkey C1s nucleotide
      sequence (codon optimized)

<400> SEQUENCE: 104
gagcctacta tgtacggcga gatcctgtct cctaactacc ctcaggctta ccctccgag        60 gtggaaaagt cctgggatat cgaggtgccc gaaggctacg catccacct gtacttcacc      120 cacctggaca tcgagctgtc cgagaactgc gcctacgact ccgtgcagat catgtccggc      180
gatatcgaag agggcagact gtgcggccag cggacctcta caatcccca ctctcctatc      240 gtggaagagt tccaggtgcc atacaacaag ctgcaagtga tcttcaagtc cgacttctcc     300
aacgaggaac ggttcaccgg cttcgccgct tactatgtgg ccaccgacat caacgagtgc    360
accgactttg tggacgcccc ttgcagccac ttctgcaaca actttatcgg cggctacttc    420
tgcagctgcc ctcctgagta tttcctgcac gacgacatga agaactgcgg cgtgaactgc    480
tccggcacgt gttcacagc tctgatcgga gagatcgcct ctccaaatta ccccaagcct    540
tatcctgaga actcccgctg cgagtaccag atcagactgg agaagggctt ccaggtggtg    600
gtcacagtgc ggcgcgagga cttgatgtg aacctgctg actccgaggg caactgcctg    660
gactctctgg tgtttgtggc tggcgatcag cagttcggcc cttactgtgg cagaggcttt    720
cccggaccac tgaacatcga cacaaagagc aacgccctgg atatcatctt ccagaccgac    780
ctgaccggcc agaacaaagg ctggaagctg agataccacg cgaccccat gccttgtcct    840 aaagaagaga caccccacctc cgtgtgggag cccgccaagg ctaaatacgt gttcagagat    900
gtcgtgcgga tcacctgtct ggacggcttt gaggtggtgg aaggcagagt gggcgccacc    960
tctttccact ctacctgcca gtctaacggc aagtggtcca actccaagct gaagtgccag   1020
cctgtggact gcggcatccc tgagtctatc gagaacggca aggtggaaga tccggagagc    1080
accctgtttg cagcgtgac cagatatacc tgcgaggaac cctactacta catggaaaac    1140
ggcggcaacg ccagtacca ctgtgcctct aatggctcct gggtcaacga ggccctgtct    1200
ccagaactgc ctaagtgcgt gccagtgtgt ggcgtgccaa gagagccttt tgagggcaag    1260
cagagaatca tcggcggcag cgacgccgat atcaagaact ccccctggca agtgttcttc    1320
gacaacccct gggctggcgg agccctgatc gatgaatatt gggtgctgac cgccgctcac    1380
gtggtcgagg gaaatcaaga acccactatg tatgtgggct ccaccagcgt gcagacctcc    1440
agactggcca agtccaagat gctgaccagc gagcgggtgt catccatcc tggctggaaa    1500 ctgctggagg tcccagaggc caggaccaac ttcgacaatg atatcgccct ggtgcagctg    1560
```

```
aaggacccccg tgaagatggg acctaccgtg gctcctatct gtctgcctgg caccctcctcc    1620 gactacaacc tgatggatgg cgacctgggc ctgatcgctg gatggggaag aaccgagaag    1680
agagacagag ccctgagact gaaggccgcc agattgcctg ttgctcctct gcggaagtgc    1740
cgggaagtga aggtcgagaa ccctaaggct gatgccggcg cttatgtgtt cacccctaat    1800
atgatctgcg ctggcggcga gaaaggcatg gactcttgca aaggcgattc tggcggcgca    1860
ttcgcagtgc aggaccctaa cgataaggcc aagttctacg tggccggcct ggtgtcttgg    1920
ggacctcagt gtggaacata cggcctgtac acacgggtgc agaactacgt ggactggatc    1980
aagaaaacca tgcaagagaa cagcaccccct tccaaggact ag                        2022
```

<210> SEQ ID NO 105
<211> LENGTH: 673
<212> TYPE: PRT
<213> ORGANISM: Rattus norvegicus
<220> FEATURE:
<223> OTHER INFORMATION: Rat C1s protein sequence (raC1s)

<400> SEQUENCE: 105

```
Glu Pro Thr Met Tyr Gly Glu Ile Leu Ser Pro Asn Tyr Pro Gln Ala
1               5                   10                  15

Tyr Pro Asn Glu Val Val Lys Thr Trp Asp Ile Glu Val Pro Glu Gly
                20                  25                  30

Phe Gly Ile His Leu Tyr Phe Thr His Leu Asp Met Glu Leu Ser Glu
            35                  40                  45

Asn Cys Ala Tyr Asp Ser Val Gln Ile Ile Ser Gly Gly Ile Glu Glu
        50                  55                  60

Glu Arg Leu Cys Gly Gln Arg Thr Ser Lys Ser Pro Asn Ser Pro Thr
65                  70                  75                  80

Val Glu Glu Phe Gln Phe Pro Tyr Asn Arg Leu Gln Val Val Phe Thr
                85                  90                  95

Ser Asp Phe Ser Asn Glu Glu Arg Phe Thr Gly Phe Ala Ala Tyr Tyr
            100                 105                 110

Ser Ala Val Asp Val Asn Glu Cys Thr Asp Phe Thr Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Arg Thr Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Asn Pro Tyr Pro Glu Asn Ser Arg Cys Glu Tyr Gln Ile Arg
            180                 185                 190

Leu Gln Glu Gly Phe Arg Leu Val Leu Thr Ile Arg Arg Glu Asp Phe
        195                 200                 205

Asp Val Glu Pro Ala Asp Ser Glu Gly Asn Cys His Asp Ser Leu Thr
    210                 215                 220

Phe Ala Ala Lys Asn Gln Gln Phe Gly Pro Tyr Cys Gly Asn Gly Phe
225                 230                 235                 240

Pro Gly Pro Leu Thr Ile Lys Thr Gln Ser Asn Thr Leu Asp Ile Val
                245                 250                 255

Phe Gln Thr Asp Leu Thr Gly Gln Asn Lys Gly Trp Lys Leu Arg Tyr
            260                 265                 270

His Gly Asp Pro Ile Pro Cys Pro Lys Glu Ile Ser Ala Asn Ser Ile
```

```
                275                 280                 285
Trp Glu Pro Glu Lys Ala Lys Tyr Val Phe Lys Asp Val Val Lys Ile
            290                 295                 300
Thr Cys Val Asp Gly Phe Glu Val Val Glu Gly Asn Val Gly Ser Thr
305                 310                 315                 320
Ser Phe Tyr Ser Thr Cys Gln Ser Asn Gly Gln Trp Ser Asn Ser Arg
                325                 330                 335
Leu Glu Cys Gln Pro Val Asp Cys Gly Val Pro Glu Pro Ile Glu Asn
            340                 345                 350
Gly Lys Val Glu Asp Pro Glu Asp Thr Val Phe Gly Ser Val Ile His
                355                 360                 365
Tyr Thr Cys Glu Glu Pro Tyr Tyr Met Glu Gln Glu Glu Gly Gly
    370                 375                 380
Glu Tyr His Cys Ala Ala Asn Gly Ser Trp Val Asn Asp Gln Leu Gly
385                 390                 395                 400
Val Glu Leu Pro Lys Cys Ile Pro Val Cys Gly Val Pro Thr Glu Pro
                405                 410                 415
Phe Lys Val Gln Gln Arg Ile Phe Gly Gly Tyr Ser Thr Lys Ile Gln
            420                 425                 430
Ser Phe Pro Trp Gln Val Tyr Phe Glu Ser Pro Arg Gly Gly Gly Ala
                435                 440                 445
Leu Ile Asp Glu Tyr Trp Val Leu Thr Ala Ala His Val Val Glu Gly
            450                 455                 460
Asn Ser Asp Pro Val Met Tyr Val Gly Ser Thr Leu Leu Lys Ile Glu
465                 470                 475                 480
Arg Leu Arg Asn Ala Gln Arg Leu Ile Thr Glu Arg Val Ile Ile His
                485                 490                 495
Pro Ser Trp Lys Gln Glu Asp Asp Leu Asn Thr Arg Thr Asn Phe Asp
            500                 505                 510
Asn Asp Ile Ala Leu Val Gln Leu Lys Asp Pro Val Lys Met Gly Pro
            515                 520                 525
Thr Val Ala Pro Ile Cys Leu Pro Glu Thr Ser Ser Asp Tyr Asn Pro
    530                 535                 540
Ser Glu Gly Asp Leu Gly Leu Ile Ser Gly Trp Gly Arg Thr Glu Asn
545                 550                 555                 560
Arg Thr Asn Val Ile Gln Leu Arg Gly Ala Lys Leu Pro Ile Thr Ser
                565                 570                 575
Leu Glu Lys Cys Gln Gln Val Lys Val Glu Asn Pro Lys Ala Arg Ser
            580                 585                 590
Asn Asp Tyr Val Phe Thr Asp Asn Met Ile Cys Ala Gly Glu Lys Gly
                595                 600                 605
Val Asp Ser Cys Glu Gly Asp Ser Gly Gly Ala Phe Ala Leu Pro Val
            610                 615                 620
Pro Asn Val Lys Asp Pro Lys Phe Tyr Val Ala Gly Leu Val Ser Trp
625                 630                 635                 640
Gly Lys Lys Cys Gly Thr Tyr Gly Ile Tyr Thr Lys Val Lys Asn Tyr
                645                 650                 655
Val Asp Trp Ile Leu Lys Thr Met Gln Glu Asn Ser Gly Pro Lys Lys
            660                 665                 670
Asp

<210> SEQ ID NO 106
<211> LENGTH: 2022
```

<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant rat C1s nucleotide sequence

<400> SEQUENCE: 106

| | | | | | |
|---|---|---|---|---|---|
| gagcctacca | tgtatgggga | gatcctgtcc | cctaattatc | cccaggcgta | ccccaatgag | 60 |
| gtcgtgaaaa | cttgggacat | agaagtccca | gaggggtttg | ggattcacct | ttacttcacc | 120 |
| catctggaca | tggagctgtc | agagaactgt | gcgtacgact | cagtgcagat | aatctcagga | 180 |
| ggcatcgagg | aagagagact | ctgtggccag | aggaccagca | agagtcccaa | ctcccccact | 240 |
| gtagaagagt | ttcaattccc | atacaatagg | ctccaggtgg | tctttacgtc | agacttctcc | 300 |
| aacgaggaac | ggtttactgg | ctttgcagcg | tattactcag | ccgtagatgt | aaatgaatgc | 360 |
| acagacttta | cagatgtccc | ttgcagccac | ttctgcaata | acttcattgg | tggatacttc | 420 |
| tgctcctgcc | ccccagaata | cttcctccac | gatgacatga | ggacttgtgg | ggtcaactgt | 480 |
| agtggggatg | tattcactgc | cctgattggg | gagatcgcaa | gtcccaatta | tcccaaccca | 540 |
| tacccggaga | actcaaggtg | tgaataccag | attcggctgc | aggagggctt | ccgactggtg | 600 |
| ttgactatcc | ggagagaaga | ttttgatgtg | gaaccagctg | actcagaggg | gaactgccac | 660 |
| gacagtttga | cttttgctgc | aaaaaaccaa | cagtttggtc | cttactgtgg | caatggattc | 720 |
| cctggaccct | caactattaa | aacccagagc | aatactcttg | atattgtctt | tcaaactgac | 780 |
| ctaacggggc | aaaataaagg | ctggaagctt | cgttaccatg | gagatcccat | cccctgtccc | 840 |
| aaagaaatca | gtgctaattc | tatctgggag | cccgaaaagg | caaaatacgt | gttcaaagat | 900 |
| gtcgtgaaga | taacctgtgt | ggatggattc | gaagttgtgg | agggaaatgt | tggctcaaca | 960 |
| tcattctatt | ccacttgtca | agcaacgga | cagtggagca | attccaggct | agagtgtcaa | 1020 |
| cctgtggact | gtggtgttcc | agaacccatt | gagaatggta | agttgaaga | cccagaagac | 1080 |
| actgtattcg | gctccgtcat | ccactacacg | tgcgaagagc | atattacta | catggaacag | 1140 |
| gaagaaggcg | gagagtatca | ctgtgctgct | aatgggagct | gggtgaatga | ccagctgggt | 1200 |
| gtcgagcttc | caaaatgtat | tccagtctgt | ggagtaccca | ccgagccctt | taaagtacag | 1260 |
| cagaggatat | ttggaggata | ctctacaaag | attcaaagtt | ttccttggca | ggtctacttt | 1320 |
| gagtcccccc | gaggtggcgg | ggctcttatc | gatgagtact | gggtgctgac | ggccgctcac | 1380 |
| gttgtggagg | gaaactctga | cccagtgatg | tatgtcgggt | ccacacttct | gaaaatagag | 1440 |
| cggttgagaa | atgcccagag | gctcatcact | gaacgtgtga | ttattcatcc | cagctggaaa | 1500 |
| caagaggacg | acctgaatac | acggacaaat | tttgacaatg | acattgccct | ggtgcagctc | 1560 |
| aaagaccctg | tgaaaatggg | acccactgtt | gcccccatct | gcctgccaga | aacctcctca | 1620 |
| gactacaacc | cctcagaggg | tgacctgggg | ctgatctctg | gtggggccg | aacagagaat | 1680 |
| agaaccaatg | ttattcaact | cagaggggcg | aagttaccca | taacatcttt | agaaaagtgc | 1740 |
| cagcaggtga | aagtggaaaa | cccgaaagcg | aggtcaaacg | actatgtttt | cactgacaac | 1800 |
| atgatctgtg | ctggggaaaa | gggtgtggac | agctgtgaag | gtgacagcgg | aggggctttt | 1860 |
| gctctgccgg | tccccaatgt | caaggacccc | aaattctatg | tggctggcct | ggtgtcctgg | 1920 |
| gggaaaagt | gtgggaccta | tgggatctac | acaaaggtaa | agaactacgt | ggactggatc | 1980 |
| ctgaaaacta | tgcaggagaa | tagtgggccc | aagaaggact | ag | | 2022 |

<210> SEQ ID NO 107
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human C1s deletion mutant 1 (huC1sM151)
      protein sequence

<400> SEQUENCE: 107

Tyr His Gly Asp Pro Lys Glu Asp Thr Pro Asn Ser Val Trp Glu Pro
1               5                   10                  15

Ala Lys Ala Lys Tyr Val Phe Arg Asp Val Val Gln Ile Thr Cys Leu
            20                  25                  30

Asp Gly Phe Glu Val Val Glu Gly Arg Val Gly Ala Thr Ser Phe Tyr
        35                  40                  45

Ser Thr Cys Gln Ser Asn Gly Lys Trp Ser Asn Ser Lys Leu Lys Cys
    50                  55                  60

Gln Pro Val Asp Cys Gly Ile Pro Glu Ser Ile Glu Asn Gly Lys Val
65                  70                  75                  80

Glu Asp Pro Glu Ser Thr Leu Phe Gly Ser Val Ile Arg Tyr Thr Cys
                85                  90                  95

Glu Glu Pro Tyr Tyr Tyr Met Glu Asn Gly Gly Gly Glu Tyr His
            100                 105                 110

Cys Ala Gly Asn Gly Ser Trp Val Asn Glu Val Leu Gly Pro Glu Leu
        115                 120                 125

Pro Lys Cys Val Pro Val Cys Gly Val Pro Arg Glu Pro Phe Glu Glu
    130                 135                 140

Lys Gln Arg
145

<210> SEQ ID NO 108
<211> LENGTH: 456
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant Human C1s deletion mutant 1
      (huC1sM151) nucleotide sequence

<400> SEQUENCE: 108
taccacggcg accccatgcc ttgtcctaaa gaggacaccc ctaactccgt gtgggagccc      60
gccaaggcca aatacgtgtt cagagatgtg gtccagatca cctgtctgga cggctttgag     120
gtggtggaag gcagagtggg cgccacctct ttctactcta cctgccagtc caacggcaag     180
tggtccaact ccaagctgaa gtgccagcct gtggactgcg gcatccctga gtctatcgag     240
aacggcaagg tggaagatcc cgagagcacc ctgttcggct ccgtgatcag atatacctgc     300
gaggaaccct actactacat ggaaaacggc ggaggcggcg agtatcactg tgctggcaat     360
ggctcttggg tcaacgaggt gctgggaccc gaactgccta gtgtgttcc tgtgtgtggc     420 gtgcccagag agcccttcga ggaaaagcag agatag                              456

<210> SEQ ID NO 109
<211> LENGTH: 428
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: Human C1s deletion mutant 2 (huC1sNHC) protein
sequence

<400> SEQUENCE: 109

```
Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe
            195                 200                 205

Asp Val Glu Ala Ala Asp Ser Ala Gly Asn Cys Leu Asp Ser Leu Val
210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
        275                 280                 285

Trp Glu Pro Ala Lys Ala Lys Tyr Val Phe Arg Asp Val Val Gln Ile
    290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
        355                 360                 365

Tyr Thr Cys Glu Glu Pro Tyr Tyr Met Glu Asn Gly Gly Gly Gly
    370                 375                 380
```

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg His His His His His His
                420                 425

<210> SEQ ID NO 110
<211> LENGTH: 1269
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinant Human C1s deletion mutant 2
      (huC1sNHC) nucleotide sequence

<400> SEQUENCE: 110
gagcctacta tgtacggcga gatcctgtct cctaactacc tcaggcttca ccctccgag       60 gtggaaaagt cctgggatat cgaggtgccc gaaggctacg catccacct gtacttcacc      120 cacctggaca tcgagctgtc cgagaactgc gcctacgact ccgtgcagat catctccggc     180
gataccgaag agggcagact gtgcggccag cggtcctcta acaatcccca ctctcctatc     240
gtggaagagt tccaggtgcc atacaacaag ctgcaagtga tcttcaagtc cgacttctcc     300
aacgaggaac ggttcaccgg cttcgccgct tactatgtgg ccaccgacat caacgagtgc     360
accgacttcg tggacgtgcc ctgctctcac ttctgcaaca actttatcgg cggctacttc     420
tgcagctgcc ctcctgagta cttcctgcac gacgacatga gaactgcgg cgtgaactgc     480 tccggcgacg tgttcacagc tctgatcgga gagatcgcct ctccaaatta ccccaagcct    540
tatcctgaga actcccgctg cgagtaccag atcagactgg aaaagggctt ccaggtggtg    600
gtcaccctgc ggcgcgagga ttttgatgtg gaagccgctg attccgccgg caactgcctg    660
gattctctgg tgtttgtggc cggcgacaga cagttcggcc cttattgtgg ccatggcttc    720
cccggacctc tgaacatcga cacaaagagc aacgccctgg atatcatctt ccagaccgac    780
ctgaccggcc agaagaaagg ctggaagctg agataccacg gcgacccct gccttgtcct    840 aaagaggaca cccctaactc cgtgtgggag cccgccaagg ccaaatacgt gttcagagat    900
gtggtccaga tcacctgtct ggacggcttt gaggtggtgg aaggcagagt gggcgccacc    960
tcttctctac ctacctgcca gtccaacggc aagtggtcca actccaagct gaagtgccag   1020
cctgtggact gcggcatccc tgagtctatc gagaacggca aggtggaaga tcccgagagc   1080
accctgttcg gctccgtgat cagatatacc tgcgaggaac cctactacta catggaaaac   1140
ggcggaggcg gcgagtatca ctgtgctggc aatggctctt gggtcaacga ggtgctggga   1200
cccgaactgc ctaagtgtgt tcctgtgtgt ggcgtgccca gagagccctt cgaggaaaag   1260
cagagatag                                                           1269

<210> SEQ ID NO 111
<211> LENGTH: 389
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human C1s deletion mutant 3 (NHCD33) protein
      sequence

<400> SEQUENCE: 111

```
Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
50                  55                  60

Gly Arg Leu Cys Gly Gln Arg Ser Ser Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe
        195                 200                 205

Asp Val Glu Ala Ala Asp Ser Ala Gly Asn Cys Leu Asp Ser Leu Val
    210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
        275                 280                 285

Trp Glu Pro Ala Lys Ala Lys Tyr Val Phe Arg Asp Val Val Gln Ile
290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
        355                 360                 365

Tyr Thr Cys Glu Glu Pro Tyr Tyr Met Glu Asn Gly Gly Gly Gly
    370                 375                 380

Glu Tyr His Cys Ala
385
```

<210> SEQ ID NO 112
<211> LENGTH: 673
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Protein sequence of Human C1s M1(M277I)-His

<400> SEQUENCE: 112

```
Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Val Thr Leu Arg Arg Glu Asp Phe
        195                 200                 205

Asp Val Glu Ala Ala Asp Ser Ala Gly Asn Cys Leu Asp Ser Leu Val
    210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Ile Pro Cys Pro Lys Glu Asp Thr Pro Asn Ser Val
        275                 280                 285

Trp Glu Pro Ala Lys Ala Lys Tyr Val Phe Arg Asp Val Val Gln Ile
    290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
```

```
            355                 360                 365
Tyr Thr Cys Glu Glu Pro Tyr Tyr Met Glu Asn Gly Gly Gly
    370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
                420                 425                 430

Asn Phe Pro Trp Gln Val Phe Phe Asp Asn Pro Trp Ala Gly Gly Ala
            435                 440                 445

Leu Ile Asn Glu Tyr Trp Val Leu Thr Ala Ala His Val Val Glu Gly
        450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
                500                 505                 510

Asn Asp Ile Ala Leu Val Arg Leu Lys Asp Pro Val Lys Met Gly Pro
            515                 520                 525

Thr Val Ser Pro Ile Cys Leu Pro Gly Thr Ser Ser Asp Tyr Asn Leu
        530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
                580                 585                 590

Glu Ala Tyr Val Phe Thr Pro Asn Met Ile Cys Ala Gly Gly Glu Lys
            595                 600                 605

Gly Met Asp Ser Cys Lys Gly Asp Ser Gly Gly Ala Phe Ala Val Gln
        610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
                660                 665                 670

Asp
```

<210> SEQ ID NO 113
<211> LENGTH: 673
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Protein sequence of human C1s M2 (M277I,
    K331Q)-His

<400> SEQUENCE: 113

```
Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
```

-continued

```
                20                  25                  30
Tyr Gly Ile His Leu Tyr Phe Thr His Leu Asp Ile Glu Leu Ser Glu
                35                  40                  45
Asn Cys Ala Tyr Asp Ser Val Gln Ile Ile Ser Gly Asp Thr Glu Glu
 50                  55                  60
Gly Arg Leu Cys Gly Gln Arg Ser Ser Asn Asn Pro His Ser Pro Ile
 65                  70                  75                  80
Val Glu Glu Phe Gln Val Pro Tyr Asn Lys Leu Gln Val Ile Phe Lys
                 85                  90                  95
Ser Asp Phe Ser Asn Glu Glu Arg Phe Thr Gly Phe Ala Ala Tyr Tyr
                100                 105                 110
Val Ala Thr Asp Ile Asn Glu Cys Thr Asp Phe Val Asp Val Pro Cys
                115                 120                 125
Ser His Phe Cys Asn Asn Phe Ile Gly Gly Tyr Phe Cys Ser Cys Pro
                130                 135                 140
Pro Glu Tyr Phe Leu His Asp Asp Met Lys Asn Cys Gly Val Asn Cys
145                 150                 155                 160
Ser Gly Asp Val Phe Thr Ala Leu Ile Gly Glu Ile Ala Ser Pro Asn
                165                 170                 175
Tyr Pro Lys Pro Tyr Pro Glu Asn Ser Arg Cys Glu Tyr Gln Ile Arg
                180                 185                 190
Leu Glu Lys Gly Phe Gln Val Val Val Thr Leu Arg Arg Glu Asp Phe
                195                 200                 205
Asp Val Glu Ala Ala Asp Ser Ala Gly Asn Cys Leu Asp Ser Leu Val
                210                 215                 220
Phe Val Ala Gly Asp Arg Gln Phe Gly Pro Tyr Cys Gly His Gly Phe
225                 230                 235                 240
Pro Gly Pro Leu Asn Ile Glu Thr Lys Ser Asn Ala Leu Asp Ile Ile
                245                 250                 255
Phe Gln Thr Asp Leu Thr Gly Gln Lys Lys Gly Trp Lys Leu Arg Tyr
                260                 265                 270
His Gly Asp Pro Ile Pro Cys Pro Lys Glu Asp Thr Pro Asn Ser Val
                275                 280                 285
Trp Glu Pro Ala Lys Ala Lys Tyr Val Phe Arg Asp Val Val Gln Ile
                290                 295                 300
Thr Cys Leu Asp Gly Phe Glu Val Val Glu Gly Arg Val Gly Ala Thr
305                 310                 315                 320
Ser Phe Tyr Ser Thr Cys Gln Ser Asn Gly Gln Trp Ser Asn Ser Lys
                325                 330                 335
Leu Lys Cys Gln Pro Val Asp Cys Gly Ile Pro Glu Ser Ile Glu Asn
                340                 345                 350
Gly Lys Val Glu Asp Pro Glu Ser Thr Leu Phe Gly Ser Val Ile Arg
                355                 360                 365
Tyr Thr Cys Glu Glu Pro Tyr Tyr Tyr Met Glu Asn Gly Gly Gly Gly
                370                 375                 380
Glu Tyr His Cys Ala Gly Asn Gly Ser Trp Val Asn Glu Val Leu Gly
385                 390                 395                 400
Pro Glu Leu Pro Lys Cys Val Pro Val Cys Gly Val Pro Arg Glu Pro
                405                 410                 415
Phe Glu Glu Lys Gln Arg Ile Ile Gly Gly Ser Asp Ala Asp Ile Lys
                420                 425                 430
Asn Phe Pro Trp Gln Val Phe Phe Asp Asn Pro Trp Ala Gly Gly Ala
                435                 440                 445
```

```
Leu Ile Asn Glu Tyr Trp Val Leu Thr Ala Ala His Val Val Glu Gly
    450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
        515                 520                 525

Thr Val Ser Pro Ile Cys Leu Pro Gly Thr Ser Ser Asp Tyr Asn Leu
    530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
    610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp

<210> SEQ ID NO 114
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein  sequence of human C1s M3 (M277I,
      P278, N329D)-His

<400> SEQUENCE: 114

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110
```

```
Val Ala Thr Asp Ile Asn Glu Cys Thr Asp Phe Val Asp Val Pro Cys
            115                 120                 125

Ser His Phe Cys Asn Asn Phe Ile Gly Gly Tyr Phe Cys Ser Cys Pro
        130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
                180                 185                 190

Leu Glu Lys Gly Phe Gln Val Val Thr Leu Arg Arg Glu Asp Phe
            195                 200                 205

Asp Val Glu Ala Ala Asp Ser Ala Gly Asn Cys Leu Asp Ser Leu Val
    210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Ile Ser Cys Pro Lys Glu Asp Thr Pro Asn Ser Val
        275                 280                 285

Trp Glu Pro Ala Lys Ala Lys Tyr Val Phe Arg Asp Val Val Gln Ile
    290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asp Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
        355                 360                 365

Tyr Thr Cys Glu Glu Pro Tyr Tyr Tyr Met Glu Asn Gly Gly Gly Gly
    370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
        435                 440                 445

Leu Ile Asn Glu Tyr Trp Val Leu Thr Ala Ala His Val Val Glu Gly
    450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
        515                 520                 525
```

-continued

```
Thr Val Ser Pro Ile Cys Leu Pro Gly Thr Ser Ser Asp Tyr Asn Leu
            530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
                580                 585                 590

Glu Ala Tyr Val Phe Thr Pro Asn Met Ile Cys Ala Gly Gly Glu Lys
                595                 600                 605

Gly Met Asp Ser Cys Lys Gly Asp Ser Gly Gly Ala Phe Ala Val Gln
        610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
                660                 665                 670

Asp

<210> SEQ ID NO 115
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M4 (P280A,
      E282K)-His

<400> SEQUENCE: 115

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
                20                  25                  30

Tyr Gly Ile His Leu Tyr Phe Thr His Leu Asp Ile Glu Leu Ser Glu
            35                  40                  45

Asn Cys Ala Tyr Asp Ser Val Gln Ile Ile Ser Gly Asp Thr Glu Glu
        50                  55                  60

Gly Arg Leu Cys Gly Gln Arg Ser Ser Asn Asn Pro His Ser Pro Ile
65              70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
                100                 105                 110

Val Ala Thr Asp Ile Asn Glu Cys Thr Asp Phe Val Asp Val Pro Cys
            115                 120                 125

Ser His Phe Cys Asn Asn Phe Ile Gly Gly Tyr Phe Cys Ser Cys Pro
        130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
                180                 185                 190
```

-continued

```
Leu Glu Lys Gly Phe Gln Val Val Thr Leu Arg Arg Glu Asp Phe
            195                 200                 205

Asp Val Glu Ala Ala Asp Ser Ala Gly Asn Cys Leu Asp Ser Leu Val
210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
                260                 265                 270

His Gly Asp Pro Met Pro Cys Ala Lys Lys Asp Thr Pro Asn Ser Val
            275                 280                 285

Trp Glu Pro Ala Lys Ala Lys Tyr Val Phe Arg Asp Val Gln Ile
290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
                340                 345                 350

Gly Lys Val Glu Asp Pro Glu Ser Thr Leu Phe Gly Ser Val Ile Arg
            355                 360                 365

Tyr Thr Cys Glu Glu Pro Tyr Tyr Met Glu Asn Gly Gly Gly Gly
            370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
                420                 425                 430

Asn Phe Pro Trp Gln Val Phe Phe Asp Asn Pro Trp Ala Gly Gly Ala
            435                 440                 445

Leu Ile Asn Glu Tyr Trp Val Leu Thr Ala Ala His Val Val Glu Gly
450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
            515                 520                 525

Thr Val Ser Pro Ile Cys Leu Pro Gly Thr Ser Ser Asp Tyr Asn Leu
530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Glu Lys Pro Thr Ala Asp Ala
            580                 585                 590

Glu Ala Tyr Val Phe Thr Pro Asn Met Ile Cys Ala Gly Gly Glu Lys
            595                 600                 605

Gly Met Asp Ser Cys Lys Gly Asp Ser Gly Gly Ala Phe Ala Val Gln
```

```
                610                 615                 620
Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp

<210> SEQ ID NO 116
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M5 (K336G)-His

<400> SEQUENCE: 116

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe Asp
        195                 200                 205

Asp Val Glu Ala Ala Asp Ser Ala Gly Asn Cys Leu Asp Ser Leu Val
    210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
        275                 280                 285
```

-continued

Trp Glu Pro Ala Lys Ala Lys Tyr Val Phe Arg Asp Val Val Gln Ile
    290             295             300

Thr Cys Leu Asp Gly Phe Glu Val Val Glu Gly Arg Val Gly Ala Thr
305             310             315             320

Ser Phe Tyr Ser Thr Cys Gln Ser Asn Gly Lys Trp Ser Asn Ser Gly
                325             330             335

Leu Lys Cys Gln Pro Val Asp Cys Gly Ile Pro Glu Ser Ile Glu Asn
            340             345             350

Gly Lys Val Glu Asp Pro Glu Ser Thr Leu Phe Gly Ser Val Ile Arg
        355             360             365

Tyr Thr Cys Glu Glu Pro Tyr Tyr Tyr Met Glu Asn Gly Gly Gly Gly
    370             375             380

Glu Tyr His Cys Ala Gly Asn Gly Ser Trp Val Asn Glu Val Leu Gly
385             390             395             400

Pro Glu Leu Pro Lys Cys Val Pro Val Cys Gly Val Pro Arg Glu Pro
                405             410             415

Phe Glu Glu Lys Gln Arg Ile Ile Gly Gly Ser Asp Ala Asp Ile Lys
            420             425             430

Asn Phe Pro Trp Gln Val Phe Phe Asp Asn Pro Trp Ala Gly Gly Ala
        435             440             445

Leu Ile Asn Glu Tyr Trp Val Leu Thr Ala Ala His Val Val Glu Gly
    450             455             460

Asn Arg Glu Pro Thr Met Tyr Val Gly Ser Thr Ser Val Gln Thr Ser
465             470             475             480

Arg Leu Ala Lys Ser Lys Met Leu Thr Pro Glu His Val Phe Ile His
                485             490             495

Pro Gly Trp Lys Leu Leu Glu Val Pro Glu Gly Arg Thr Asn Phe Asp
            500             505             510

Asn Asp Ile Ala Leu Val Arg Leu Lys Asp Pro Val Lys Met Gly Pro
        515             520             525

Thr Val Ser Pro Ile Cys Leu Pro Gly Thr Ser Ser Asp Tyr Asn Leu
    530             535             540

Met Asp Gly Asp Leu Gly Leu Ile Ser Gly Trp Gly Arg Thr Glu Lys
545             550             555             560

Arg Asp Arg Ala Val Arg Leu Lys Ala Ala Arg Leu Pro Val Ala Pro
                565             570             575

Leu Arg Lys Cys Lys Glu Val Lys Val Glu Lys Pro Thr Ala Asp Ala
            580             585             590

Glu Ala Tyr Val Phe Thr Pro Asn Met Ile Cys Ala Gly Gly Glu Lys
        595             600             605

Gly Met Asp Ser Cys Lys Gly Asp Ser Gly Gly Ala Phe Ala Val Gln
    610             615             620

Asp Pro Asn Asp Lys Thr Lys Phe Tyr Ala Ala Gly Leu Val Ser Trp
625             630             635             640

Gly Pro Gln Cys Gly Thr Tyr Gly Leu Tyr Thr Arg Val Lys Asn Tyr
                645             650             655

Val Asp Trp Ile Met Lys Thr Met Gln Glu Asn Ser Thr Pro Arg Glu
            660             665             670

Asp

<210> SEQ ID NO 117
<211> LENGTH: 673
<212> TYPE: PRT

-continued

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M6 (P280A,
      E282K, K336G)-His

<400> SEQUENCE: 117
```

| | | | | | | | | | | | | | | |
|---|---|---|---|---|---|---|---|---|---|---|---|---|---|---|
Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Val Thr Leu Arg Arg Glu Asp Phe
        195                 200                 205

Asp Val Glu Ala Ala Asp Ser Ala Gly Asn Cys Leu Asp Ser Leu Val
210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Ala Lys Lys Asp Thr Pro Asn Ser Val
        275                 280                 285

Trp Glu Pro Ala Lys Ala Lys Tyr Val Phe Arg Asp Val Val Gln Ile
290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Gly
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
        355                 360                 365

-continued

```
Tyr Thr Cys Glu Glu Pro Tyr Tyr Met Glu Asn Gly Gly Gly
    370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
                420                 425                 430

Asn Phe Pro Trp Gln Val Phe Phe Asp Asn Pro Trp Ala Gly Gly Ala
            435                 440                 445

Leu Ile Asn Glu Tyr Trp Val Leu Thr Ala Ala His Val Val Glu Gly
450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
                500                 505                 510

Asn Asp Ile Ala Leu Val Arg Leu Lys Asp Pro Val Lys Met Gly Pro
            515                 520                 525

Thr Val Ser Pro Ile Cys Leu Pro Gly Thr Ser Ser Asp Tyr Asn Leu
    530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
            595                 600                 605

Gly Met Asp Ser Cys Lys Gly Asp Ser Gly Gly Ala Phe Ala Val Gln
    610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
                660                 665                 670

Asp
```

<210> SEQ ID NO 118
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M7 (D343Y,
      E351A)-His

<400> SEQUENCE: 118

```
Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30
```

```
Tyr Gly Ile His Leu Tyr Phe Thr His Leu Asp Ile Glu Leu Ser Glu
             35                  40                  45

Asn Cys Ala Tyr Asp Ser Val Gln Ile Ile Ser Gly Asp Thr Glu Glu
 50                  55                  60

Gly Arg Leu Cys Gly Gln Arg Ser Ser Asn Asn Pro His Ser Pro Ile
 65                  70                  75                  80

Val Glu Glu Phe Gln Val Pro Tyr Asn Lys Leu Gln Val Ile Phe Lys
                 85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe
        195                 200                 205

Asp Val Glu Ala Ala Asp Ser Ala Gly Asn Cys Leu Asp Ser Leu Val
    210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
        275                 280                 285

Trp Glu Pro Ala Lys Ala Lys Tyr Val Phe Arg Asp Val Val Gln Ile
290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Tyr Cys Gly Ile Pro Glu Ser Ile Ala Asn
            340                 345                 350

Gly Lys Val Glu Asp Pro Glu Ser Thr Leu Phe Gly Ser Val Ile Arg
        355                 360                 365

Tyr Thr Cys Glu Glu Pro Tyr Tyr Met Glu Asn Gly Gly Gly Gly
    370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
        435                 440                 445

Leu Ile Asn Glu Tyr Trp Val Leu Thr Ala Ala His Val Val Glu Gly
```

```
            450                 455                 460
Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
        515                 520                 525

Thr Val Ser Pro Ile Cys Leu Pro Gly Thr Ser Ser Asp Tyr Asn Leu
    530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
    610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp

<210> SEQ ID NO 119
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M8 (E351A)-His

<400> SEQUENCE: 119

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125
```

-continued

```
Ser His Phe Cys Asn Asn Phe Ile Gly Gly Tyr Phe Cys Ser Cys Pro
    130                 135                 140
Pro Glu Tyr Phe Leu His Asp Asp Met Lys Asn Cys Gly Val Asn Cys
145                 150                 155                 160
Ser Gly Asp Val Phe Thr Ala Leu Ile Gly Glu Ile Ala Ser Pro Asn
                165                 170                 175
Tyr Pro Lys Pro Tyr Pro Glu Asn Ser Arg Cys Glu Tyr Gln Ile Arg
            180                 185                 190
Leu Glu Lys Gly Phe Gln Val Val Thr Leu Arg Arg Glu Asp Phe
        195                 200                 205
Asp Val Glu Ala Ala Asp Ser Ala Gly Asn Cys Leu Asp Ser Leu Val
    210                 215                 220
Phe Val Ala Gly Asp Arg Gln Phe Gly Pro Tyr Cys Gly His Gly Phe
225                 230                 235                 240
Pro Gly Pro Leu Asn Ile Glu Thr Lys Ser Asn Ala Leu Asp Ile Ile
                245                 250                 255
Phe Gln Thr Asp Leu Thr Gly Gln Lys Lys Gly Trp Lys Leu Arg Tyr
            260                 265                 270
His Gly Asp Pro Met Pro Cys Pro Lys Glu Asp Thr Pro Asn Ser Val
        275                 280                 285
Trp Glu Pro Ala Lys Ala Lys Tyr Val Phe Arg Asp Val Val Gln Ile
    290                 295                 300
Thr Cys Leu Asp Gly Phe Glu Val Val Glu Gly Arg Val Gly Ala Thr
305                 310                 315                 320
Ser Phe Tyr Ser Thr Cys Gln Ser Asn Gly Lys Trp Ser Asn Ser Lys
                325                 330                 335
Leu Lys Cys Gln Pro Val Asp Cys Gly Ile Pro Glu Ser Ile Ala Asn
            340                 345                 350
Gly Lys Val Glu Asp Pro Glu Ser Thr Leu Phe Gly Ser Val Ile Arg
        355                 360                 365
Tyr Thr Cys Glu Glu Pro Tyr Tyr Met Glu Asn Gly Gly Gly Gly
    370                 375                 380
Glu Tyr His Cys Ala Gly Asn Gly Ser Trp Val Asn Glu Val Leu Gly
385                 390                 395                 400
Pro Glu Leu Pro Lys Cys Val Pro Val Cys Gly Val Pro Arg Glu Pro
                405                 410                 415
Phe Glu Glu Lys Gln Arg Ile Ile Gly Gly Ser Asp Ala Asp Ile Lys
            420                 425                 430
Asn Phe Pro Trp Gln Val Phe Phe Asp Asn Pro Trp Ala Gly Gly Ala
        435                 440                 445
Leu Ile Asn Glu Tyr Trp Val Leu Thr Ala Ala His Val Val Glu Gly
    450                 455                 460
Asn Arg Glu Pro Thr Met Tyr Val Gly Ser Thr Ser Val Gln Thr Ser
465                 470                 475                 480
Arg Leu Ala Lys Ser Lys Met Leu Thr Pro Glu His Val Phe Ile His
                485                 490                 495
Pro Gly Trp Lys Leu Leu Glu Val Pro Glu Gly Arg Thr Asn Phe Asp
            500                 505                 510
Asn Asp Ile Ala Leu Val Arg Leu Lys Asp Pro Val Lys Met Gly Pro
        515                 520                 525
Thr Val Ser Pro Ile Cys Leu Pro Gly Thr Ser Ser Asp Tyr Asn Leu
    530                 535                 540
```

```
Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
                660                 665                 670

Asp

<210> SEQ ID NO 120
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M9 (K336G,
      D343Y, E351A)-His

<400> SEQUENCE: 120

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
                20                  25                  30

Tyr Gly Ile His Leu Tyr Phe Thr His Leu Asp Ile Glu Leu Ser Glu
            35                  40                  45

Asn Cys Ala Tyr Asp Ser Val Gln Ile Ile Ser Gly Asp Thr Glu Glu
50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Val Thr Leu Arg Arg Glu Asp Phe
        195                 200                 205
```

-continued

```
Asp Val Glu Ala Ala Asp Ser Ala Gly Asn Cys Leu Asp Ser Leu Val
    210                 215                 220
Phe Val Ala Gly Asp Arg Gln Phe Gly Pro Tyr Cys Gly His Gly Phe
225                 230                 235                 240
Pro Gly Pro Leu Asn Ile Glu Thr Lys Ser Asn Ala Leu Asp Ile Ile
                245                 250                 255
Phe Gln Thr Asp Leu Thr Gly Gln Lys Lys Gly Trp Lys Leu Arg Tyr
            260                 265                 270
His Gly Asp Pro Met Pro Cys Pro Lys Glu Asp Thr Pro Asn Ser Val
        275                 280                 285
Trp Glu Pro Ala Lys Ala Lys Tyr Val Phe Arg Asp Val Val Gln Ile
290                 295                 300
Thr Cys Leu Asp Gly Phe Glu Val Val Glu Gly Arg Val Gly Ala Thr
305                 310                 315                 320
Ser Phe Tyr Ser Thr Cys Gln Ser Asn Gly Lys Trp Ser Asn Ser Gly
                325                 330                 335
Leu Lys Cys Gln Pro Val Tyr Cys Gly Ile Pro Glu Ser Ile Ala Asn
            340                 345                 350
Gly Lys Val Glu Asp Pro Glu Ser Thr Leu Phe Gly Ser Val Ile Arg
        355                 360                 365
Tyr Thr Cys Glu Glu Pro Tyr Tyr Tyr Met Glu Asn Gly Gly Gly Gly
    370                 375                 380
Glu Tyr His Cys Ala Gly Asn Gly Ser Trp Val Asn Glu Val Leu Gly
385                 390                 395                 400
Pro Glu Leu Pro Lys Cys Val Pro Val Cys Gly Val Pro Arg Glu Pro
                405                 410                 415
Phe Glu Glu Lys Gln Arg Ile Ile Gly Gly Ser Asp Ala Asp Ile Lys
            420                 425                 430
Asn Phe Pro Trp Gln Val Phe Phe Asp Asn Pro Trp Ala Gly Gly Ala
        435                 440                 445
Leu Ile Asn Glu Tyr Trp Val Leu Thr Ala Ala His Val Val Glu Gly
    450                 455                 460
Asn Arg Glu Pro Thr Met Tyr Val Gly Ser Thr Ser Val Gln Thr Ser
465                 470                 475                 480
Arg Leu Ala Lys Ser Lys Met Leu Thr Pro Glu His Val Phe Ile His
                485                 490                 495
Pro Gly Trp Lys Leu Leu Glu Val Pro Glu Gly Arg Thr Asn Phe Asp
            500                 505                 510
Asn Asp Ile Ala Leu Val Arg Leu Lys Asp Pro Val Lys Met Gly Pro
        515                 520                 525
Thr Val Ser Pro Ile Cys Leu Pro Gly Thr Ser Ser Asp Tyr Asn Leu
    530                 535                 540
Met Asp Gly Asp Leu Gly Leu Ile Ser Gly Trp Gly Arg Thr Glu Lys
545                 550                 555                 560
Arg Asp Arg Ala Val Arg Leu Lys Ala Ala Arg Leu Pro Val Ala Pro
                565                 570                 575
Leu Arg Lys Cys Lys Glu Val Lys Val Glu Lys Pro Thr Ala Asp Ala
            580                 585                 590
Glu Ala Tyr Val Phe Thr Pro Asn Met Ile Cys Ala Gly Gly Glu Lys
        595                 600                 605
Gly Met Asp Ser Cys Lys Gly Asp Ser Gly Gly Ala Phe Ala Val Gln
    610                 615                 620
Asp Pro Asn Asp Lys Thr Lys Phe Tyr Ala Ala Gly Leu Val Ser Trp
```

```
              625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
                660                 665                 670

Asp

<210> SEQ ID NO 121
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M10 (D283I,
      P285A)-His

<400> SEQUENCE: 121

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
                20                  25                  30

Tyr Gly Ile His Leu Tyr Phe Thr His Leu Asp Ile Glu Leu Ser Glu
            35                  40                  45

Asn Cys Ala Tyr Asp Ser Val Gln Ile Ile Ser Gly Asp Thr Glu Glu
        50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
                100                 105                 110

Val Ala Thr Asp Ile Asn Glu Cys Thr Asp Phe Val Asp Val Pro Cys
            115                 120                 125

Ser His Phe Cys Asn Asn Phe Ile Gly Gly Tyr Phe Cys Ser Cys Pro
        130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
                180                 185                 190

Leu Glu Lys Gly Phe Gln Val Val Thr Leu Arg Arg Glu Asp Phe
            195                 200                 205

Asp Val Glu Ala Ala Asp Ser Ala Gly Asn Cys Leu Asp Ser Leu Val
        210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
                260                 265                 270

His Gly Asp Pro Met Pro Cys Pro Lys Glu Ile Thr Ala Asn Ser Val
            275                 280                 285

Trp Glu Pro Ala Lys Ala Lys Tyr Val Phe Arg Asp Val Val Gln Ile
```

```
                 290                 295                 300
Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
        355                 360                 365

Tyr Thr Cys Glu Glu Pro Tyr Tyr Tyr Met Glu Asn Gly Gly Gly Gly
    370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
        435                 440                 445

Leu Ile Asn Glu Tyr Trp Val Leu Thr Ala Ala His Val Val Glu Gly
    450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
        515                 520                 525

Thr Val Ser Pro Ile Cys Leu Pro Gly Thr Ser Ser Asp Tyr Asn Leu
    530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
    610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp

<210> SEQ ID NO 122
<211> LENGTH: 673
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<223> OTHER INFORMATION: Protein sequence of human C1s M11 (S349P)-His

<400> SEQUENCE: 122

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Val Thr Leu Arg Arg Glu Asp Phe
        195                 200                 205

Asp Val Glu Ala Ala Asp Ser Ala Gly Asn Cys Leu Asp Ser Leu Val
210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
        275                 280                 285

Trp Glu Pro Ala Lys Ala Lys Tyr Val Phe Arg Asp Val Val Gln Ile
290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Pro Ile Glu Asn
            340                 345                 350

Gly Lys Val Glu Asp Pro Glu Ser Thr Leu Phe Gly Ser Val Ile Arg
        355                 360                 365

Tyr Thr Cys Glu Glu Pro Tyr Tyr Met Glu Asn Gly Gly Gly Gly
370                 375                 380

-continued

```
Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
            405                 410                 415

Phe Glu Glu Lys Gln Arg Ile Ile Gly Gly Ser Asp Ala Asp Ile Lys
        420                 425                 430

Asn Phe Pro Trp Gln Val Phe Phe Asp Asn Pro Trp Ala Gly Gly Ala
            435                 440                 445

Leu Ile Asn Glu Tyr Trp Val Leu Thr Ala Ala His Val Val Glu Gly
    450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
        515                 520                 525

Thr Val Ser Pro Ile Cys Leu Pro Gly Thr Ser Ser Asp Tyr Asn Leu
            530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
    610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp
```

<210> SEQ ID NO 123
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M12 (G381E,
      G382E)-His

<400> SEQUENCE: 123

```
Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45
```

```
Asn Cys Ala Tyr Asp Ser Val Gln Ile Ile Ser Gly Asp Thr Glu Glu
 50                  55                  60

Gly Arg Leu Cys Gly Gln Arg Ser Ser Asn Pro His Ser Pro Ile
 65              70                  75                  80

Val Glu Glu Phe Gln Val Pro Tyr Asn Lys Leu Gln Val Ile Phe Lys
                 85                  90                  95

Ser Asp Phe Ser Asn Glu Glu Arg Phe Thr Gly Phe Ala Ala Tyr Tyr
                100                 105                 110

Val Ala Thr Asp Ile Asn Glu Cys Thr Asp Phe Val Asp Val Pro Cys
                115                 120                 125

Ser His Phe Cys Asn Asn Phe Ile Gly Gly Tyr Phe Cys Ser Cys Pro
            130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                    165                 170                 175

Tyr Pro Lys Pro Tyr Pro Glu Asn Ser Arg Cys Glu Tyr Gln Ile Arg
                180                 185                 190

Leu Glu Lys Gly Phe Gln Val Val Thr Leu Arg Arg Glu Asp Phe
            195                 200                 205

Asp Val Glu Ala Ala Asp Ser Ala Gly Asn Cys Leu Asp Ser Leu Val
            210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
            275                 280                 285

Trp Glu Pro Ala Lys Ala Lys Tyr Val Phe Arg Asp Val Val Gln Ile
290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
            355                 360                 365

Tyr Thr Cys Glu Glu Pro Tyr Tyr Tyr Met Glu Asn Glu Glu Gly Gly
            370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
                420                 425                 430

Asn Phe Pro Trp Gln Val Phe Phe Asp Asn Pro Trp Ala Gly Gly Ala
                435                 440                 445

Leu Ile Asn Glu Tyr Trp Val Leu Thr Ala Ala His Val Val Glu Gly
450                 455                 460

Asn Arg Glu Pro Thr Met Tyr Val Gly Ser Thr Ser Val Gln Thr Ser
```

```
                465                 470                 475                 480
Arg Leu Ala Lys Ser Lys Met Leu Thr Pro Glu His Val Phe Ile His
                485                 490                 495
Pro Gly Trp Lys Leu Leu Glu Val Pro Glu Gly Arg Thr Asn Phe Asp
                500                 505                 510
Asn Asp Ile Ala Leu Val Arg Leu Lys Asp Pro Val Lys Met Gly Pro
                515                 520                 525
Thr Val Ser Pro Ile Cys Leu Pro Gly Thr Ser Ser Asp Tyr Asn Leu
                530                 535                 540
Met Asp Gly Asp Leu Gly Leu Ile Ser Gly Trp Gly Arg Thr Glu Lys
545                 550                 555                 560
Arg Asp Arg Ala Val Arg Leu Lys Ala Ala Arg Leu Pro Val Ala Pro
                565                 570                 575
Leu Arg Lys Cys Lys Glu Val Lys Val Glu Lys Pro Thr Ala Asp Ala
                580                 585                 590
Glu Ala Tyr Val Phe Thr Pro Asn Met Ile Cys Ala Gly Gly Glu Lys
                595                 600                 605
Gly Met Asp Ser Cys Lys Gly Asp Ser Gly Gly Ala Phe Ala Val Gln
                610                 615                 620
Asp Pro Asn Asp Lys Thr Lys Phe Tyr Ala Ala Gly Leu Val Ser Trp
625                 630                 635                 640
Gly Pro Gln Cys Gly Thr Tyr Gly Leu Tyr Thr Arg Val Lys Asn Tyr
                645                 650                 655
Val Asp Trp Ile Met Lys Thr Met Gln Glu Asn Ser Thr Pro Arg Glu
                660                 665                 670
Asp

<210> SEQ ID NO 124
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M13 (A292D)-His

<400> SEQUENCE: 124

Glu Pro Thr Met Tyr Gly Glu Ile Leu Ser Pro Asn Tyr Pro Gln Ala
1               5                   10                  15
Tyr Pro Ser Glu Val Glu Lys Ser Trp Asp Ile Glu Val Pro Glu Gly
                20                  25                  30
Tyr Gly Ile His Leu Tyr Phe Thr His Leu Asp Ile Glu Leu Ser Glu
                35                  40                  45
Asn Cys Ala Tyr Asp Ser Val Gln Ile Ile Ser Gly Asp Thr Glu Glu
                50                  55                  60
Gly Arg Leu Cys Gly Gln Arg Ser Ser Asn Asn Pro His Ser Pro Ile
65                  70                  75                  80
Val Glu Glu Phe Gln Val Pro Tyr Asn Lys Leu Gln Val Ile Phe Lys
                85                  90                  95
Ser Asp Phe Ser Asn Glu Glu Arg Phe Thr Gly Phe Ala Ala Tyr Tyr
                100                 105                 110
Val Ala Thr Asp Ile Asn Glu Cys Thr Asp Phe Val Asp Val Pro Cys
                115                 120                 125
Ser His Phe Cys Asn Asn Phe Ile Gly Gly Tyr Phe Cys Ser Cys Pro
                130                 135                 140
```

```
Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe
        195                 200                 205

Asp Val Glu Ala Ala Asp Ser Ala Gly Asn Cys Leu Asp Ser Leu Val
        210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
        275                 280                 285

Trp Glu Pro Asp Lys Ala Lys Tyr Val Phe Arg Asp Val Val Gln Ile
        290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
        355                 360                 365

Tyr Thr Cys Glu Glu Pro Tyr Tyr Tyr Met Glu Asn Gly Gly Gly Gly
        370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
            435                 440                 445

Leu Ile Asn Glu Tyr Trp Val Leu Thr Ala Ala His Val Val Glu Gly
        450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
        515                 520                 525

Thr Val Ser Pro Ile Cys Leu Pro Gly Thr Ser Ser Asp Tyr Asn Leu
        530                 535                 540

Met Asp Gly Asp Leu Gly Leu Ile Ser Gly Trp Gly Arg Thr Glu Lys
545                 550                 555                 560
```

```
Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
                660                 665                 670

Asp

<210> SEQ ID NO 125
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M14 (R316H)-His

<400> SEQUENCE: 125

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe
        195                 200                 205

Asp Val Glu Ala Ala Asp Ser Ala Gly Asn Cys Leu Asp Ser Leu Val
    210                 215                 220

Phe Val Ala Gly Asp Arg Gln Phe Gly Pro Tyr Cys Gly His Gly Phe
```

```
225                 230                 235                 240
Pro Gly Pro Leu Asn Ile Glu Thr Lys Ser Asn Ala Leu Asp Ile Ile
                245                 250                 255
Phe Gln Thr Asp Leu Thr Gly Gln Lys Lys Gly Trp Lys Leu Arg Tyr
            260                 265                 270
His Gly Asp Pro Met Pro Cys Pro Lys Glu Asp Thr Pro Asn Ser Val
            275                 280                 285
Trp Glu Pro Ala Lys Ala Lys Tyr Val Phe Arg Asp Val Val Gln Ile
        290                 295                 300
Thr Cys Leu Asp Gly Phe Glu Val Val Glu Gly His Val Gly Ala Thr
305                 310                 315                 320
Ser Phe Tyr Ser Thr Cys Gln Ser Asn Gly Lys Trp Ser Asn Ser Lys
                325                 330                 335
Leu Lys Cys Gln Pro Val Asp Cys Gly Ile Pro Glu Ser Ile Glu Asn
            340                 345                 350
Gly Lys Val Glu Asp Pro Glu Ser Thr Leu Phe Gly Ser Val Ile Arg
            355                 360                 365
Tyr Thr Cys Glu Glu Pro Tyr Tyr Tyr Met Glu Asn Gly Gly Gly Gly
        370                 375                 380
Glu Tyr His Cys Ala Gly Asn Gly Ser Trp Val Asn Glu Val Leu Gly
385                 390                 395                 400
Pro Glu Leu Pro Lys Cys Val Pro Val Cys Gly Val Pro Arg Glu Pro
                405                 410                 415
Phe Glu Glu Lys Gln Arg Ile Ile Gly Gly Ser Asp Ala Asp Ile Lys
            420                 425                 430
Asn Phe Pro Trp Gln Val Phe Phe Asp Asn Pro Trp Ala Gly Gly Ala
            435                 440                 445
Leu Ile Asn Glu Tyr Trp Val Leu Thr Ala Ala His Val Val Glu Gly
        450                 455                 460
Asn Arg Glu Pro Thr Met Tyr Val Gly Ser Thr Ser Val Gln Thr Ser
465                 470                 475                 480
Arg Leu Ala Lys Ser Lys Met Leu Thr Pro Glu His Val Phe Ile His
                485                 490                 495
Pro Gly Trp Lys Leu Leu Glu Val Pro Glu Gly Arg Thr Asn Phe Asp
            500                 505                 510
Asn Asp Ile Ala Leu Val Arg Leu Lys Asp Pro Val Lys Met Gly Pro
            515                 520                 525
Thr Val Ser Pro Ile Cys Leu Pro Gly Thr Ser Ser Asp Tyr Asn Leu
        530                 535                 540
Met Asp Gly Asp Leu Gly Leu Ile Ser Gly Trp Gly Arg Thr Glu Lys
545                 550                 555                 560
Arg Asp Arg Ala Val Arg Leu Lys Ala Ala Arg Leu Pro Val Ala Pro
                565                 570                 575
Leu Arg Lys Cys Lys Glu Val Lys Val Glu Lys Pro Thr Ala Asp Ala
            580                 585                 590
Glu Ala Tyr Val Phe Thr Pro Asn Met Ile Cys Ala Gly Gly Glu Lys
            595                 600                 605
Gly Met Asp Ser Cys Lys Gly Asp Ser Gly Gly Ala Phe Ala Val Gln
        610                 615                 620
Asp Pro Asn Asp Lys Thr Lys Phe Tyr Ala Ala Gly Leu Val Ser Trp
625                 630                 635                 640
Gly Pro Gln Cys Gly Thr Tyr Gly Leu Tyr Thr Arg Val Lys Asn Tyr
                645                 650                 655
```

```
Val Asp Trp Ile Met Lys Thr Met Gln Glu Asn Ser Thr Pro Arg Glu
            660                 665                 670

Asp

<210> SEQ ID NO 126
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M15 (S360N)-His

<400> SEQUENCE: 126

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Val Thr Leu Arg Arg Glu Asp Phe
        195                 200                 205

Asp Val Glu Ala Ala Asp Ser Ala Gly Asn Cys Leu Asp Ser Leu Val
    210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
        275                 280                 285

Trp Glu Pro Ala Lys Ala Lys Tyr Val Phe Arg Asp Val Val Gln Ile
    290                 295                 300

Thr Cys Leu Asp Gly Phe Glu Val Val Glu Gly Arg Val Gly Ala Thr
305                 310                 315                 320
```

Ser Phe Tyr Ser Thr Cys Gln Ser Asn Gly Lys Trp Ser Asn Ser Lys
              325                 330                 335

Leu Lys Cys Gln Pro Val Asp Cys Gly Ile Pro Glu Ser Ile Glu Asn
          340                 345                 350

Gly Lys Val Glu Asp Pro Glu Asn Thr Leu Phe Gly Ser Val Ile Arg
          355                 360                 365

Tyr Thr Cys Glu Glu Pro Tyr Tyr Met Glu Asn Gly Gly Gly Gly
          370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                  405                 410                 415

Phe Glu Glu Lys Gln Arg Ile Ile Gly Gly Ser Asp Ala Asp Ile Lys
              420                 425                 430

Asn Phe Pro Trp Gln Val Phe Phe Asp Asn Pro Trp Ala Gly Gly Ala
              435                 440                 445

Leu Ile Asn Glu Tyr Trp Val Leu Thr Ala Ala His Val Val Glu Gly
450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                  485                 490                 495

Pro Gly Trp Lys Leu Leu Glu Val Pro Glu Gly Arg Thr Asn Phe Asp
                  500                 505                 510

Asn Asp Ile Ala Leu Val Arg Leu Lys Asp Pro Val Lys Met Gly Pro
              515                 520                 525

Thr Val Ser Pro Ile Cys Leu Pro Gly Thr Ser Ser Asp Tyr Asn Leu
              530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                  565                 570                 575

Leu Arg Lys Cys Lys Glu Val Lys Val Glu Lys Pro Thr Ala Asp Ala
              580                 585                 590

Glu Ala Tyr Val Phe Thr Pro Asn Met Ile Cys Ala Gly Gly Glu Lys
              595                 600                 605

Gly Met Asp Ser Cys Lys Gly Asp Ser Gly Gly Ala Phe Ala Val Gln
          610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                  645                 650                 655

Val Asp Trp Ile Met Lys Thr Met Gln Glu Asn Ser Thr Pro Arg Glu
              660                 665                 670

Asp

<210> SEQ ID NO 127
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M16 (R368H)-His

<400> SEQUENCE: 127

| | | | | | | | | | | | | | | |
|---|---|---|---|---|---|---|---|---|---|---|---|---|---|---|
| Glu | Pro | Thr | Met | Tyr | Gly | Glu | Ile | Leu | Ser | Pro | Asn | Tyr | Pro | Gln | Ala |
| 1 | | | | 5 | | | | | 10 | | | | | 15 | |

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
                35                  40                  45

Asn Cys Ala Tyr Asp Ser Val Gln Ile Ile Ser Gly Asp Thr Glu Glu
        50                  55                  60

Gly Arg Leu Cys Gly Gln Arg Ser Ser Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
                100                 105                 110

Val Ala Thr Asp Ile Asn Glu Cys Thr Asp Phe Val Asp Val Pro Cys
            115                 120                 125

Ser His Phe Cys Asn Asn Phe Ile Gly Gly Tyr Phe Cys Ser Cys Pro
        130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
                180                 185                 190

Leu Glu Lys Gly Phe Gln Val Val Thr Leu Arg Arg Glu Asp Phe
            195                 200                 205

Asp Val Glu Ala Ala Asp Ser Ala Gly Asn Cys Leu Asp Ser Leu Val
        210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
                260                 265                 270

His Gly Asp Pro Met Pro Cys Pro Lys Glu Asp Thr Pro Asn Ser Val
            275                 280                 285

Trp Glu Pro Ala Lys Ala Lys Tyr Val Phe Arg Asp Val Val Gln Ile
290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile His
            355                 360                 365

Tyr Thr Cys Glu Glu Pro Tyr Tyr Tyr Met Glu Asn Gly Gly Gly Gly
        370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

```
Phe Glu Glu Lys Gln Arg Ile Ile Gly Gly Ser Asp Ala Asp Ile Lys
            420                 425                 430

Asn Phe Pro Trp Gln Val Phe Asp Asn Pro Trp Ala Gly Gly Ala
            435                 440                 445

Leu Ile Asn Glu Tyr Trp Val Leu Thr Ala Ala His Val Val Glu Gly
450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
            515                 520                 525

Thr Val Ser Pro Ile Cys Leu Pro Gly Thr Ser Ser Asp Tyr Asn Leu
            530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
            595                 600                 605

Gly Met Asp Ser Cys Lys Gly Asp Ser Gly Gly Ala Phe Ala Val Gln
            610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp

<210> SEQ ID NO 128
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M17 (N380H)-His

<400> SEQUENCE: 128

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
            35                  40                  45

Asn Cys Ala Tyr Asp Ser Val Gln Ile Ile Ser Gly Asp Thr Glu Glu
            50                  55                  60

Gly Arg Leu Cys Gly Gln Arg Ser Ser Asn Asn Pro His Ser Pro Ile
65                  70                  75                  80
```

Val Glu Glu Phe Gln Val Pro Tyr Asn Lys Leu Gln Val Ile Phe Lys
            85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
            115                 120                 125

Ser His Phe Cys Asn Asn Phe Ile Gly Gly Tyr Phe Cys Ser Cys Pro
            130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
            165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe
            195                 200                 205

Asp Val Glu Ala Ala Asp Ser Ala Gly Asn Cys Leu Asp Ser Leu Val
            210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
            245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
            275                 280                 285

Trp Glu Pro Ala Lys Ala Lys Tyr Val Phe Arg Asp Val Val Gln Ile
290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
            325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
            355                 360                 365

Tyr Thr Cys Glu Glu Pro Tyr Tyr Met Glu His Gly Gly Gly Gly
            370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
            405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
            435                 440                 445

Leu Ile Asn Glu Tyr Trp Val Leu Thr Ala Ala His Val Val Glu Gly
            450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
            485                 490                 495

Pro Gly Trp Lys Leu Leu Glu Val Pro Glu Gly Arg Thr Asn Phe Asp

```
                     500                 505                 510

Asn Asp Ile Ala Leu Val Arg Leu Lys Asp Pro Val Lys Met Gly Pro
            515                 520                 525

Thr Val Ser Pro Ile Cys Leu Pro Gly Thr Ser Ser Asp Tyr Asn Leu
        530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
                610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus HC-CDR-1 sequence by alignment of
      antibody 2-7; hz2-7(H1L2); and hz2-7(H1L2 G131A)

<400> SEQUENCE: 129

Gly Phe Thr Phe Ser Asn Tyr Phe Met Asn
1               5                   10

<210> SEQ ID NO 130
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus HC-CDR-2 sequence by alignment of
      antibody 2-7; hz2-7(H1L2); and hz2-7(H1L2 G131A)
<220> FEATURE:
<221> NAME/KEY: MOD_RES
<222> LOCATION: (15)..(15)
<223> OTHER INFORMATION: E or D
<220> FEATURE:
<221> NAME/KEY: MOD_RES
<222> LOCATION: (18)..(18)
<223> OTHER INFORMATION: E or K

<400> SEQUENCE: 130

Glu Ile Arg Leu Lys Phe Thr Asn Tyr Ala Thr His Tyr Ala Xaa Ser
1               5                   10                  15

Val Xaa Gly
```

```
<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus HC-CDR-3 sequence by alignment of
      antibody 2-7; hz2-7(H1L2); and hz2-7(H1L2 G131A)
<220> FEATURE:
<221> NAME/KEY: MOD_RES
<222> LOCATION: (7)..(7)
<223> OTHER INFORMATION: G or A

<400> SEQUENCE: 131

Asp Tyr Gly Ser Arg Asn Xaa Tyr Phe Asp Tyr
1               5                   10

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus LC-CDR-1 sequence by alignment of
      antibody 2-7; hz2-7(H1L2); and hz2-7(H1L2 G131A)

<400> SEQUENCE: 132

Arg Ser Ser Lys Ser Leu Leu His Ser Asn Gly Asn Thr Phe Leu Tyr
1               5                   10                  15

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus LC-CDR-2 sequence by alignment of
      antibody 2-7; hz2-7(H1L2); and hz2-7(H1L2 G131A)

<400> SEQUENCE: 133

Arg Met Ser Asn Leu Ala Ser
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus LC-CDR-3 sequence by alignment of
      antibody 2-7; hz2-7(H1L2); and hz2-7(H1L2 G131A)

<400> SEQUENCE: 134

Met Gln His Leu Glu Tyr Pro Tyr Thr
1               5

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: Consensus HC-CDR-1 sequence by alignment of
      antibody 2-8; hz2-8(H1L2); hz2-8(H1L2 G80A/T82A);
      and hz2-8(H1L2 G80A)

<400> SEQUENCE: 135

Gly Phe Asn Ile Lys Glu Tyr Tyr Met His
1               5                   10

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus HC-CDR-2 sequence by alignment of
      antibody 2-8; hz2-8(H1L2); hz2-8(H1L2 G80A/T82A);
      and hz2-8(H1L2 G80A)
<220> FEATURE:
<221> NAME/KEY: MOD_RES
<222> LOCATION: (7)..(7)
<223> OTHER INFORMATION: G or A
<220> FEATURE:
<221> NAME/KEY: MOD_RES
<222> LOCATION: (9)..(9)
<223> OTHER INFORMATION: T or A
<220> FEATURE:
<221> NAME/KEY: MOD_RES
<222> LOCATION: (12)..(12)
<223> OTHER INFORMATION: D or A
<220> FEATURE:
<221> NAME/KEY: MOD_RES
<222> LOCATION: (13)..(13)
<223> OTHER INFORMATION: P or Q

<400> SEQUENCE: 136

Trp Ile Asp Pro Glu Asn Xaa Asp Xaa Ile Tyr Xaa Xaa Lys Phe Gln
1               5                   10                  15

Gly

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus HC-CDR-3 sequence by alignment of
      antibody 2-8; hz2-8(H1L2); hz2-8(H1L2 G80A/T82A);
      and hz2-8(H1L2 G80A)

<400> SEQUENCE: 137

Ser Arg Leu Phe Phe Ala Tyr
1               5

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus LC-CDR-1 sequence by alignment of
      antibody 2-8; hz2-8(H1L2); hz2-8(H1L2 G80A/T82A);
      and hz2-8(H1L2 G80A)
<220> FEATURE:
<221> NAME/KEY: MOD_RES
<222> LOCATION: (1)..(1)
```

```
<223> OTHER INFORMATION: K or R
<220> FEATURE:
<221> NAME/KEY: MOD_RES
<222> LOCATION: (10)..(10)
<223> OTHER INFORMATION: V or L

<400> SEQUENCE: 138

Xaa Ala Ser Gln Asp Val Arg Thr Ala Xaa Asp
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus LC-CDR-2 sequence by alignment of
      antibody 2-8; hz2-8(H1L2); hz2-8(H1L2 G80A/T82A);
      and hz2-8(H1L2 G80A)
<220> FEATURE:
<221> NAME/KEY: MOD_RES
<222> LOCATION: (7)..(7)
<223> OTHER INFORMATION: T or S

<400> SEQUENCE: 139

Ser Ala Ser Tyr Arg Tyr Xaa
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus LC-CDR-3 sequence by alignment of
      antibody 2-8; hz2-8(H1L2); hz2-8(H1L2 G80A/T82A);
      and hz2-8(H1L2 G80A)

<400> SEQUENCE: 140

Gln Gln Gln Tyr Thr Thr Pro Tyr Thr
1               5

<210> SEQ ID NO 141
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M18 (V288T)-His

<400> SEQUENCE: 141

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Asn Pro His Ser Pro Ile
65                  70                  75                  80
```

-continued

```
Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe
        195                 200                 205

Asp Val Glu Ala Ala Asp Ser Ala Gly Asn Cys Leu Asp Ser Leu Val
    210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Thr
        275                 280                 285

Trp Glu Pro Ala Lys Ala Lys Tyr Val Phe Arg Asp Val Val Gln Ile
    290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
        355                 360                 365

Tyr Thr Cys Glu Glu Pro Tyr Tyr Tyr Met Glu Asn Gly Gly Gly Gly
    370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
        435                 440                 445

Leu Ile Asn Glu Tyr Trp Val Leu Thr Ala Ala His Val Val Glu Gly
    450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
```

```
                500                 505                 510
Asn Asp Ile Ala Leu Val Arg Leu Lys Asp Pro Val Lys Met Gly Pro
            515                 520                 525

Thr Val Ser Pro Ile Cys Leu Pro Gly Thr Ser Ser Asp Tyr Asn Leu
            530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
            595                 600                 605

Gly Met Asp Ser Cys Lys Gly Asp Ser Gly Gly Ala Phe Ala Val Gln
        610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp
```

<210> SEQ ID NO 142
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M19 (Q303K)-His

<400> SEQUENCE: 142

```
Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175
```

```
Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe
            195                 200                 205

Asp Val Glu Ala Ala Asp Ser Ala Gly Asn Cys Leu Asp Ser Leu Val
            210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
            245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
            275                 280                 285

Trp Glu Pro Ala Lys Ala Lys Tyr Val Phe Arg Asp Val Val Lys Ile
            290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
            325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
            355                 360                 365

Tyr Thr Cys Glu Glu Pro Tyr Tyr Met Glu Asn Gly Gly Gly Gly
            370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
            405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
            435                 440                 445

Leu Ile Asn Glu Tyr Trp Val Leu Thr Ala Ala His Val Val Glu Gly
            450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
            485                 490                 495

Pro Gly Trp Lys Leu Leu Glu Val Pro Glu Gly Arg Thr Asn Phe Asp
            500                 505                 510

Asn Asp Ile Ala Leu Val Arg Leu Lys Asp Pro Val Lys Met Gly Pro
            515                 520                 525

Thr Val Ser Pro Ile Cys Leu Pro Gly Thr Ser Ser Asp Tyr Asn Leu
            530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
            565                 570                 575

Leu Arg Lys Cys Lys Glu Val Lys Val Glu Lys Pro Thr Ala Asp Ala
            580                 585                 590
```

```
Glu Ala Tyr Val Phe Thr Pro Asn Met Ile Cys Ala Gly Gly Glu Lys
            595                 600                 605

Gly Met Asp Ser Cys Lys Gly Asp Ser Gly Gly Ala Phe Ala Val Gln
    610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp

<210> SEQ ID NO 143
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Protein sequence of human C1s M20 (A320S)-His

<400> SEQUENCE: 143

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Asn Pro His Ser Pro Ile
65                  70                  75                  80

Val Glu Glu Phe Gln Val Pro Tyr Asn Lys Leu Gln Val Ile Phe Lys
                85                  90                  95

Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
        115                 120                 125

Ser His Phe Cys Asn Asn Phe Ile Gly Gly Tyr Phe Cys Ser Cys Pro
    130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Val Thr Leu Arg Arg Glu Asp Phe
        195                 200                 205

Asp Val Glu Ala Ala Asp Ser Ala Gly Asn Cys Leu Asp Ser Leu Val
    210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
```

```
                260                 265                 270
His Gly Asp Pro Met Pro Cys Pro Lys Glu Asp Thr Pro Asn Ser Val
            275                 280                 285

Trp Glu Pro Ala Lys Ala Lys Tyr Val Phe Arg Asp Val Val Gln Ile
290                 295                 300

Thr Cys Leu Asp Gly Phe Glu Val Val Glu Gly Arg Val Gly Ser Thr
305                 310                 315                 320

Ser Phe Tyr Ser Thr Cys Gln Ser Asn Gly Lys Trp Ser Asn Ser Lys
            325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
            355                 360                 365

Tyr Thr Cys Glu Glu Pro Tyr Tyr Tyr Met Glu Asn Gly Gly Gly Gly
            370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
                420                 425                 430

Asn Phe Pro Trp Gln Val Phe Phe Asp Asn Pro Trp Ala Gly Gly Ala
            435                 440                 445

Leu Ile Asn Glu Tyr Trp Val Leu Thr Ala Ala His Val Val Glu Gly
            450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
                500                 505                 510

Asn Asp Ile Ala Leu Val Arg Leu Lys Asp Pro Val Lys Met Gly Pro
            515                 520                 525

Thr Val Ser Pro Ile Cys Leu Pro Gly Thr Ser Ser Asp Tyr Asn Leu
530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
                580                 585                 590

Glu Ala Tyr Val Phe Thr Pro Asn Met Ile Cys Ala Gly Gly Glu Lys
            595                 600                 605

Gly Met Asp Ser Cys Lys Gly Asp Ser Gly Gly Ala Phe Ala Val Gln
            610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
                660                 665                 670

Asp
```